United States Patent [19]
Luo et al.

[11] Patent Number: 6,090,609
[45] Date of Patent: Jul. 18, 2000

[54] CRYSTALLIZED N-TERMINAL DOMAIN OF INFLUENZA VIRUS MATRIX PROTEIN M1 AND METHOD OF DETERMINING AND USING SAME

[75] Inventors: Ming Luo; Bingdong Sha, both of Birmingham, Ala.

[73] Assignee: University of Alabama Research Foundation, Birmingham, Ala.

[21] Appl. No.: 08/904,489

[22] Filed: Aug. 1, 1997

Related U.S. Application Data

[60] Provisional application No. 60/023,564, Aug. 7, 1996.

[51] Int. Cl.$^7$ .............................. C12N 7/00; C12N 7/04; C07K 14/11; C12Q 1/70

[52] U.S. Cl. ................... 435/235.1; 435/236; 435/239; 435/5; 530/350; 378/74; 378/73; 424/204.1; 424/206.1

[58] Field of Search ................ 530/350; 435/5, 435/235.1, 236–239; 378/73, 74; 424/204.1, 206.1

[56] References Cited

PUBLICATIONS

YE et al , Journal of Virology, 1987, vol. 61, No. 2, pp. 239–246, 1987.
Sha et al, Nature Structural Biology, Mar. 1997, vol. 4, No. 3, pp. 239–244, Mar. 1997.
Helenius, A., Unpacking the incoming influenza virus, Cell 69:577–578 (1992).
Zhirnov., O.P., Isolation of matrix protein M1 from influenza virus by acid–dependent extraction with nonionic detergent, Virology 186:324–330 (1992).
Martin, K. and Helenius, A., Transport of incoming influenza virus nucleocapsids into the nucleus, J. Virology 65:232–244 (1991).
Martin, K. and Helenius, A., Nuclear transport of influenza virus ribonucleoproteins: the viral matrix protein (m1) promotes export and inhibits import, Cell 67:117–130 (1991).
Zhirnov., O.P., Solubilization of matrix protein M1/M from virions occurs at different pH for Orthomyxo–and Paramyxoviruses, Virology 176:274–279 (1990).
Hankins et al., Monoclonal antibody analysis of influenza virus matrix protein epitopes involved in transcription inhibition, Virus Genes. 3(2):111–126, (1989).
Ye et al., Transcription–inhibition and RNA–binding domains of influenza A virus matrix protein mapped with anti–idiotypic antibodies and synthetic peptides, J. Virol. 63:3586–3594 (1989).
Wakefield, L. and Brownlee, G.G., RNA–binding properties of influenza A virus matrix protein M1, Nucleic Acids Res. 17:8569–8580 (1989).
Ye et al., Functional and antigenic domains of the matrix (M1) protein of influenza A virus, J. Virol. 61:239–246 (1987).
Winter, G. and Fields, S., The structure of the gene enclosing the nucleoprotein of human influenza virus A/PR/8/34, Virology 114:423–428 (1981).
Winter, G. and Fields, S., Cloning of influenza cDNA into M13: the sequence of the RNA segment encoding the A/PR/8/34 matrix protein, Nucleic Acids Res. 8:1965–1974 (1980).
Bucher et al., Incorporation of influenza virus M–protein into liposomes, J. Virol. 36:586–590 (1980).
Pons et al., Isolation and characterization of the ribonucleoprotein of influenza virus, Virology 39:250–259 (1969).

*Primary Examiner*—Mary E. Mosher
*Assistant Examiner*—Ali R. Salimi
*Attorney, Agent, or Firm*—Needle & Rosenberg, P.C.

[57] ABSTRACT

The matrix protein, M1, of influenza virus strain A/PR/8/34 has been purified from virions and crystallized. The crystals consist of a stable fragment (18 Kd) of the M1 protein. X-ray diffraction studies indicated that the crystals have a space group of $P3_121$ or $P3_221$. Vm calculations showed that there are two monomers in an asymmetric unit. A crystallized N-terminal domain of M1, wherein the N-terminal domain of M1 is crystallized such that the three dimensional structure of the crystallized N-terminal domain of M1 can be determined to a resolution of about 2.1 Å or better, and wherein the three dimensional structure of the uncrystallized N-terminal domain of M1 cannot be determined to a resolution of about 2.1 Å or better. A method of purifying M1 and a method of crystallizing M1. A method of using the three-dimensional crystal structure of M1 to screen for antiviral, influenza virus treating or preventing compounds. A method of using the three-dimensional crystal structure of M1 to screen for improved binding to or inhibition of influenza virus M1. The use of the three-dimensional crystal structure of the M1 protein of influenza virus in the manufacture of an inhibitor of influenza virus M1. The use of the three-dimensional crystal structure of the M1 protein of influenza virus in the screening of candidates for inhibition of influenza virus M1.

18 Claims, 8 Drawing Sheets

| Res. limits (Å) | I/sigma (I) | Rsymm % | % of observations | Observations/ reflections |
|---|---|---|---|---|
| 25.00  3.78 | 44.1 | 2.7 | 95.4 | 2.8 |
| 3.78  3.00 | 42.4 | 3.9 | 96.0 | 3.0 |
| 3.00  2.62 | 33.0 | 5.4 | 95.9 | 3.0 |
| 2.62  2.38 | 24.6 | 7.8 | 96.0 | 3.0 |
| 2.38  2.21 | 18.5 | 10.2 | 95.9 | 3.0 |
| 2.21  2.08 | 9.1 | 17.5 | 88.6 | 2.6 |
| All | 33.7 | 4.6 | 94.7 | 2.9 |
| Space group: $P3_121$, a=b=67.17Å, c-135.30Å | | | | |

FIG. 3

CRYSTALLIZED N-TERMINAL DOMAIN OF INFLUENZA VIRUS MATRIX PROTEIN M1 AND METHOD OF DETERMINING AND USING SAME

BACKGROUND OF THE INVENTION

This application claims benefit, pursuant to 35 U.S.C. § 119, of applicants' provisional U.S. Ser. No. 60/023,564, filed Aug. 7, 1996, the contents of which are hereby incorporated by is reference.

This application was supported, in part, by a grant from NASA (NAGW-819).

FIELD OF THE INVENTION

The present invention relates to the field of crystallography and, particularly, to the characterization of the structure of matrix protein M1 of influenza virus neuraminidase and, specifically, the determination of the crystal structure of the N-terminal domain of M1, the domain itself, the crystallized domain, methods of purifying and crystallographically determining the three-dimensional structure of that domain, and methods of using the crystal structure of N-terminal domain of M1 to design pharmaceuticals.

BACKGROUND OF THE INVENTION

Influenza virus is an enveloped virus which contains eight separate segments of negative-stranded RNA genome. There are two spike glycoproteins on the surface of the viral membrane envelope, the receptor binding hemagglutinin (HA), and the neuraminidase (NA). The core ribonucleoprotein (RNP) encapsulated in the viral membrane envelope is composed of an RNA polymerase and RNA-binding nucleoproteins (NP) (1). The interaction of RNPs with the membrane is mediated by the matrix protein M1 (252 amino acids, Mr=27 kd), which are tightly associated with the RNP cores while interacting with the cytoplasmic tails of the spike glycoprotein and the viral membrane (2). Through the binding of hydrophobic domains to the virion lipid envelope, M1 maintains the structural integrity of the virus particle (3,4). On the other hand, the interaction of M1 with RNP cores is mostly electrostatic at neutral pH (5,6). The M1 can easily be dissociated from the RNP cores by low pH treatment (7,8).

In addition to packaging the RNP cores during virion assembly, M1 also directs the transportation of RNPs into or out of the nucleus (9,10). Upon entry of the virus into the new host cell, M1 is dissociated from RNPs as the result of reducing pH in the fusion endosome, allowing the RNPs to enter the nucleus. When progeny viral RNPs are produced, newly synthesized M1 escort the RNPs out of nucleus and target them to the assembly site on the cellular membrane where HA and NA are located. It is therefore highly desirable to provide a method of deducing the crystal structure of M1 and of providing a method of using this structure provide antiviral candidates and M1 inhibitors.

SUMMARY OF THE INVENTION

The present invention provides a crystallized N-terminal domain of M1, wherein the N-terminal domain of M1 is crystallized such that the three dimensional structure of the crystallized N-terminal domain of M1 can be determined to a resolution of 2.1 Å or better, and wherein the three-dimensional structure of the uncrystallized N-terminal domain of M1 cannot be determined to a resolution of 2.1 Å or better.

In an alternate embodiment, the present invention provides a method of extracting the M1 protein of influenza virus comprising stripping the membrane proteins from influenza virus, removing the stripped membrane proteins, thereby leaving the M1-RNP complex, and releasing M1 from the M1-RNP complex by suspending the complex in a solution comprising $NaH_2PO_4$, Benzamidine, and $NaN_3$, at a pH of from 3 to 5, preferably about 4.0. In a further embodiment, the released M1 is purified.

In yet another embodiment, the present invention provides a method of extracting the N-terminal domain of the M1 protein of influenza virus comprising stripping the membrane proteins from influenza virus, removing the stripped membrane proteins, thereby leaving the M1-RNP complex, releasing M1 from the M1-RNP complex by suspending the complex in a solution comprising $NaH_2PO_4$, Benzamidine, and $NaN_3$, at a pH of from 3.0 to 5.0, more preferably about 4.0, purifying the released M1, concentrating the purified M1 to a concentration of from about 3 to about 20 mg/ml, more preferably from about 4 to about 10 mg/ml, and most preferably about 5 mg/ml and after a period of time sufficient for the formation of an 18 kd protein fragment corresponding to the N-terminal domain of M1, collecting the 18 kd polypeptide corresponding to the N-terminal domain of M1. In a further embodiment, the method also includes crystallizing the 18 kd polypeptide corresponding to the N-terminal domain of M1 in hanging drops (which is one crystal formation method, see elsewhere herein for others) using the vapor diffusion method to a resolution of less than about 2.1 Å, wherein the N-terminal domain of M1 is present at a concentration of from 3 to 20 mg/mi, preferably 5 mg/ml, and the crystallization takes place at 4 to 32° C. over 20% PEG 3350, to thereby obtain crystals of space group $P3_121$ or $P3_221$ with approximate a=68.0 Å and approximate c=136.57 Å.

In yet another embodiment, the present invention provides a method for determining the three dimensional structure of the crystallized N-terminal domain of the M1 protein of influenza virus to a resolution of 2.1 Å or better comprising the steps of crystallizing the N-terminal domain of M1 in hanging drops using the vapor diffusion method to a resolution of less than about 2.1 Å, wherein the N-terminal domain of M1 is present at a concentration of about 3 to about 20 mg/ml and the crystallization takes place at from about 4 to about 32° C. over 20% PEG 3350, to thereby obtain crystals of space group $P3_121$ or $P3_221$ with approximate a=68.0 Å and approximate c=136.57Å, and then analyzing the N-terminal domain of M1 to determine the three-dimensional structure of the crystallized N-terminal domain of M1. In a further embodiment, the invention provides the crystallized N-terminal domain of M1 produced by this process.

In yet another embodiment, the present invention provides a method for designing an antiviral compound for the prevention or treatment of influenza virus infection, comprising evaluating the three dimensional structure of the crystallized N-terminal domain of M1 produced by crystallizing a purified N-terminal domain of M1 in hanging drops using the vapor diffusion method to a resolution of less than about 2.1 Å, wherein the N-terminal domain of M1 is present at a concentration of about 3 to about 20 mg/ml and the crystallization takes place at from about 4 to about 32° C. over 20% PEG 3350, to thereby obtain crystals of space group $P3_121$ or $P3_221$ with approximate a=68.0 Å and approximate c=136.57 Å, and synthesizing an antiviral compound based on the three-dimensional crystal structure of the crystallized N-terminal domain of M1, wherein the antiviral compound can be screened for having improved binding to M1.

In yet another embodiment, the present invention provides a purified N-terminal domain of M1. In a further embodiment, the present invention provides this purified N-terminal domain of M1, comprising the amino acid sequence of SEQ. ID. NO. 1 (see below). In one embodiment, "N-terminal domain" means the amino acid sequence of SEQ. ID. NO. 1. One of skill in the art would recognize that various amino acid substitutions could be made to this polypeptide. Such modifications, so long as the basic and novel utility of the present invention is not disturbed, are understood to be within the scope of the present invention. For instance, a polypeptide could be constructed containing the first 150 amino acids, from position 1 (perhaps by cleavage of some of the amino acids and addition at the N-terminal end). Such a polypeptide is intended to be within the scope of the present invention. To the extent that the crystal structures of such analogous polypeptides are similar to the structure set forth herein, such structures fall within the scope of the present invention.

In yet another embodiment, the present invention provides a method for designing a candidate compound for screening for improved binding to or inhibition of influenza virus M1, comprising evaluating the three dimensional structure of the crystallized N-terminal domain of M1, and synthesizing a candidate binding compound based on the three-dimensional crystal structure of the crystallized N-terminal domain of M1 for improved binding to M1.

In a further embodiment, the present invention provides the three-dimensional crystal structure of influenza virus protein M1 as set forth elsewhere herein. In a further embodiment, the present invention provides a crystallized polypeptide having that three-dimensional crystal structure.

In yet another embodiment, the invention provides a method for designing a candidate compound for screening as an antiviral for the prevention or treatment of influenza virus infection, comprising evaluating the three-dimensional crystal structure set forth elsewhere herein, and synthesizing a candidate compound based on the three-dimensional crystal structure. Moreover, the present invention provides for the use of the three-dimensional crystal structure as set forth herein for screening candidate compounds for inhibition of influenza virus M1.

In a further embodiment, the present invention also provides for the use of the N-terminal domain of M1 for screening candidate compounds for inhibition of influenza virus M1.

Finally, the present invention provides a crystallized N-terminal domain of M1.

BRIEF DESCRIPTION OF THE DRAWINGS

FIG. 3 shows atomic coordinates of the three dimensional crystal structure of influenza virus protein M1.

DETAILED DESCRIPTION OF THE PREFERRED EMBODIMENTS

Figure 1A:
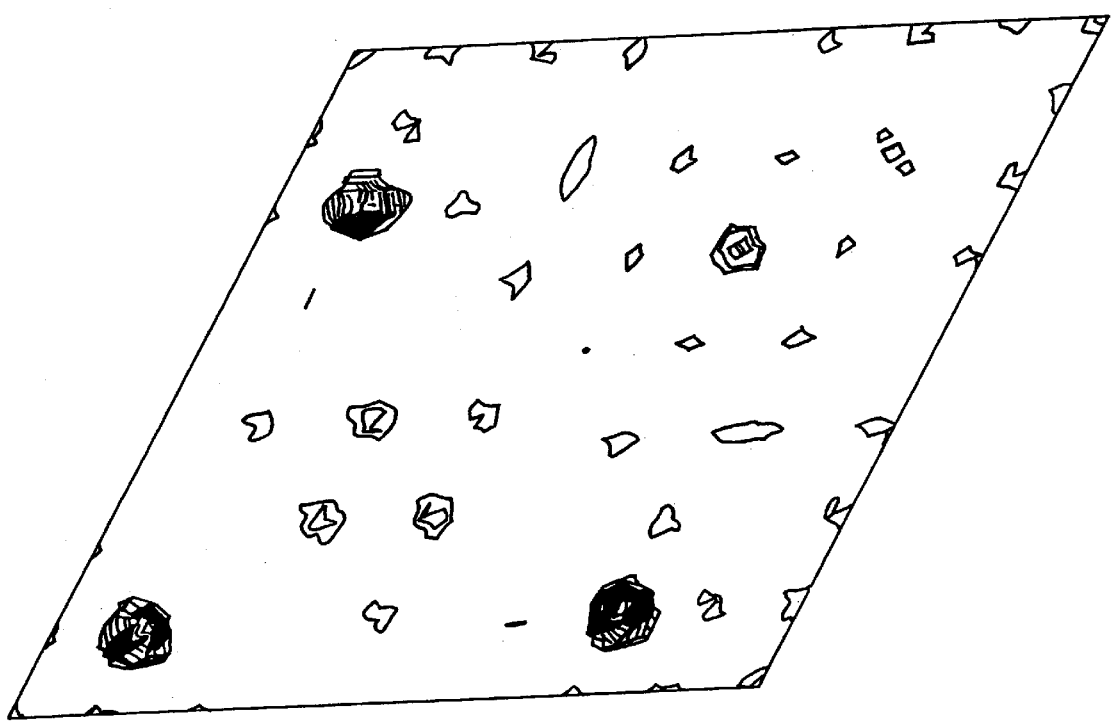
FIG. 1a shows the Harker section (Z=1/3) of the difference Pattern of Os derivative of M1 crystals.
Figure 1B:
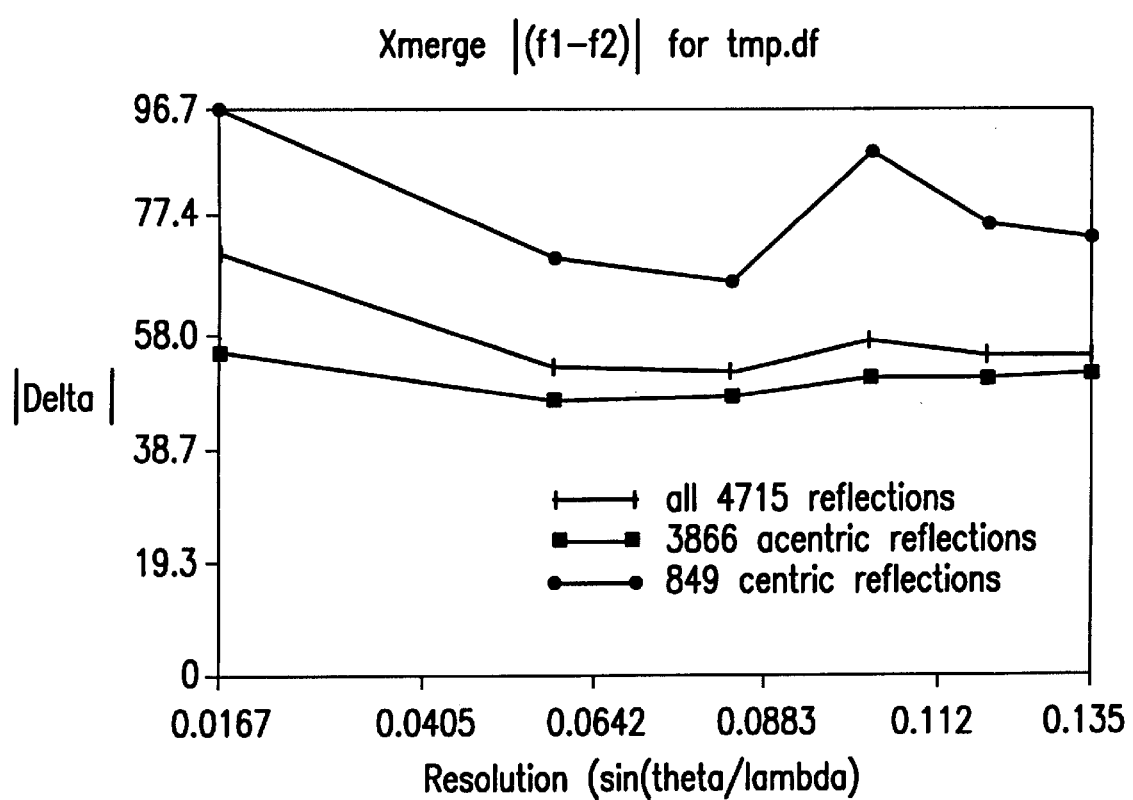
FIG. 1b shows the structure factor amplitude difference between native and Os derivative data sets versus resolution. From top to bottom, the curves are for all reflections, acentric reflections and centric reflections, respectively.
Figure 1C:
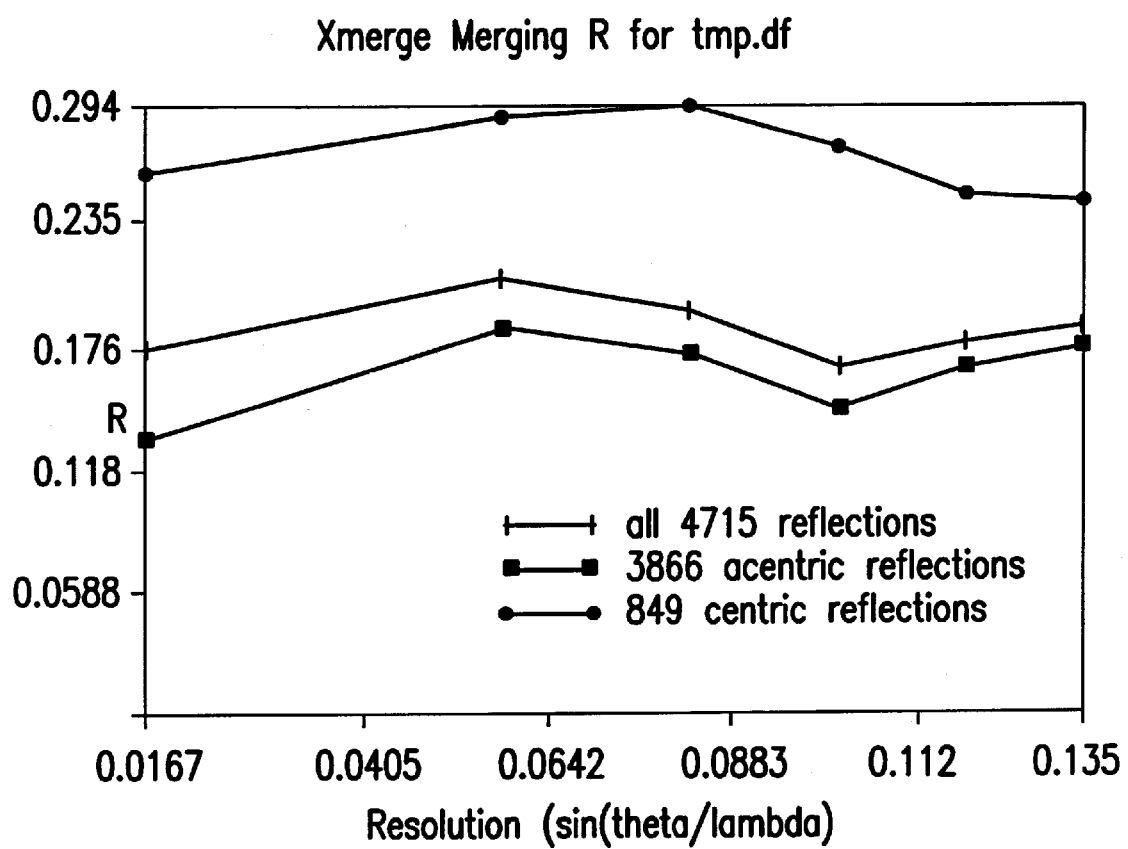
FIG. 1c shows the merging R-factor between native and Os derivative data sets versus resolution. From top to bottom, the curves are for all reflections, acentric reflections and centric reflections, respectively.

The present invention may be understood more readily by reference to the following detailed description of preferred embodiments of the invention and the Figures.

Before the present methods and structures are disclosed and described, it is to be understood that the terminology used herein is for the purpose of describing particular embodiments only and is not intended to be limiting. It must be noted that, as used in the specification and the appended claims, the singular forms "a," "an" and "the" include plural referents unless the context clearly dictates otherwise.

Throughout this application, where publications are referenced, the disclosures of these publications in their entireties are hereby incorporated by reference into this application in order to more fully describe the state of the art to which this invention pertains. Publications have been referenced herein by placing the number in parentheses. These publications are listed according to their respective numbers in the "Reference" section hereinbelow.

The present invention therefore provides a crystallized N-terminal domain of M1, wherein the N-terminal domain of M1 is crystallized such that the three dimensional structure of the crystallized N-terminal domain of M1 can be determined to a resolution of 2.1 Å or better, and wherein the three dimensional structure of the uncrystallized N-terminal domain of M1 cannot be determined to a resolution of 2.1 Å or better.

In a further embodiment, the present invention provides a method of extracting the M1 protein of influenza virus comprising stripping the membrane proteins from influenza virus, removing the stripped membrane proteins, thereby leaving the M1-RNP complex, and releasing M1 from the M1-RNP complex by suspending the complex in a solution comprising $NaH_2PO_4$, Benzamidine, and $NaN_3$. In a preferred embodiment, the solution has a pH of from about 3 to about 5, more preferably about 4.0. In a further embodiment, this method is extended to include purifying the released M1.

In yet another embodiment, the present invention provides a method of extracting the N-terminal domain of the M1 protein of influenza virus comprising stripping the membrane proteins from influenza virus, removing the stripped membrane proteins, thereby leaving the M1-RNP complex, releasing M1 from the M1-RNP complex by suspending the complex in a solution comprising $NaH_2PO_4$, Benzamidine, and $NaN_3$, purifying the released M1, concentrating the purified M1 to a concentration of from about 3 to about 20 mg/ml, more preferably from about 4 to about 10 mg/ml, and most preferably about 5 mg/ml, and after a period of time sufficient for the formation of an 18 kd protein fragment corresponding to the N-terminal domain of M1, collecting the 18 kd polypeptide corresponding to the N-terminal domain of M1. In a further embodiment, the time period is approximately fourteen days. In yet another embodiment, this method further comprises crystallizing the 18 kd polypeptide corresponding to the N-terminal domain of M1 to a resolution of less than about 2.1 Å, wherein the N-terminal domain of M1 is present at a concentration of about 3 to about 20 mg/ml, more preferably from about 4 to about 10 mg/ml and most preferably about 5 mg/ml, and the crystallization takes place at from 4 to 32° C., more preferably from 10 to 26° C., even more preferably at about 16 to about 24° C., and even more preferably 20° C., to thereby obtain crystals of space group $P3_121$ or $P3_221$. The crystals may have an approximate a=68.0 Å and approximate c=136.57 Å. The crystallization, in one embodiment, may occur using hanging drops and the vapor diffusion method. Alternatively, other crystallization methods may be used. For instance, a temperature variation may be used to produce crystals, or crystallization in space may be used to improve resolution. The crystallization, in another embodiment, may occur over 20% PEG 3350. In addition, other chemicals can be used in the place of PEG3350. For instance, organic chemicals (e.g. isopropanol), inorganic chemicals (e.g. $(NH_4)_2SO_4$, $NaH_2PO_4$), and other molecular weight PEG (from MPD to PEG20,000) may be used.

In yet another embodiment, the present invention provides a method for determining the three dimensional structure of the crystallized N-terminal domain of the M1 protein of influenza virus to a resolution of 2.1 Å or better comprising the steps of crystallizing the N-terminal domain of M1 to a resolution of less than about 2.1 Å, wherein the N-terminal domain of M1 is present at a concentration of about 3 to about 20 mg/ml, more preferably about 4 to about 10 mg/ml, even more preferably about 5 mg/ml and the crystallization takes place at from about 4 to about 32° C., more preferably from 10 to 26° C., even more preferably at about 16 to about 24° C., and even more preferably 20° C., to thereby obtain crystals of space group $P3_121$ or $P3_221$, and then analyzing the N-terminal domain of M1 to determine the three dimensional structure of the crystallized N-terminal domain of M1. In a preferred embodiment, the analyzing is by x-ray diffraction. The crystallization, in one embodiment, may occur over 20% PEG 3350. The crystallization, in one embodiment, may occur using hanging drops and the vapor diffusion method. Alternatively, other crystallization methods may be used. For instance, a temperature variation method may be used to produce crystals, or crystallization in outer space may be used to improve resolution.

In yet another embodiment, the present invention provides a crystallized N-terminal domain of M1 produced by the process described above.

In yet another embodiment, the present invention provides a method for designing an antiviral compound for the prevention or treatment of influenza virus infection, comprising evaluating the three dimensional structure of the crystallized N-terminal domain of M1 produced by crystallizing a purified N-terminal domain of M1 to a resolution of less than about 2.1 Å, wherein the N-terminal domain of M1 is present at a concentration of about 3 to about 20 mg/ml, more preferably about 4 to about 10 mg/ml, even more preferably about 5 mg/ml and the crystallization takes place at from about 4 to about 32° C., more preferably from 10 to 26° C., even more preferably at about 16 to about 24° C., and even more preferably 20° C., to thereby obtain crystals of space group $P3_121$ or $P3_221$, and synthesizing an antiviral compound based on the three-dimensional crystal structure of the crystallized N-terminal domain of M1, wherein the antiviral compound can be screened for having improved binding to M1. In a further embodiment, the antiviral compound is a peptide or polypeptide. The crystallization, in one embodiment, may occur using hanging drops and the vapor diffusion method. Alternatively, other crystallization methods may be used. For instance, a temperature variation may be used to produce crystals, or crystallization in space may be used to improve resolution.

In yet another embodiment, the present invention provides a purified N-terminal domain of M1. In a further embodiment, the invention provides that purified N-terminal domain of M1, comprising the amino acid sequence of SEQ. ID. NO. 1.

In yet another embodiment, the present invention provides a method for designing a candidate compound for screening for improved binding to or inhibition of influenza virus M1, comprising evaluating the three dimensional structure of the crystallized N-terminal domain of M1, and synthesizing a candidate binding compound based on the three-dimensional crystal structure of the crystallized N-terminal domain of M1 for improved binding to M1. In a further embodiment, the candidate compound is a peptide or polypeptide.

In yet another embodiment, the present invention provides the three-dimensional crystal structure of influenza virus protein M1 as set forth in the following table (see also FIG. 3):

```
CRYST1  67.170 67.170 135.300 90.00 90.00 120.00
SCALE1  0.014888  0.008595  0.000000  0.00000
SCALE2  0.000000  0.017194  0.000000  0.00000
SCALE3  0.000000  0.000000  0.007391  0.00000
ATOM  1  CB  SER 2 26.695 28.292 28.613 1.00 22.72
ATOM  2  OG  SER 2 26.267 29.344 29.471 1.00 24.24
ATOM  3  HG  SER 2 25.482 29.760 29.123 1.00  0.00
ATOM  4  C   SER 2 24.953 27.000 29.814 1.00 23.15
ATOM  5  O   SER 2 23.851 27.524 30.005 1.00 19.52
ATOM  6  HT1 SER 2 24.182 27.440 27.702 1.00  0.00
ATOM  7  HT2 SER 2 23.938 26.815 27.350 1.00  0.00
ATOM  8  N   SER 2 24.659 27.548 27.417 1.00 23.47
ATOM  9  HT3 SER 2 25.138 27.701 26.518 1.00  0.00
ATOM 10  CA  SER 2 25.657 27.183 28.472 1.00 23.46
ATOM 11  N   LEU 3 25.592 26.298 30.751 1.00 20.35
ATOM 12  H   LEU 3 26.490 25.933 30.576 1.00  0.00
ATOM 13  CA  LEU 3 24.979 26.088 32.062 1.00 17.46
ATOM 14  CB  LEU 3 25.781 25.075 32.898 1.00 19.31
ATOM 15  CG  LEU 3 25.374 24.879 34.379 1.00 19.41
ATOM 16  CD1 LEU 3 23.898 24.508 34.496 1.00 11.43
ATOM 17  CD2 LEU 3 26.260 23.802 35.023 1.00 18.23
ATOM 18  C   LEU 3 24.896 27.407 32.816 1.00 16.36
ATOM 19  O   LEU 3 23.860 27.768 33.371 1.00 15.18
ATOM 20  N   LEU 4 25.987 28.152 32.772 1.00 14.87
ATOM 21  H   LEU 4 26.761 27.849 32.251 1.00  0.00
ATOM 22  CA  LEU 4 26.062 29.401 33.484 1.00 15.53
ATOM 23  CB  LEU 4 27.461 29.999 33.343 1.00 15.39
ATOM 24  CG  LEU 4 28.520 29.077 33.971 1.00 13.82
ATOM 23  CD1 LEU 4 29.923 29.582 33.704 1.00 11.19
ATOM 26  CD2 LEU 4 28.271 28.971 35.466 1.00 17.28
ATOM 27  C   LEU 4 24.955 30.378 33.123 1.00 18.38
ATOM 28  O   LEU 4 24.512 31.149 33.973 1.00 18.56
ATOM 29  N   THR 5 24.466 30.323 31.890 1.00 19.71
ATOM 30  H   THR 5 24.836 26.692 31.523 1.00  0.00
ATOM 31  CA  THR 5 23.384 31.217 31.509 1.00 22.15
ATOM 32  CB  THR 5 23.228 31.339 29.983 1.00 26.89
ATOM 33  OG1 THR 5 22.981 30.054 29.406 1.00 34.75
ATOM 34  HG1 THR 5 23.680 29.463 29.624 1.00  0.00
ATOM 35  CG2 THR 5 24.488 31.891 29.383 1.00 23.91
ATOM 36  C   THR 5 22.084 30.763 32.179 1.00 20.11
ATOM 37  O   THR 5 21.277 31.602 32.588 1.00 21.65
ATOM 38  N   GLU 6 21.914 29.444 32.337 1.00 22.06
ATOM 39  H   GLU 6 22.587 28.831 31.988 1.00  0.00
ATOM 40  CA  GLU 6 20.736 28.883 33.013 1.00 17.17
ATOM 41  CB  GLU 6 20.752 27.364 32.989 1.00 19.28
ATOM 42  CG  GLU 6 20.517 26.705 31.662 1.00 23.44
ATOM 43  CD  GLU 6 20.397 25.192 31.809 1.00 26.59
ATOM 44  OE1 GLU 6 19.417 24.719 32.428 1.00 27.73
ATOM 45  OE2 GLU 6 21.300 24.474 31.333 1.00 30.79
ATOM 46  C   GLU 6 20.802 29.326 24.473 1.00 18.78
```

-continued

```
ATOM  47  O   GLU  6  19.805 27.786 35.043 1.00 18.66
ATOM  48  N   VAL  7  21.981 29.160 35.077 1.00 17.63
ATOM  49  H   VAL  7  22.719 28.754 34.576 1.00 0.00
ATOM  50  CA  VAL  7  22.207 29.570 36.463 1.00 15.32
ATOM  51  CB  VAL  7  23.703 29.406 36.877 1.00 12.34
ATOM  52  CG1 VAL  7  23.963 30.032 38.218 1.00 10.28
ATOM  53  CG2 VAL  7  24.076 27.957 36.927 1.00 10.34
ATOM  54  C   VAL  7  21.809 31.041 36.593 1.00 17.63
ATOM  55  O   VAL  7  21.111 31.415 37.534 1.00 17.77
ATOM  56  N   GLU  8  22.200 31.856 35.611 1.00 16.16
ATOM  57  H   GLU  8  22.713 31.489 34.861 1.00 0.00
ATOM  58  CA  GLU  8  21.882 33.279 35.635 1.00 17.04
ATOM  59  CB  GLU  8  22.546 34.032 34.483 1.00 18.28
ATOM  60  CG  GLU  8  22.355 35.540 34.622 1.00 18.53
ATOM  61  CD  GLU  8  22.846 36.345 33.442 1.00 21.27
ATOM  62  OE1 GLU  8  23.311 35.767 32.450 1.00 19.23
ATOM  63  OE2 GLU  8  22.771 37.583 33.512 1.00 28.23
ATOM  64  C   GLU  8  20.395 33.599 35.633 1.00 13.86
ATOM  65  O   GLU  8  19.967 34.512 36.320 1.00 14.68
ATOM  66  N   THR  9  19.611 32.876 34.851 1.00 13.26
ATOM  67  H   THR  9  19.988 32.164 34.294 1.00 0.00
ATOM  68  CA  THR  9  18.179 33.148 34.813 1.00 19.26
ATOM  69  CB  THR  9  17.437 32.302 33.713 1.00 16.47
ATOM  70  OG1 THR  9  17.316 30.939 34.137 1.00 30.32
ATOM  71  HG1 THR  9  18.193 30.560 34.274 1.00 0.00
ATOM  72  CG2 THR  9  18.219 32.307 32.421 1.00 11.87
ATOM  73  C   THR  9  17.584 32.895 32.216 1.00 19.01
ATOM  74  O   THR  9  16.838 33.731 36.742 1.00 19.66
ATOM  75  N   TYR 10  17.948 31.768 36.831 1.00 17.18
ATOM  76  H   TYR 10  18.569 31.150 36.382 1.00 0.00
ATOM  77  CA  TYR 10  17.460 31.438 38.167 1.00 15.38
ATOM  78  CB  TYR 10  17.984 30.087 38.617 1.00 15.57
ATOM  79  CG  TYR 10  17.205 28.941 38.055 1.00 13.50
ATOM  80  CD1 TYR 10  17.708 28.193 37.003 1.00 11.74
ATOM  81  CE1 TYR 10  16.972 27.154 36.440 1.00 16.51
ATOM  82  CD2 TYR 10  15.943 28.626 38.552 1.00 17.02
ATOM  83  CE2 TYR 10  15.193 27.589 38.004 1.00 19.98
ATOM  84  CZ  TYR 10  15.710 26.856 36.942 1.00 21.89
ATOM  85  OH  TYR 10  14.955 25.847 36.362 1.00 22.73
ATOM  86  HH  TYR 10  14.113 25.788 36.803 1.00 0.00
ATOM  87  C   TYR 10  17.856 32.466 39.197 1.00 13.97
ATOM  88  O   TYR 10  17.067 32.822 40.068 1.00 16.11
ATOM  89  N   VAL 11  19.085 32.947 39.098 1.00 14.44
ATOM  90  H   VAL 11  19.671 32.632 38.374 1.00 0.00
ATOM  91  CA  VAL 11  19.583 33.923 40.046 1.00 13.86
ATOM  92  CB  VAL 11  21.097 34.098 39.909 1.00 17.09
ATOM  93  CG1 VAL 11  21.569 35.203 40.816 1.00 16.86
ATOM  94  CG2 VAL 11  21.804 32.790 40.243 1.00 15.07
ATOM  95  C   VAL 11  18.881 35.256 39.879 1.00 16.92
ATOM  96  O   VAL 11  18.487 35.886 40.860 1.00 15.65
ATOM  97  N   LEU 12  18.693 35.666 38.627 1.00 18.12
ATOM  98  H   LEU 12  19.004 35.103 37.887 1.00 0.00
ATOM  99  CA  LEU 12  18.030 36.927 38.331 1.00 16.98
ATOM 100  CB  LEU 12  18.198 37.312 36.854 1.00 14.73
ATOM 101  CG  LEU 12  19.625 37.688 36.466 1.00 13.13
ATOM 102  CD1 LEU 12  19.624 38.200 35.069 1.00 15.19
ATOM 103  CD2 LEU 12  20.180 38.764 37.406 1.00 13.68
ATOM 104  C   LEU 12  16.562 36.886 38.692 1.00 15.90
ATOM 105  O   LEU 12  16.009 37.895 39.118 1.00 20.74
ATOM 106  N   SER 13  15.953 35.709 38.599 1.00 16.34
ATOM 107  H   SER 13  16.462 34.926 38.318 1.00 0.00
ATOM 108  CA  SER 13  14.539 35.558 38.906 1.00 16.50
ATOM 109  CB  SER 13  14.089 34.111 38.690 1.00 19.68
ATOM 110  OG  SER 13  14.485 33.248 39.752 1.00 20.41
ATOM 111  HG  SER 13  15.416 33.255 39.842 1.00 0.00
ATOM 112  C   SER 13  14.135 36.034 40.306 1.00 19.26
ATOM 113  O   SER 13  12.968 36.301 40.552 1.00 21.35
ATOM 114  N   ILE 14  15.087 36.152 41.223 1.00 20.06
ATOM 115  H   ILE 14  16.017 35.952 40.997 1.00 0.00
ATOM 116  CA  ILE 14  14.736 36.601 42.555 1.00 16.72
ATOM 117  CB  ILE 14  15.384 35.704 43.672 1.00 17.84
ATOM 118  CG2 ILE 14  14.876 34.283 43.560 1.00 13.91
ATOM 119  CG1 ILE 14  16.909 35.761 43.609 1.00 19.30
ATOM 120  CD1 ILE 14  17.602 35.203 44.827 1.00 14.33
ATOM 121  C   ILE 14  15.019 38.078 42.794 1.00 15.86
ATOM 122  O   ILE 14  14.594 38.629 43.799 1.00 15.25
ATOM 123  N   ILE 15  15.729 38.734 41.883 1.00 21.19
ATOM 124  H   ILE 15  16.019 38.276 41.067 1.00 0.00
ATOM 125  CA  ILE 15  16.050 40.154 42.060 1.00 23.81
ATOM 126  CB  ILE 15  17.309 40.584 41.266 1.00 24.86
ATOM 127  CG2 ILE 15  17.785 41.967 41.749 1.00 26.57
ATOM 128  CG1 ILE 15  18.437 39.556 41.400 1.00 25.02
ATOM 129  CD1 ILE 15  18.931 39.359 42.800 1.00 31.18
ATOM 130  C   ILE 15  14.907 41.038 41.559 1.00 28.51
ATOM 131  O   ILE 15  14.289 40.739 40.542 1.00 30.32
ATOM 132  N   PRO 16  14.567 42.104 42.301 1.00 31.91
ATOM 133  CD  PRO 16  14.958 42.504 43.666 1.00 33.48
ATOM 134  CA  PRO 16  13.477 42.946 41.793 1.00 34.20
ATOM 135  CB  PRO 16  13.204 43.898 42.968 1.00 32.63
ATOM 136  CG  PRO 16  14.516 43.939 43.715 1.00 35.14
ATOM 137  C   PRO 16  13.924 43.689 40.519 1.00 32.66
ATOM 138  O   PRO 16  15.072 44.139 40.425 1.00 30.48
ATOM 139  N   SER 17  13.035 43.769 39.529 1.00 34.68
ATOM 140  H   SER 17  12.158 43.369 39.649 1.00 0.00
ATOM 141  CA  SER 17  13.341 44.449 38.264 1.00 37.99
ATOM 142  CB  SER 17  12.143 44.377 37.311 1.00 39.60
ATOM 143  OG  SER 17  11.717 43.032 37.120 1.00 47.68
ATOM 144  HG  SER 17  11.462 42.649 37.957 1.00 0.00
ATOM 145  C   SER 17  13.737 45.908 38.498 1.00 38.06
ATOM 146  O   SER 17  13.101 46.623 39.273 1.00 38.78
ATOM 147  N   GLY 18  14.807 46.339 37.842 1.00 38.35
ATOM 148  H   GLY 18  15.299 45.731 37.253 1.00 0.00
ATOM 149  CA  GLY 18  15.271 47.701 38.006 1.00 34.14
ATOM 150  C   GLY 18  16.717 47.805 37.585 1.00 34.09
ATOM 151  O   GLY 18  17.293 46.822 37.117 1.00 36.02
ATOM 152  N   PRO 19  17.347 48.969 37.789 1.00 34.46
ATOM 153  CD  PRO 19  16.738 50.089 38.528 1.00 35.80
ATOM 154  CA  PRO 19  18.743 49.266 37.447 1.00 33.74
ATOM 155  CB  PRO 19  18.889 50.724 37.879 1.00 36.63
ATOM 156  CG  PRO 19  17.946 50.819 39.056 1.00 37.03
ATOM 157  C   PRO 19  19.734 48.374 38.187 1.00 35.10
ATOM 158  O   PRO 19  20.744 47.958 37.621 1.00 35.49
ATOM 159  N   LEU 20  19.437 48.094 39.456 1.00 36.74
ATOM 160  H   LEU 20  18.629 48.478 39.844 1.00 0.00
ATOM 161  CA  LEU 20  20.281 47.245 40.301 1.00 32.44
ATOM 162  CB  LEU 20  19.670 47.111 41.703 1.00 32.72
ATOM 163  CG  LEU 20  20.579 47.103 42.937 1.00 33.61
ATOM 164  CD1 LEU 20  19.784 46.663 44.144 1.00 31.90
ATOM 165  CD2 LEU 20  21.760 46.182 42.732 1.00 33.95
ATOM 166  C   LEU 20  20.353 45.869 39.646 1.00 28.85
ATOM 167  O   LEU 20  21.430 45.284 39.507 1.00 30.02
ATOM 168  N   LYS 21  16.198 45.378 39.216 1.00 23.41
ATOM 169  H   LYS 21  18.377 45.891 39.336 1.00 0.00
ATOM 170  CA  LYS 21  19.125 44.088 38.569 1.00 21.47
ATOM 171  CB  LYS 21  17.669 43.736 38.289 1.00 16.66
ATOM 172  CG  LYS 21  17.433 42.316 37.808 1.00 14.92
ATOM 173  CD  LYS 21  15.961 42.053 37.717 1.00 10.55
ATOM 174  CE  LYS 21  15.681 40.611 37.453 1.00 15.68
ATOM 175  NZ  LYS 21  14.257 40.283 37.718 1.00 16.95
ATOM 176  HZ1 LYS 21  13.651 40.851 37.094 1.00 0.00
ATOM 177  HZ2 LYS 21  14.033 40.481 38.706 1.00 0.00
ATOM 178  HZ3 LYS 21  14.100 39.270 37.520 1.00 0.00
ATOM 179  C   LYS 21  19.966 44.123 37.276 1.00 25.28
ATOM 180  O   LYS 21  20.514 43.093 36.841 1.00 26.00
ATOM 181  N   ALA 22  22.107 45.309 36.688 1.00 19.79
ATOM 182  H   ALA 22  19.661 46.088 37.066 1.00 0.00
ATOM 183  CA  ALA 22  20.910 45.452 35.481 1.00 20.93
ATOM 184  CB  ALA 22  20.651 46.796 34.812 1.00 19.38
ATOM 185  C   ALA 22  22.374 45.331 35.868 1.00 17.57
ATOM 186  O   ALA 22  23.144 44.658 35.194 1.00 22.09
ATOM 187  N   GLU 23  22.761 45.992 36.950 1.00 20.96
ATOM 188  H   GLU 23  22.111 46.531 37.443 1.00 0.00
ATOM 189  CA  GLU 23  24.139 45.933 37.427 1.00 23.81
ATOM 190  CB  GLU 23  24.305 46.812 38.648 1.00 25.77
ATOM 191  CG  GLU 23  24.154 48.273 38.351 1.00 33.59
ATOM 192  CD  GLU 23  23.522 49.014 39.496 1.00 38.59
ATOM 193  OE1 GLU 23  22.567 49.780 39.247 1.00 44.81
ATOM 194  OE2 GLU 23  23.964 48.818 40.650 1.00 49.94
ATOM 195  C   GLU 23  24.549 44.509 37.781 1.00 25.74
ATOM 196  O   GLU 23  25.607 44.047 37.365 1.00 29.16
ATOM 197  N   ILE 24  23.723 43.832 38.577 1.00 23.09
ATOM 263  CB  ASP 30  31.728 40.580 33.792 1.00 23.63
ATOM 264  CG  ASP 30  31.319 41.686 32.816 1.00 26.58
ATOM 265  OD1 ASP 30  31.497 42.873 33.158 1.00 27.51
ATOM 266  OD2 ASP 30  30.820 41.377 31.713 1.00 25.65
ATOM 267  C   ASP 30  32.192 38.125 34.037 1.00 20.66
ATOM 268  O   ASP 30  33.245 37.692 33.550 1.00 21.87
ATOM 269  N   VAL 31  31.741 37.701 35.221 1.00 16.91
```

-continued

```
ATOM   198  H    ILE  24   22.928  44.282  38.918  1.00   0.00
ATOM   199  CA   ILE  24   23.974  42.447  38.978  1.00  20.14
ATOM   200  CB   ILE  24   22.815  41.924  39.877  1.00  21.29
ATOM   201  CG2  ILE  24   22.876  40.402  40.025  1.00  19.58
ATOM   202  CG1  ILE  24   22.847  42.644  41.234  1.00  23.57
ATOM   203  CD1  ILE  24   21.648  42.367  42.133  1.00  21.62
ATOM   204  C    ILE  24   24.154  41.535  37.752  1.00  17.46
ATOM   205  O    ILE  24   25.147  40.813  37.664  1.00  20.13
ATOM   206  N    ALA  25   23.230  41.611  36.794  1.00  16.90
ATOM   207  H    ALA  25   22.478  42.235  36.916  1.00   0.00
ATOM   208  CA   ALA  25   23.288  40.803  35.572  1.00  18.54
ATOM   209  CB   ALA  25   22.120  41.113  34.671  1.00  17.95
ATOM   210  C    ALA  25   24.584  40.994  34.804  1.00  18.47
ATOM   211  O    ALA  25   25.140  40.038  34.273  1.00  19.08
ATOM   212  N    GLN  26   25.038  42.240  34.716  1.00  22.49
ATOM   213  H    GLN  26   24.526  42.964  35.143  1.00   0.00
ATOM   214  CA   GLN  26   26.271  42.564  34.025  1.00  19.66
ATOM   215  CB   GLN  26   26.467  44.072  33.982  1.00  23.24
ATOM   216  CG   GLN  26   27.762  44.518  33.307  1.00  32.72
ATOM   217  CD   GLN  26   27.870  44.059  31.866  1.00  39.27
ATOM   218  OE1  GLN  26   28.827  43.383  31.493  1.00  44.74
ATOM   219  NE2  GLN  26   26.898  44.441  31.041  1.00  45.96
ATOM   220  HE21 GLN  26   26.167  44.993  31.384  1.00   0.00
ATOM   221  HE22 GLN  26   26.952  44.147  30.111  1.00   0.00
ATOM   222  C    GLN  26   27.441  41.932  34.747  1.00  19.36
ATOM   223  O    GLN  26   28.319  41.349  34.109  1.00  20.52
ATOM   224  N    ARG  27   27.464  42.067  36.073  1.00  17.79
ATOM   225  H    ARG  27   26.739  42.558  36.517  1.00   0.00
ATOM   226  CA   ARG  27   28.535  41.492  36.905  1.00  18.48
ATOM   227  CB   ARG  27   28.359  41.861  38.384  1.00  19.92
ATOM   228  CG   ARG  27   28.698  43.315  38.643  1.00  22.05
ATOM   229  CD   ARG  27   28.146  43.828  39.942  1.00  28.72
ATOM   230  NE   ARG  27   28.161  45.289  39.964  1.00  33.96
ATOM   231  HE   ARG  27   27.384  45.753  39.603  1.00   0.00
ATOM   232  CZ   ARG  27   29.158  46.030  40.440  1.00  40.38
ATOM   233  NH1  ARG  27   30.250  45.459  40.951  1.00  43.63
ATOM   234  HH11 ARG  27   30.337  44.463  40.979  1.00   0.00
ATOM   235  HH12 ARG  27   30.997  46.029  41.306  1.00   0.00
ATOM   236  NH2  ARG  27   29.058  47.354  40.414  1.00  39.68
ATOM   237  HH21 ARG  27   28.238  47.784  40.045  1.00   0.00
ATOM   238  HH22 ARG  27   29.803  47.918  40.775  1.00   0.00
ATOM   239  C    ARG  27   28.595  39.988  36.754  1.00  17.75
ATOM   240  O    ARG  27   29.681  39.431  36.571  1.00  22.76
ATOM   241  N    LEU  28   27.433  39.340  36.783  1.00  13.74
ATOM   242  H    LEU  28   26.606  39.845  36.910  1.00   0.00
ATOM   243  CA   LEU  28   27.381  37.895  36.629  1.00  16.11
ATOM   244  CB   LEU  28   25.952  37.368  36.757  1.00  13.10
ATOM   245  CG   LEU  28   25.339  37.219  38.151  1.00  17.27
ATOM   246  CD1  LEU  28   23.847  36.918  38.035  1.00  14.43
ATOM   247  CD2  LEU  28   26.039  36.111  38.911  1.00  14.44
ATOM   248  C    LEU  28   27.961  37.494  35.287  1.00  17.24
ATOM   249  O    LEU  28   28.904  36.704  35.234  1.00  19.78
ATOM   250  N    GLU  29   27.423  38.078  34.214  1.00  19.33
ATOM   251  H    GLU  29   26.702  38.725  34.347  1.00   0.00
ATOM   252  CA   GLU  29   27.862  37.795  32.850  1.00  18.96
ATOM   253  CB   GLU  29   27.115  38.689  31.859  1.00  18.98
ATOM   254  CG   GLU  29   25.660  38.295  31.684  1.00  23.80
ATOM   255  CD   GLU  29   24.758  39.443  31.245  1.00  28.55
ATOM   256  OE1  GLU  29   25.183  40.613  31.316  1.00  35.86
ATOM   257  OE2  GLU  29   23.601  39.179  30.852  1.00  31.38
ATOM   258  C    GLU  29   29.372  37.936  32.686  1.00  19.46
ATOM   259  O    GLU  29   30.010  37.104  32.029  1.00  18.46
ATOM   260  N    ASP  30   29.945  38.959  33.316  1.00  19.80
ATOM   261  H    ASP  30   29.379  39.584  33.819  1.00   0.00
ATOM   262  CA   ASP  30   31.388  39.183  33.274  1.00  19.46
ATOM   335  CA   ASP  38   38.027  41.426  42.862  1.00  30.75
ATOM   336  CB   ASP  38   38.503  42.823  43.230  1.00  31.44
ATOM   337  CG   ASP  38   39.239  42.869  44.550  1.00  33.99
ATOM   338  OD1  ASP  38   39.127  41.910  45.349  1.00  32.32
ATOM   339  OD2  ASP  38   39.942  43.872  44.790  1.00  36.56
ATOM   340  C    ASP  38   36.796  41.057  43.681  1.00  26.79
ATOM   341  O    ASP  38   35.874  41.870  43.844  1.00  22.79
ATOM   342  N    LEU  39   36.772  39.814  44.158  1.00  22.33
ATOM   343  H    LEU  39   37.499  39.191  43.943  1.00   0.00
ATOM   344  CA   LEU  39   35.661  39.320  44.964  1.00  18.89
ATOM   345  CB   LEU  39   35.921  37.864  45.397  1.00  13.81
ATOM   346  CG   LEU  39   34.889  37.153  46.291  1.00  11.86
ATOM   347  CD1  LEU  39   33.552  37.013  45.571  1.00  11.90
ATOM   348  CD2  LEU  39   35.410  35.805  46.694  1.00  10.47
ATOM   270  H    VAL  31   30.922  38.070  35.613  1.00   0.00
ATOM   271  CA   VAL  31   32.508  36.669  35.917  1.00  16.50
ATOM   272  CB   VAL  31   32.073  36.385  37.405  1.00  18.56
ATOM   273  CG1  VAL  31   32.236  37.621  38.246  1.00  22.25
ATOM   274  CG2  VAL  31   30.662  35.883  37.489  1.00  20.05
ATOM   275  C    VAL  31   32.370  35.399  35.118  1.00  14.17
ATOM   276  O    VAL  31   33.360  34.704  34.894  1.00  14.10
ATOM   277  N    PHE  32   31.163  35.155  34.604  1.00  10.67
ATOM   278  H    PHE  32   30.444  35.785  34.763  1.00   0.00
ATOM   279  CA   PHE  32   30.889  33.949  33.824  1.00  17.93
ATOM   280  CB   PHE  32   29.412  33.860  33.424  1.00  16.59
ATOM   281  CG   PHE  32   28.483  33.579  34.568  1.00  20.17
ATOM   282  CD1  PHE  32   27.108  33.608  34.378  1.00  20.46
ATOM   283  CD2  PHE  32   28.973  33.288  35.830  1.00  20.31
ATOM   284  CE1  PHE  32   26.240  33.354  35.424  1.00  21.08
ATOM   285  CE2  PHE  32   28.106  33.032  36.887  1.00  24.55
ATOM   286  CZ   PHE  32   26.735  33.065  36.681  1.00  21.99
ATOM   287  C    PHE  32   31.759  33.849  32.582  1.00  21.13
ATOM   288  O    PHE  32   32.179  32.752  32.201  1.00  20.61
ATOM   289  N    ALA  33   32.023  35.003  31.968  1.00  21.59
ATOM   290  H    ALA  33   31.637  35.820  32.334  1.00   0.00
ATOM   291  CA   ALA  33   32.842  35.081  30.775  1.00  21.27
ATOM   292  CB   ALA  33   32.540  36.349  30.019  1.00  21.72
ATOM   293  C    ALA  33   34.314  35.009  31.138  1.00  24.38
ATOM   294  O    ALA  33   35.182  35.033  30.272  1.00  25.88
ATOM   295  N    GLY  34   34.601  35.007  32.427  1.00  24.57
ATOM   296  H    GLY  34   33.895  35.089  33.093  1.00   0.00
ATOM   297  CA   GLY  34   35.974  34.881  32.840  1.00  30.55
ATOM   298  C    GLY  34   36.733  36.101  33.296  1.00  34.76
ATOM   299  O    GLY  34   37.888  35.953  33.696  1.00  36.73
ATOM   300  N    LYS  35   36.146  37.292  33.237  1.00  40.49
ATOM   301  H    LYS  35   35.233  37.373  32.882  1.00   0.00
ATOM   302  CA   LYS  35   36.877  38.481  33.706  1.00  47.46
ATOM   303  CB   LYS  35   36.123  39.777  33.374  1.00  46.18
ATOM   304  CG   LYS  35   35.330  39.758  32.073  1.00  47.13
ATOM   305  CD   LYS  35   36.198  39.538  30.855  1.00  50.64
ATOM   306  CE   LYS  35   35.364  39.660  29.592  1.00  50.86
ATOM   307  NZ   LYS  35   34.644  40.963  29.571  1.00  48.30
ATOM   308  HZ1  LYS  35   35.348  41.744  29.595  1.00   0.00
ATOM   309  HZ2  LYS  35   34.027  41.041  30.395  1.00   0.00
ATOM   310  HZ3  LYS  35   34.092  41.044  28.696  1.00   0.00
ATOM   311  C    LYS  35   37.075  38.374  35.237  1.00  51.34
ATOM   312  O    LYS  35   36.108  38.526  36.009  1.00  50.56
ATOM   313  N    ASN  36   38.305  38.057  35.668  1.00  55.49
ATOM   314  H    ASN  36   39.008  37.883  35.012  1.00   0.00
ATOM   315  CA   ASN  36   38.605  37.926  37.102  1.00  57.00
ATOM   316  CB   ASN  36   40.051  37.476  37.404  1.00  57.80
ATOM   317  CG   ASN  36   40.297  37.232  38.928  1.00  59.89
ATOM   318  OD1  ASN  36   39.374  36.893  39.690  1.00  53.37
ATOM   319  ND2  ASN  36   41.546  37.390  39.357  1.00  58.78
ATOM   320  HD21 ASN  36   42.246  37.643  38.738  1.00   0.00
ATOM   321  HD22 ASN  36   41.720  37.237  40.314  1.00   0.00
ATOM   322  C    ASN  36   38.338  39.233  37.798  1.00  54.68
ATOM   323  O    ASN  36   38.985  40.251  37.528  1.00  55.96
ATOM   324  N    THR  37   37.341  39.201  38.664  1.00  51.87
ATOM   325  H    THR  37   36.859  38.364  38.824  1.00   0.00
ATOM   326  CA   THR  37   36.972  40.379  39.393  1.00  48.77
ATOM   327  CB   THR  37   35.446  40.580  39.358  1.00  51.89
ATOM   328  OG1  THR  37   34.951  40.258  38.047  1.00  52.86
ATOM   329  HG1  THR  37   35.154  39.344  37.827  1.00   0.00
ATOM   330  CG2  THR  37   35.095  42.039  39.677  1.00  54.40
ATOM   331  C    THR  37   37.469  40.246  40.823  1.00  43.38
ATOM   332  O    THR  37   37.812  39.152  41.285  1.00  44.42
ATOM   333  N    ASP  38   37.604  41.386  41.484  1.00  37.50
ATOM   334  H    ASP  38   37.411  42.224  41.013  1.00   0.00
ATOM   407  HE1  TRP  45   27.028  49.009  42.977  1.00   0.00
ATOM   408  CZ2  TRP  45   25.715  46.613  42.153  1.00  15.30
ATOM   409  CZ3  TRP  45   26.092  44.275  42.712  1.00  22.34
ATOM   410  CH2  TRP  45   25.380  45.291  42.022  1.00  22.84
ATOM   411  C    TRP  45   27.816  45.516  47.200  1.00  20.98
ATOM   412  O    TRP  45   26.875  46.202  47.580  1.00  22.52
ATOM   413  N    LEU  46   27.740  44.197  47.134  1.00  20.45
ATOM   414  H    LEU  46   28.526  43.684  46.854  1.00   0.00
ATOM   415  CA   LEU  46   26.505  43.494  47.456  1.00  19.83
ATOM   416  CB   LEU  46   26.717  41.988  47.349  1.00  20.94
ATOM   417  CG   LEU  46   26.554  41.283  46.020  1.00  24.92
ATOM   418  CD1  LEU  46   26.923  39.833  46.239  1.00  24.33
ATOM   419  CD2  LEU  46   25.113  41.417  45.542  1.00  24.55
ATOM   420  C    LEU  46   26.039  43.788  48.879  1.00  18.43
```

-continued

| | | | | | |
|---|---|---|---|---|---|
ATOM 349 C LEU 39 35.444 40.225 46.183 1.00 18.68
ATOM 350 O LEU 39 34.308 40.498 46.565 1.00 21.12
ATOM 351 N GLU 40 36.533 40.726 46.753 1.00 19.42
ATOM 352 H GLU 40 37.410 40.497 46.396 1.00 0.00
ATOM 353 CA GLU 40 36.451 41.591 47.921 1.00 23.60
ATOM 354 CB GLU 40 37.843 42.023 48.366 1.00 27.21
ATOM 355 CG GLU 40 37.842 42.938 49.584 1.00 44.74
ATOM 356 CD GLU 40 39.230 43.454 49.927 1.00 53.90
ATOM 357 OE1 GLU 40 39.937 42.784 50.718 1.00 59.32
ATOM 358 OE2 GLU 40 39.613 44.529 49.402 1.00 60.65
ATOM 359 C GLU 40 35.623 42.814 47.595 1.00 24.31
ATOM 360 O GLU 40 34.833 43.278 48.412 1.00 23.52
ATOM 361 N VAL 41 35.817 43.333 46.389 1.00 26.71
ATOM 362 H VAL 41 36.456 42.906 45.793 1.00 0.00
ATOM 363 CA VAL 41 35.092 44.510 45.918 1.00 30.42
ATOM 364 CB VAL 41 35.772 45.094 44.648 1.00 35.26
ATOM 365 CG1 VAL 41 34.909 46.192 44.025 1.00 38.11
ATOM 366 CG2 VAL 41 37.153 45.640 45.004 1.00 32.38
ATOM 367 C VAL 41 33.629 44.159 45.636 1.00 24.47
ATOM 368 O VAL 41 32.714 44.851 46.074 1.00 26.21
ATOM 369 N LEU 42 33.424 43.060 44.928 1.00 24.20
ATOM 370 H LEU 42 34.197 42.554 44.617 1.00 0.00
ATOM 371 CA LEU 42 32.096 42.576 44.588 1.00 20.29
ATOM 372 CB LEU 42 32.219 41.216 43.904 1.00 24.03
ATOM 373 CG LEU 42 31.611 41.062 42.525 1.00 26.40
ATOM 374 CD1 LEU 42 31.964 39.715 41.965 1.00 25.94
ATOM 375 CD2 LEU 42 30.116 41.247 42.629 1.00 32.20
ATOM 376 C LEU 42 31.261 42.414 45.846 1.00 17.94
ATOM 377 O LEU 42 30.172 42.979 45.961 1.00 18.69
ATOM 378 N MET 43 31.801 41.656 46.797 1.00 15.65
ATOM 379 H MET 43 32.682 41.284 46.645 1.00 0.00
ATOM 380 CA MET 43 31.133 41.364 48.064 1.00 17.70
ATOM 381 CB MET 43 31.999 40.434 48.918 1.00 15.00
ATOM 382 CG MET 43 32.195 39.058 48.311 1.00 15.30
ATOM 383 SD MET 43 30.702 38.017 48.215 1.00 17.90
ATOM 384 CE MET 43 30.226 38.195 46.576 1.00 22.51
ATOM 385 C MET 43 30.722 42.593 48.866 1.00 16.98
ATOM 386 O MET 43 29.612 42.649 49.382 1.00 17.31
ATOM 387 N GLU 44 31.612 43.575 48.955 1.00 20.26
ATOM 388 H GLU 44 32.483 43.463 48.514 1.00 0.00
ATOM 389 CA GLU 44 31.343 44.813 49.671 1.00 23.74
ATOM 390 CB GLU 44 32.612 45.681 49.752 1.00 25.41
ATOM 391 CG GLU 44 32.467 46.983 50.563 1.00 31.31
ATOM 392 CD GLU 44 31.832 46.774 51.941 1.00 35.92
ATOM 393 OE1 GLU 44 32.195 45.800 52.643 1.00 36.04
ATOM 394 OE2 GLU 44 30.950 47.583 52.314 1.00 39.72
ATOM 395 C GLU 44 30.201 45.561 48.993 1.00 24.64
ATOM 396 O GLU 44 29.306 46.122 49.658 1.00 24.29
ATOM 397 N TRP 45 30.208 45.510 47.662 1.00 22.97
ATOM 398 H TRP 45 30.934 45.032 47.207 1.00 0.00
ATOM 399 CA TRP 45 29.176 46.150 46.857 1.00 23.59
ATOM 400 CB TRP 45 29.517 46.000 45.367 1.00 20.89
ATOM 401 CG TRP 45 28.525 46.618 44.456 1.00 20.23
ATOM 402 CD2 TRP 45 27.518 45.936 43.700 1.00 19.85
ATOM 403 CE2 TRP 45 26.785 46.926 42.996 1.00 20.46
ATOM 404 CE3 TRP 45 27.155 45.588 43.549 1.00 17.73
ATOM 405 CD1 TRP 45 28.378 47.946 44.189 1.00 18.89
ATOM 406 NE1 TRP 45 27.335 48.138 43.316 1.00 18.48
ATOM 479 CA LEU 52 17.992 43.695 48.323 1.00 26.68
ATOM 480 CB LEU 52 19.393 43.333 47.818 1.00 21.97
ATOM 481 CG LEU 52 19.742 43.661 46.367 1.00 20.21
ATOM 482 CD1 LEU 52 21.136 43.140 46.057 1.00 19.41
ATOM 483 CD2 LEU 52 18.727 43.041 45.428 1.00 20.03
ATOM 484 C LEU 52 17.801 43.115 49.716 1.00 25.06
ATOM 485 O LEU 52 18.287 43.664 50.705 1.00 23.98
ATOM 486 N SER 53 17.066 42.018 49.798 1.00 23.37
ATOM 487 H SER 53 16.651 41.647 48.993 1.00 0.00
ATOM 488 CA SER 53 16.844 41.377 51.080 1.00 23.35
ATOM 489 CB SER 53 15.750 40.308 50.956 1.00 25.31
ATOM 490 OG SER 53 16.201 39.183 50.210 1.00 24.71
ATOM 491 HG SER 53 16.954 38.795 50.638 1.00 0.00
ATOM 492 C SER 53 18.137 40.693 51.482 1.00 20.63
ATOM 493 O SER 53 18.962 40.362 50.622 1.00 21.92
ATOM 494 N PRO 54 18.326 40.460 52.789 1.00 20.64
ATOM 495 CD PRO 54 17.556 41.025 53.910 1.00 20.93
ATOM 496 CA PRO 54 19.534 39.788 53.279 1.00 16.81
ATOM 497 CB PRO 54 19.295 39.751 54.780 1.00 20.34
ATOM 498 CG PRO 54 18.574 41.048 55.017 1.00 22.23
ATOM 499 C PRO 54 19.663 38.372 52.678 1.00 13.03
ATOM 421 O LEU 46 24.865 44.073 49.128 1.00 20.04
ATOM 422 N LYS 47 26.963 43.631 49.812 1.00 15.42
ATOM 423 H LYS 47 27.866 43.367 49.542 1.00 0.00
ATOM 424 CA LYS 47 26.681 43.841 51.200 1.00 15.05
ATOM 425 CB LYS 47 27.967 43.847 51.999 1.00 16.25
ATOM 426 CG LYS 47 27.679 44.043 53.455 1.00 20.69
ATOM 427 CD LYS 47 28.919 44.064 54.292 1.00 28.23
ATOM 428 CE LYS 47 28.513 44.194 55.746 1.00 30.70
ATOM 429 NZ LYS 47 29.654 44.501 56.646 1.00 35.92
ATOM 430 HZ1 LYS 47 30.090 45.401 56.366 1.00 0.00
ATOM 431 HZ2 LYS 47 30.354 43.736 56.590 1.00 0.00
ATOM 432 HZ1 LYS 47 29.306 44.578 57.627 1.00 0.00
ATOM 433 C LYS 47 25.963 45.158 51.408 1.00 20.22
ATOM 434 O LYS 47 24.957 45.207 52.096 1.00 18.90
ATOM 435 N THR 48 26.489 46.216 50.793 1.00 25.04
ATOM 436 H THR 48 27.289 46.088 50.235 1.00 0.00
ATOM 437 CA THR 48 25.927 47.561 50.904 1.00 23.95
ATOM 438 CB THR 48 27.028 48.613 50.714 1.00 20.88
ATOM 439 OG1 THR 48 27.693 48.387 49.468 1.00 25.10
ATOM 440 HG1 THR 48 28.095 47.517 49.462 1.00 0.00
ATOM 441 CG2 THR 48 28.042 48.521 51.822 1.00 19.81
ATOM 442 C THR 48 24.747 47.912 49.978 1.00 23.98
ATOM 443 O THR 48 24.254 49.031 50.010 1.00 25.61
ATOM 444 N ARG 49 24.265 46.970 49.180 1.00 27.77
ATOM 445 H ARG 49 24.663 46.074 49.180 1.00 0.00
ATOM 446 CA ARG 49 23.147 47.274 48.283 1.00 31.32
ATOM 447 AB ARG 49 22.961 46.196 47.194 1.00 30.53
ATOM 448 CG ARG 49 24.007 46.144 46.076 1.00 28.56
ATOM 449 CD ARG 49 24.323 47.528 45.510 1.00 30.84
ATOM 450 NE ARG 49 25.396 48.175 46.267 1.00 31.36
ATOM 451 HE ARG 49 25.898 47.636 46.892 1.00 0.00
ATOM 452 CZ ARG 49 25.725 49.460 46.179 1.00 31.53
ATOM 453 NH1 ARG 49 25.068 50.272 45.359 1.00 33.61
ATOM 454 HH11 ARG 49 24.321 49.918 44.792 1.00 0.00
ATOM 455 HH12 ARG 49 25.326 51.236 45.287 1.00 0.00
ATOM 456 NH2 ARG 49 26.718 49.931 46.916 1.00 31.78
ATOM 457 HH21 ARG 49 27.214 49.324 47.530 1.00 0.00
ATOM 458 HH22 ARG 49 26.973 50.898 46.847 1.00 0.00
ATOM 459 C ARG 49 21.805 47.480 48.986 1.00 35.36
ATOM 460 O ARG 49 21.366 46.667 49.791 1.00 34.08
ATOM 461 N PRO 50 21.128 48.586 48.673 1.00 39.27
ATOM 462 CD PRO 50 21.530 49.640 47.723 1.00 41.19
ATOM 463 CA PRO 50 19.826 48.877 49.274 1.00 39.02
ATOM 464 CB PRO 50 19.621 50.337 48.904 1.00 42.38
ATOM 465 CG PRO 50 20.238 50.390 47.501 1.00 44.74
ATOM 466 C PRO 50 18.787 47.995 48.575 1.00 38.81
ATOM 467 O PRO 50 19.075 47.393 47.539 1.00 34.20
ATOM 468 N ILE 51 17.575 47.970 49.125 1.00 39.84
ATOM 469 H ILE 51 17.435 48.506 49.931 1.00 0.00
ATOM 470 CA ILE 51 16.434 47.191 48.621 1.00 41.44
ATOM 471 CB ILE 51 15.861 47.734 47.253 1.00 45.38
ATOM 472 CG2 ILE 51 15.891 49.273 47.224 1.00 47.02
ATOM 473 CG1 ILE 51 16.608 47.137 46.055 1.00 50.71
ATOM 474 CD1 ILE 51 16.119 47.630 44.696 1.00 54.88
ATOM 475 C ILE 51 16.578 45.655 48.577 1.00 37.85
ATOM 476 I OLE 51 15.584 44.945 48.738 1.00 39.23
ATOM 477 N LEU 52 17.789 45.141 48.366 1.00 31.60
ATOM 478 H LEU 52 18.552 45.723 48.238 1.00 0.00
ATOM 551 CD1 LEU 60 22.417 39.325 44.150 1.00 17.25
ATOM 552 CD2 LEU 60 23.183 37.358 42.846 1.00 13.12
ATOM 553 C LEU 60 25.783 36.158 45.860 1.00 12.78
ATOM 554 O LEU 60 26.713 35.935 45.074 1.00 13.84
ATOM 555 N GLY 61 25.938 36.315 47.172 1.00 9.31
ATOM 556 H GLY 61 25.163 36.524 47.724 1.00 0.00
ATOM 557 CA GLY 61 27.238 36.195 47.802 1.00 9.25
ATOM 558 C GLY 61 27.792 34.818 47.511 1.00 10.59
ATOM 559 O GLY 61 28.934 34.676 47.077 1.00 11.56
ATOM 560 N PHE 62 26.698 33.800 47.716 1.00 10.85
ATOM 561 H PHE 62 26.071 33.988 48.054 1.00 0.00
ATOM 562 CA PHE 62 27.346 32.407 47.450 1.00 12.29
ATOM 563 CB PHE 52 26.156 31.517 47.818 1.00 10.34
ATOM 564 CG PHE 62 26.394 30.045 47.647 1.00 16.08
ATOM 565 CD1 PHE 62 26.812 29.276 48.716 1.00 13.97
ATOM 566 CD2 PHE 62 26.111 29.409 46.437 1.00 20.52
ATOM 567 CE1 PHE 62 26.941 27.898 48.595 1.00 16.42
ATOM 568 CE2 PHE 62 26.237 28.026 46.306 1.00 20.64
ATOM 569 CZ PHE 62 26.655 27.271 47.394 1.00 19.89
ATOM 570 C PHE 62 27.739 32.204 45.957 1.00 12.39
ATOM 571 O PHE 62 28.817 31.672 45.643 1.00 9.64

-continued

```
ATOM 500 O   PRO 54 20.766 37.906 52.405 1.00  9.38       ATOM 572 N   VAL 63 26.859 32.632 45.051 1.00 12.11
ATOM 501 N   LEU 55 18.534 37.717 52.418 1.00 12.84       ATOM 573 H   VAL 63 26.030 33.048 45.363 1.00  0.00
ATOM 502 H   LEU 55 17.676 38.141 52.613 1.00  0.00       ATOM 574 CA  VAL 63 27.086 32.507 43.611 1.00 14.15
ATOM 503 CA  LEU 55 18.561 36.375 51.847 1.00 14.56       ATOM 575 CB  VAL 63 25.945 33.160 42.787 1.00 16.96
ATOM 504 CB  LEU 55 17.162 35.796 51.762 1.00 17.02       ATOM 576 CG1 VAL 63 26.214 32.989 41.295 1.00 15.72
ATOM 505 CG  LEU 55 16.970 34.283 51.921 1.00 21.28       ATOM 577 CG2 VAL 63 24.609 32.535 43.150 1.00 14.32
ATOM 506 CD1 LEU 55 15.619 33.906 51.335 1.00 25.89       ATOM 578 C   VAL 63 28.409 33.130 43.195 1.00 11.36
ATOM 507 CD2 LEU 55 18.057 33.485 51.254 1.00 17.96       ATOM 579 O   VAL 63 29.227 32.489 42.548 1.00 12.16
ATOM 508 C   LEU 55 19.126 36.459 50.445 1.00 15.67       ATOM 580 N   PHE 64 28.621 34.373 43.594 1.00 11.64
ATOM 509 O   LEU 55 20.019 35.698 50.068 1.00 18.05       ATOM 581 H   PHE 64 27.932 34.829 44.117 1.00  0.00
ATOM 510 N   THR 56 18.579 37.381 49.669 1.00 15.34       ATOM 582 CA  PHE 64 29.844 34.078 43.267 1.00 12.42
ATOM 511 H   THR 56 17.859 37.924 50.002 1.00  0.00       ATOM 583 CB  PHE 64 29.766 36.526 43.729 1.00 12.23
ATOM 512 CA  THR 56 19.018 37.602 48.297 1.00 16.13       ATOM 584 CG  PHE 64 28.960 37.386 42.813 1.00 19.72
ATOM 513 CB  THR 56 18.258 38.790 47.693 1.00 15.71       ATOM 585 CD1 PHE 64 28.005 38.256 43.308 1.00 21.00
ATOM 514 OG1 THR 56 16.900 38.403 47.495 1.00 17.76       ATOM 586 CD2 PHE 64 29.153 37.315 41.429 1.00 20.33
ATOM 515 HG1 THR 56 16.415 39.120 47.104 1.00  0.00       ATOM 587 CE1 PHE 64 27.251 39.052 42.431 1.00 26.47
ATOM 516 CG2 THR 56 18.869 39.232 46.367 1.00 13.57       ATOM 588 CE2 PHE 64 28.409 38.105 40.549 1.00 24.02
ATOM 517 C   THR 56 20.526 37.862 48.228 1.00 15.56       ATOM 589 CZ  PHE 64 27.454 38.976 41.049 1.00 22.91
ATOM 518 O   THR 56 21.230 37.338 47.349 1.00 13.64       ATOM 590 C   PHE 64 31.122 34.432 43.739 1.00 12.20
ATOM 519 N   LYS 57 21.002 38.694 49.149 1.00 12.96       ATOM 591 O   PHE 64 32.090 34.385 42.982 1.00 10.58
ATOM 520 H   LYS 57 20.380 39.096 49.786 1.00  0.00       ATOM 592 N   THR 64 31.136 33.896 44.958 1.00 15.46
ATOM 521 CA  LYS 57 22.414 39.031 49.236 1.00 15.26       ATOM 593 H   THR 65 30.331 33.930 45.527 1.00  0.00
ATOM 522 CB  LYS 57 22.626 40.115 50.292 1.00 16.39       ATOM 594 CA  THR 65 32.353 33.256 45.458 1.00 15.26
ATOM 523 CG  LYS 57 22.043 41.458 49.935 1.00 15.74       ATOM 595 CB  THR 65 32.276 32.889 46.968 1.00 15.45
ATOM 524 CD  LYS 57 22.365 42.457 51.034 1.00 18.06       ATOM 596 OG1 THR 65 31.493 31.709 47.141 1.00 30.54
ATOM 525 CE  LYS 57 22.042 43.870 50.593 1.00 20.25       ATOM 597 HG1 THR 65 31.874 30.971 46.666 1.00  0.00
ATOM 526 NZ  LYS 57 22.223 44.831 51.705 1.00 23.31       ATOM 598 CG2 THR 65 31.643 33.994 47.749 1.00 11.88
ATOM 527 HZ1 LYS 57 23.200 44.804 52.032 1.00  0.00       ATOM 599 C   THR 65 32.613 31.987 44.665 1.00 13.68
ATOM 528 HZ2 LYS 57 21.589 44.571 52.494 1.00  0.00       ATOM 600 O   THR 65 33.753 31.627 44.389 1.00 17.47
ATOM 529 HZ3 LYS 57 21.983 45.791 51.386 1.00  0.00       ATOM 601 N   LEU 66 31.535 31.330 44.272 1.00 14.36
ATOM 530 C   LYS 57 23.288 37.814 49.569 1.00 14.09       ATOM 602 H   LEU 66 30.645 31.700 44.486 1.00  0.00
ATOM 531 O   LYS 57 24.448 37.740 49.129 1.00 12.70       ATOM 603 CA  LEU 66 31.619 30.090 43.530 1.00 16.09
ATOM 532 N   GLY 58 22.733 36.887 50.358 1.00 15.03       ATOM 604 CB  LEU 66 30.234 29.444 43.494 1.00 19.06
ATOM 533 H   GLY 58 21.826 37.028 50.701 1.00  0.00       ATOM 605 CG  LEU 66 30.034 28.010 43.971 1.00 26.72
ATOM 534 CA  GLY 58 23.446 35.676 50.741 1.00 14.02       ATOM 606 CD1 LEU 66 30.297 27.917 45.486 1.00 33.43
ATOM 535 C   GLY 58 23.603 34.745 49.555 1.00 14.16       ATOM 607 CD2 LEU 66 28.604 27.604 43.665 1.00 29.53
ATOM 536 O   GLY 58 24.673 34.168 49.331 1.00 14.13       ATOM 608 C   LEU 66 32.095 30.238 42.084 1.00 18.82
ATOM 537 N   ILE 59 22.526 34.620 48.781 1.00 16.19       ATOM 609 O   LEU 66 32.762 29.347 41.554 1.00 19.11
ATOM 538 H   ILE 59 21.715 35.105 49.041 1.00  0.00       ATOM 610 N   THR 67 31.697 31.335 41.446 1.00 15.33
ATOM 539 CA  ILE 59 22.494 33.791 47.576 1.00 12.32       ATOM 611 H   THR 67 31.183 32.009 41.937 1.00  0.00
ATOM 540 CB  ILE 59 21.055 33.722 46.991 1.00 11.19       ATOM 612 CA  THR 67 31.982 31.563 40.042 1.00 14.14
ATOM 541 CG2 ILE 59 21.037 33.034 45.605 1.00  3.54       ATOM 613 CB  THR 67 30.722 32.041 39.345 1.00  8.38
ATOM 542 CG1 ILE 59 20.148 33.005 47.997 1.00  9.06       ATOM 614 OG1 THR 67 30.300 33.287 39.916 1.00 11.18
ATOM 543 CD1 ILE 59 18.712 32.824 47.543 1.00 15.78       ATOM 615 HG1 THR 67 30.109 33.172 40.848 1.00  0.00
ATOM 544 C   ILE 59 23.489 34.354 46.548 1.00 15.16       ATOM 616 CG2 THR 67 29.620 31.016 39.528 1.00  5.37
ATOM 545 O   ILE 59 24.337 33.621 46.036 1.00 15.23       ATOM 617 C   THR 67 33.141 32.486 39.705 1.00 18.23
ATOM 546 N   LEU 60 23.436 35.658 46.301 1.00 12.86       ATOM 618 O   THR 67 33.656 32.455 38.583 1.00 17.80
ATOM 547 H   LEU 60 22.768 36.214 46.753 1.00  0.00       ATOM 619 N   VAL 68 33.564 33.281 40.683 1.00 17.46
ATOM 548 CA  LEU 60 24.361 36.269 45.358 1.00 14.47       ATOM 620 H   VAL 68 33.109 33.265 41.538 1.00  0.00
ATOM 549 CB  LEU 60 24.009 37.730 45.132 1.00 16.93       ATOM 621 CA  VAL 68 34.678 34.197 40.506 1.00 19.37
ATOM 550 CG  LEU 60 22.813 37.877 44.211 1.00 14.49       ATOM 622 CB  VAL 68 34.813 35.092 41.760 1.00 22.10
ATOM 623 CG1 VAL 68 35.816 34.536 42.738 1.00 15.19       ATOM 695 N   ARG 76 35.411 33.893 54.533 1.00 16.95
ATOM 624 CG2 VAL 68 35.058 36.536 41.370 1.00 19.51       ATOM 696 H   ARG 76 35.828 33.225 55.110 1.00  0.00
ATOM 625 C   VAL 68 35.920 33.315 40.245 1.00 22.98       ATOM 697 CA  ARG 76 33.983 33.805 54.245 1.00 16.24
ATOM 626 O   VAL 68 36.066 32.260 40.873 1.00 22.77       ATOM 698 CB  ARG 76 33.377 32.548 54.883 1.00 16.94
ATOM 627 N   PRO 69 36.813 33.724 39.307 1.00 23.51       ATOM 699 CG  ARG 76 33.854 31.233 54.254 1.00 18.42
ATOM 628 CD  PRO 69 36.816 34.956 38.492 1.00 20.60       ATOM 700 CD  ARG 76 33.766 31.366 52.751 1.00 20.49
ATOM 629 CA  PRO 69 37.991 32.879 39.046 1.00 25.71       ATOM 701 NE  ARG 76 33.596 30.103 52.052 1.00 23.98
ATOM 630 CB  PRO 69 38.733 33.598 37.908 1.00 25.24       ATOM 702 HE  ARG 76 33.195 29.370 52.536 1.00  0.00
ATOM 631 CG  PRO 69 38.157 34.946 37.880 1.00 25.82       ATOM 703 CZ  ARG 76 34.006 29.895 50.807 1.00 19.60
ATOM 632 C   PRO 69 38.842 32.622 40.281 1.00 29.88       ATOM 704 NH1 ARG 76 34.618 30.867 50.151 1.00 21.93
ATOM 633 O   PRO 69 39.172 31.465 40.570 1.00 31.71       ATOM 705 HH11 ARG 76 34.764 31.756 50.588 1.00  0.00
ATOM 634 N   SER 70 39.147 33.675 41.038 1.00 28.74       ATOM 706 HH12 ARG 76 34.916 30.727 49.205 1.00  0.00
ATOM 635 H   SER 70 38.847 34.569 40.767 1.00  0.00       ATOM 707 NH2 ARG 76 33.766 28.741 50.211 1.00 16.37
ATOM 636 CA  SER 70 39.929 33.521 42.268 1.00 31.02       ATOM 708 HH21 ARG 76 33.286 28.016 50.700 1.00  0.00
ATOM 637 CB  SER 70 41.386 33.994 42.085 1.00 32.48       ATOM 709 HH22 ARG 76 34.074 28.595 49.269 1.00  0.00
ATOM 638 OG  SER 70 41.530 34.878 40.981 1.00 41.24       ATOM 710 C   ARG 76 33.339 35.062 54.822 1.00 14.95
ATOM 639 HG  SER 70 40.971 35.653 41.103 1.00  0.00       ATOM 711 O   ARG 76 33.810 35.591 55.823 1.00 19.14
ATOM 640 C   SER 70 39.298 34.244 43.449 1.00 26.93       ATOM 712 N   ARG 77 32.285 35.559 54.192 1.00 14.43
ATOM 641 O   SER 70 38.832 35.380 43.318 1.00 25.63       ATOM 713 H   ARG 77 31.937 35.107 53.402 1.00  0.00
ATOM 642 N   GLU 71 39.237 33.554 44.585 1.00 24.01       ATOM 714 CA  ARG 77 31.639 36.776 54.673 1.00 16.84
ATOM 643 H   GLU 71 39.537 32.625 44.607 1.00  0.00       ATOM 715 CB  ARG 77 31.101 37.592 53.497 1.00 16.48
ATOM 644 CA  GLU 71 38.702 34.141 45.811 1.00 23.36       ATOM 716 CG  ARG 77 32.186 38.079 52.557 1.00 19.55
ATOM 645 CB  GLU 71 38.264 33.066 46.797 1.00 26.79       ATOM 717 CD  ARG 77 32.801 39.413 52.993 1.00 25.33
ATOM 646 CG  GLU 71 37.087 32.247 46.346 1.00 36.00       ATOM 718 NE  ARG 77 34.043 39.317 53.765 1.00 32.73
ATOM 647 CD  GLU 71 36.736 31.171 47.339 1.00 39.09       ATOM 719 HE  ARG 77 34.052 39.719 54.654 1.00  0.00
ATOM 648 OE1 GLU 71 36.170 30.147 46.911 1.00 41.16       ATOM 720 CZ  ARG 77 35.158 38.697 53.374 1.00 37.18
ATOM 649 OE2 GLU 71 37.020 31.347 48.545 1.00 46.63       ATOM 721 NH1 ARG 77 35.217 38.075 52.206 1.00 45.18
ATOM 650 C   GLU 71 39.797 34.970 46.459 1.00 22.23       ATOM 722 HH11 ARG 77 34.443 38.091 51.580 1.00  0.00
```

-continued

```
ATOM   651  O   GLU 71  39.527 35.732 47.376 1.00 20.81
ATOM   652  N   ARG 72  41.040 34.766 46.021 1.00 18.01
ATOM   653  H   ARG 72  41.187 34.083 45.337 1.00 0.00
ATOM   654  CA  ARG 72  42.184 35.508 46.541 1.00 18.63
ATOM   655  CB  ARG 72  45.059 36.987 46.162 1.00 22.88
ATOM   656  CG  ARG 72  41.640 37.218 44.712 1.00 22.96
ATOM   657  CD  ARG 72  41.631 38.703 44.344 1.00 23.05
ATOM   658  NE  ARG 72  41.397 38.868 42.909 1.00 29.61
ATOM   659  HE  ARG 72  41.165 30.067 42.396 1.00 0.00
ATOM   660  CZ  ARG 72  41.470 40.024 42.253 1.00 27.27
ATOM   661  NH1 ARG 72  41.776 41.135 42.901 1.00 25.95
ATOM   662  HH11 ARG 72 41.955 41.107 43.890 1.00 0.00
ATOM   663  HH12 ARG 72 41.838 42.002 42.414 1.00 0.00
ATOM   664  NH2 ARG 72  41.212 40.069 40.951 1.00 23.28
ATOM   665  HH21 ARG 72 40.977 39.232 40.462 1.00 0.00
ATOM   666  HH22 ARG 72 41.283 40.938 40.465 1.00 0.00
ATOM   667  C   ARG 72  42.363 35.369 48.061 1.00 20.31
ATOM   668  O   ARG 72  42.750 36.319 48.738 1.00 15.15
ATOM   669  N   GLY 73  42.059 34.186 48.583 1.00 18.99
ATOM   670  H   GLY 73  41.643 33.504 48.071 1.00 0.00
ATOM   671  CA  GLY 73  42.192 33.927 50.000 1.00 20.88
ATOM   672  C   GLY 73  41.330 34.797 50.894 1.00 21.37
ATOM   673  O   GLY 73  41.711 35.087 52.033 1.00 25.47
ATOM   674  N   LEU 74  40.181 35.238 50.396 1.00 21.12
ATOM   675  H   LEU 74  39.922 35.014 49.482 1.00 0.00
ATOM   676  CA  LEU 74  39.921 36.063 51.212 1.00 21.29
ATOM   677  CB  LEU 74  38.303 36.834 50.345 1.00 21.15
ATOM   678  CG  LEU 74  38.927 37.751 49.304 1.00 29.09
ATOM   679  CD1 LEU 74  37.802 38.397 48.561 1.00 32.52
ATOM   680  CD2 LEU 74  39.872 38.802 49.919 1.00 27.60
ATOM   681  C   LEU 74  38.522 35.181 52.190 1.00 20.91
ATOM   682  O   LEU 74  38.114 34.070 51.841 1.00 17.35
ATOM   683  N   GLN 75  38.363 35.664 53.422 1.00 21.46
ATOM   684  H   GLN 75  38.752 36.530 53.638 1.00 0.00
ATOM   685  CA  GLN 75  37.631 34.928 54.450 1.00 19.45
ATOM   686  CB  GLN 75  37.782 35.631 55.807 1.00 19.60
ATOM   687  CG  GLN 75  39.215 35.713 56.358 1.00 17.96
ATOM   688  CD  GLN 75  36.866 34.358 56.592 1.00 15.76
ATOM   689  OE1 GLN 75  39.189 33.326 56.691 1.00 15.14
ATOM   690  NE2 GLN 75  41.197 34.351 56.669 1.00 16.91
ATOM   691  HE21 GLN 75 41.683 35.196 56.567 1.00 0.00
ATOM   692  HE22 GLN 75 41.626 33.501 56.803 1.00 0.00
ATOM   693  C   GLN 75  36.151 34.888 54.053 1.00 17.46
ATOM   694  O   GLN 75  35.709 35.720 53.268 1.00 17.50
ATOM   767  H   GLN 81  27.939 34.755 55.800 1.00 0.00
ATOM   768  CA  GLN 81  27.010 33.111 56.751 1.00 10.72
ATOM   769  CB  GLN 81  28.179 33.124 57.729 1.00 9.85
ATOM   770  CG  GLN 81  29.516 32.805 57.081 1.00 11.05
ATOM   771  CD  GLN 81  30.666 32.915 58.063 1.00 18.77
ATOM   772  OE1 GLN 81  30.843 33.949 58.711 1.00 15.83
ATOM   773  NE2 GLN 81  31.450 31.841 58.192 1.00 16.43
ATOM   774  HE21 GLN 81 31.254 31.037 57.660 1.00 0.00
ATOM   775  HE22 GLN 81 32.194 31.896 58.821 1.00 0.00
ATOM   776  C   GLN 81  25.710 33.305 57.505 1.00 11.63
ATOM   777  O   GLN 81  24.981 32.341 57.750 1.00 13.10
ATOM   778  N   ASN 82  25.399 34.557 57.838 1.00 12.35
ATOM   779  H   ASN 82  26.007 35.283 57.589 1.00 0.00
ATOM   780  CA  ASN 82  24.177 34.871 58.564 1.00 13.80
ATOM   781  CB  ASN 82  24.262 36.279 59.150 1.00 16.03
ATOM   782  CG  ASN 82  25.135 36.330 60.397 1.00 17.96
ATOM   783  OD1 ASN 82  25.202 35.357 61.149 1.00 11.67
ATOM   784  ND2 ASN 82  25.806 37.453 60.615 1.00 14.22
ATOM   785  HD21 ASN 82 25.720 38.191 59.981 1.00 0.00
ATOM   786  HD22 ASN 82 26.370 37.486 61.411 1.00 0.00
ATOM   787  C   ASN 82  22.922 34.683 57.719 1.00 17.66
ATOM   788  O   ASN 82  21.896 34.205 58.217 1.00 18.68
ATOM   789  N   ALA 83  23.022 34.980 56.424 1.00 15.35
ATOM   790  H   ALA 83  23.868 35.332 56.076 1.00 0.00
ATOM   791  CA  ALA 83  21.893 34.810 55.504 1.00 15.30
ATOM   792  CB  ALA 83  22.160 35.579 54.199 1.00 16.37
ATOM   793  C   ALA 83  21.602 33.339 55.180 1.00 16.18
ATOM   794  O   ALA 83  20.448 32.937 55.039 1.00 18.70
ATOM   795  N   LEU 84  22.649 32.528 55.095 1.00 15.97
ATOM   796  H   LEU 84  23.548 32.880 55.267 1.00 0.00
ATOM   797  CA  LEU 84  22.496 31.121 57.757 1.00 14.89
ATOM   798  CB  LEU 84  23.579 30.726 53.739 1.00 12.49
ATOM   799  CG  LEU 84  23.696 31.532 52.433 1.00 9.46
ATOM   800  CD1 LEU 84  24.793 30.962 51.574 1.00 4.78
ATOM   801  CD2 LEU 84  22.360 31.529 51.673 1.00 7.79
ATOM   723  HH12 ARG 77 36.082 37.653 51.907 1.00 0.00
ATOM   724  NH2 ARG 77  36.251 38.750 54.125 1.00 35.27
ATOM   725  HH21 ARG 77 36.239 39.253 54.988 1.00 0.00
ATOM   726  HH22 ARG 77 37.096 38.304 53.821 1.00 0.00
ATOM   727  C   ARG 77  30.539 36.567 55.700 1.00 18.14
ATOM   728  O   ARG 77  29.620 35.763 55.512 1.00 16.53
ATOM   729  N   ARG 78  30.615 37.345 56.772 1.00 21.45
ATOM   730  H   ARG 78  31.375 37.957 56.846 1.00 0.00
ATOM   731  CA  ARG 78  29.638 37.303 57.859 1.00 19.61
ATOM   732  CB  ARG 78  30.008 38.375 58.888 1.00 25.10
ATOM   733  CG  ARG 78  28.959 38.634 59.928 1.00 35.74
ATOM   734  CD  ARG 78  29.425 39.673 60.914 1.00 47.69
ATOM   735  NE  ARG 78  28.454 29.822 61.996 1.00 62.90
ATOM   736  HE  ARG 78  28.6321 39.351 62.837 1.00 0.00
ATOM   737  CZ  ARG 78  27.351 40.564 61.917 1.00 67.36
ATOM   738  NH1 ARG 78  27.083 41.242 60.804 1.00 72.55
ATOM   739  HH11 ARG 78 27.712 41.191 60.025 1.00 0.00
ATOM   740  HH12 ARG 78 26.257 41.797 60.740 1.00 0.00
ATOM   741  NH2 ARG 78  26.491 40.587 62.929 1.00 67.11
ATOM   742  HH21 ARG 78 26.677 40.051 63.752 1.00 0.00
ATOM   743  HH22 ARG 78 25.666 41.146 62.868 1.00 0.00
ATOM   744  C   ARG 78  28.189 37.495 57.348 1.00 15.98
ATOM   745  O   ARG 78  27.284 36.770 57.761 1.00 16.16
ATOM   746  N   PHE 79  27.972 38.425 56.411 1.00 16.65
ATOM   747  H   PHE 79  28.714 38.951 56.083 1.00 0.00
ATOM   748  CA  PHE 79  26.613 38.662 55.881 1.00 11.51
ATOM   749  CB  PHE 79  26.499 39.986 55.062 1.00 11.25
ATOM   750  CG  PHE 79  27.070 39.937 53.648 1.00 12.26
ATOM   751  CD1 PHE 79  26.234 39.670 52.549 1.00 12.23
ATOM   752  CD2 PHE 79  28.416 40.218 53.408 1.00 9.84
ATOM   753  CE1 PHE 79  26.731 39.685 51.233 1.00 12.52
ATOM   754  CD2 PHE 79  28.925 40.239 52.089 1.00 11.33
ATOM   755  CZ  PHE 79  28.078 39.972 51.007 1.00 8.90
ATOM   756  C   PHE 79  26.044 37.458 55.143 1.00 8.21
ATOM   757  O   PHE 79  24.850 37.185 55.196 1.00 8.94
ATOM   758  N   VAL 80  26.923 36.676 54.534 1.00 7.83
ATOM   759  H   VAL 80  27.874 36.883 54.578 1.00 0.00
ATOM   760  CA  VAL 80  26.488 35.494 53.824 1.00 9.30
ATOM   761  CB  VAL 80  27.509 35.071 52.743 1.00 8.14
ATOM   762  CG1 VAL 80  27.013 33.862 52.004 1.00 6.78
ATOM   763  CG2 VAL 80  27.702 36.197 51.741 1.00 11.62
ATOM   764  C   VAL 80  26.247 34.351 54.818 1.00 9.86
ATOM   765  O   VAL 80  25.236 33.659 54.741 1.00 9.66
ATOM   766  N   GLN 81  27.158 34.171 55.766 1.00 10.87
ATOM   839  CB  ASP 89  15.664 26.240 62.397 1.00 11.39
ATOM   840  CG  ASP 89  14.532 25.309 62.766 1.00 17.46
ATOM   841  OD1 ASP 89  13.987 25.419 63.885 1.00 20.46
ATOM   842  OD2 ASP 89  14.166 24.464 61.936 1.00 19.66
ATOM   843  C   ASP 89  17.455 24.544 62.930 1.00 14.77
ATOM   844  O   ASP 89  17.798 24.208 61.798 1.00 13.18
ATOM   845  N   PRO 90  17.445 23.677 63.972 1.00 17.07
ATOM   846  CD  PRO 90  16.998 24.000 65.343 1.00 11.50
ATOM   847  CA  PRO 90  17.911 22.281 63.906 1.00 14.78
ATOM   848  CB  PRO 90  17.706 21.776 65.335 1.00 12.18
ATOM   849  CG  PRO 90  17.796 23.018 66.161 1.00 12.39
ATOM   850  C   PRO 90  17.161 21.416 62.890 1.00 14.07
ATOM   851  O   PRO 90  17.749 20.536 62.266 1.00 15.58
ATOM   852  N   ASN 91  15.867 21.654 62.717 1.00 14.18
ATOM   853  H   ASN 91  15.430 22.353 63.236 1.00 0.00
ATOM   854  CA  ASN 91  15.105 20.883 61.749 1.00 16.21
ATOM   855  CB  ASN 91  13.619 21.115 61.936 1.00 24.97
ATOM   856  CG  ASN 91  12.907 19.885 62.454 1.00 35.60
ATOM   857  OD1 ASN 91  11.990 19.376 61.815 1.00 42.50
ATOM   858  ND2 ASN 91  13.322 19.400 62.620 1.00 40.50
ATOM   859  HD21 ASN 91 14.052 19.830 64.095 1.00 0.00
ATOM   860  HD22 ASN 91 12.848 18.612 63.957 1.00 0.00
ATOM   861  C   ASN 91  15.543 21.210 60.319 1.00 15.13
ATOM   862  O   ASN 91  15.691 20.316 59.483 1.00 13.21
ATOM   863  N   ASN 92  15.787 22.488 60.056 1.00 11.44
ATOM   864  H   ASN 92  15.647 23.155 60.749 1.00 0.00
ATOM   865  CA  ASN 92  16.259 22.916 58.744 1.00 8.74
ATOM   866  CB  ASN 92  16.399 24.435 58.678 1.00 4.08
ATOM   867  CG  ASN 92  15.053 25.140 58.526 1.00 9.59
ATOM   868  OD1 ASN 92  140052 24.508 58.211 1.00 10.61
ATOM   869  ND2 ASN 92  15.031 26.445 58.746 1.00 5.11
ATOM   870  HD21 ASN 92 15.856 26.910 58.994 1.00 0.00
ATOM   871  HD22 ASN 92 14.166 26.896 58.644 1.00 0.00
ATOM   872  C   ASN 92  17.615 22.305 58.508 1.00 7.66
ATOM   873  O   ASN 92  17.862 21.705 57.472 1.00 12.10
```

-continued

```
ATOM 802  C   LEU 84  22.539 30.173 55.966 1.00 16.23
ATOM 803  O   LEU 84  22.945 29.021 55.845 1.00 15.18
ATOM 804  N   ASN 85  22.083 60.622 57.125 1.00 17.83
ATOM 805  H   ASN 85  21.729 34.533 57.210 1.00 0.00
ATOM 806  CA  ASN 85  22.139 29.747 58.283 1.00 19.32
ATOM 807  CB  ASN 85  22.730 30.478 59.478 1.00 16.43
ATOM 808  CB  ASN 85  21.807 31.497 60.037 1.00 19.25
ATOM 809  OD1 ASN 85  20.632 31.559 59.670 1.00 22.86
ATOM 810  ND2 ASN 85  22.323 32.328 60.921 1.00 23.33
ATOM 811  HD21 ASN 85 23.280 32.238 61.168 1.00 0.00
ATOM 812  HD22 ASN 85 21.744 33.010 61.298 1.00 0.00
ATOM 813  C   ASN 85  20.845 29.032 58.679 1.00 22.92
ATOM 814  O   ASN 85  20.788 28.420 59.753 1.00 23.44
ATOM 815  N   GLY 86  19.814 29.109 57.827 1.00 21.89
ATOM 816  H   GLY 86  19.940 29.596 56.986 1.00 0.00
ATOM 817  CA  GLY 86  18.533 28.447 58.096 1.00 18.54
ATOM 818  C   GLY 86  17.884 28.809 59.431 1.00 17.54
ATOM 819  O   GLY 86  17.151 28.004 60.013 1.00 14.35
ATOM 820  N   ASN 87  18.141 30.036 59.891 1.00 19.78
ATOM 821  H   ASN 87  18.711 30.625 59.355 1.00 0.00
ATOM 822  CA  ASN 87  17.632 30.565 61.169 1.00 23.22
ATOM 823  CB  ASN 87  16.105 30.476 61.252 1.00 27.67
ATOM 824  CG  ASN 87  15.423 31.253 60.163 1.00 36.30
ATOM 825  OD1 ASN 87  15.759 32.409 59.924 1.00 44.79
ATOM 826  ND2 ASN 87  14.468 30.627 59.485 1.00 36.18
ATOM 827  HD21 ASN 87 14.227 29.712 59.733 1.00 0.00
ATOM 828  HD22 ASN 87 14.003 31.146 58.797 1.00 0.00
ATOM 829  C   ASN 87  18.223 29.804 62.349 1.00 23.72
ATOM 830  O   ASN 87  17.704 29.890 63.466 1.00 23.99
ATOM 831  N   GLY 88  19.299 29.059 62.090 1.00 19.60
ATOM 832  H   GLY 88  19.679 29.052 61.194 1.00 0.00
ATOM 833  CA  GLY 88  19.929 28.255 63.122 1.00 18.58
ATOM 834  C   GLY 88  18.962 27.204 63.628 1.00 15.03
ATOM 835  O   GLY 88  19.108 26.685 64.725 1.00 15.92
ATOM 836  N   ASP 89  17.950 26.911 62.824 1.00 14.80
ATOM 837  H   ASP 89  17.892 27.352 61.958 1.00 0.00
ATOM 838  CA  ASP 89  16.941 25.953 63.185 1.00 12.89
ATOM 911  N   VAL 97  21.348 18.514 55.963 1.00 10.71
ATOM 912  H   VAL 97  20.857 18.752 56.779 1.00 0.00
ATOM 913  CA  VAL 97  22.361 17.469 56.018 1.00 8.78
ATOM 914  CB  VAL 97  22.651 17.066 57.489 1.00 9.36
ATOM 915  CG1 VAL 97  23.413 15.745 57.563 1.00 9.31
ATOM 916  CG2 VAL 97  23.430 18.165 58.164 1.00 3.88
ATOM 917  C   VAL 97  21.892 16.267 55.193 1.00 7.98
ATOM 918  O   VAL 97  22.684 15.608 54.514 1.00 8.85
ATOM 919  N   LYS 98  20.593 16.015 55.215 1.00 7.81
ATOM 920  H   LYS 98  20.001 16.577 55.764 1.00 0.00
ATOM 921  CA  LYS 98  20.024 14.904 54.455 1.00 12.54
ATOM 922  CB  LYS 98  18.572 14.655 54.872 1.00 8.12
ATOM 923  CG  LYS 98  18.498 13.903 56.173 1.00 10.36
ATOM 924  CD  LYS 98  17.145 14.029 56.837 1.00 13.11
ATOM 925  CE  LYS 98  17.122 13.169 58.077 1.00 12.15
ATOM 926  NZ  LYS 98  15.820 13.292 58.758 1.00 15.93
ATOM 927  HZ1 LYS 98  15.061 12.984 58.126 1.00 0.00
ATOM 928  HZ2 LYS 98  15.667 14.285 59.035 1.00 0.00
ATOM 929  HZ2 LYS 98  15.824 12.701 59.617 1.00 0.00
ATOM 930  C   LYS 98  20.123 15.186 52.960 1.00 12.23
ATOM 931  O   LYS 98  20.495 14.301 52.184 1.00 13.83
ATOM 932  N   LEU 99  19.807 16.417 52.565 1.00 7.09
ATOM 933  H   LEU 99  19.503 17.075 53.224 1.00 0.00
ATOM 934  CA  LEU 99  19.906 16.801 51.168 1.00 8.07
ATOM 935  CB  LEU 99  19.427 18.250 50.959 1.00 7.14
ATOM 936  CG  LEU 99  19.667 18.878 49.578 1.00 5.05
ATOM 937  CD1 LEU 99  19.136 17.982 48.436 1.00 7.40
ATOM 938  CD2 LEU 99  18.993 20.232 49.534 1.00 6.20
ATOM 939  C   LEU 99  21.358 16.653 50.721 1.00 7.22
ATOM 940  O   LEU 99  21.647 16.056 49.682 1.00 9.37
ATOM 941  N   TYR 100 22.265 17.176 51.531 1.00 5.02
ATOM 942  H   TYR 100 21.967 17.631 52.345 1.00 0.00
ATOM 943  CA  TYR 100 23.684 17.117 51.251 1.00 6.66
ATOM 944  CB  TYR 100 24.464 17.708 52.438 1.00 5.94
ATOM 945  CG  TYR 100 25.959 17.489 52.397 1.00 7.46
ATOM 946  CD1 TYR 100 26.713 17.860 51.281 1.00 9.91
ATOM 947  CE1 TYR 100 28.087 17.605 51.214 1.00 10.47
ATOM 948  CD2 TYR 100 26.622 16.867 53.463 1.00 8.23
ATOM 949  CE2 TYR 100 28.005 16.617 53.407 1.00 9.35
ATOM 950  CZ  TYR 100 28.724 16.984 52.274 1.00 12.51
ATOM 951  OH  TYR 100 30.067 16.708 52.172 1.00 10.26
ATOM 952  HH  TYR 100 30.354 16.259 52.970 1.00 0.00
ATOM 874  N   MET 93  18.483 22.420 59.505 1.00 9.04
ATOM 875  H   MET 93  18.203 22.880 60.322 1.00 0.00
ATOM 876  CA  MET 93  19.844 21.888 59.425 1.00 12.35
ATOM 877  CB  MET 93  20.623 22.316 60.671 1.00 12.66
ATOM 878  CG  MET 93  20.642 23.835 60.897 1.00 18.15
ATOM 879  SD  MET 93  21.107 24.283 62.597 1.00 21.04
ATOM 880  CE  MET 93  22.720 23.827 62.582 1.00 8.29
ATOM 881  C   MET 93  19.854 20.361 59.267 1.00 13.02
ATOM 882  O   MET 93  20.702 19.794 58.587 1.00 13.82
ATOM 883  N   ASP 94  18.872 19.708 59.878 1.00 14.47
ATOM 884  H   ASP 94  18.231 20.204 60.404 1.00 0.00
ATOM 885  CA  ASP 94  18.747 18.266 59.792 1.00 13.72
ATOM 886  CB  ASP 94  17.654 17.764 60.764 1.00 16.17
ATOM 887  CG  ASP 94  17.359 16.247 60.607 1.00 17.39
ATOM 888  OD1 ASP 94  18.338 15.435 60.773 1.00 23.05
ATOM 889  OD2 ASP 94  16.220 15.888 60.287 1.00 25.15
ATOM 890  C   ASP 94  18.398 17.880 58.363 1.00 12.80
ATOM 891  O   ASP 94  18.976 16.932 57.818 1.00 10.22
ATOM 892  N   LYS 95  17.440 18.588 57.770 1.00 10.60
ATOM 893  H   LYS 95  17.014 19.325 58.265 1.00 0.00
ATOM 894  CA  LYS 95  17.019 18.306 56.400 1.00 10.58
ATOM 895  CB  LYS 95  15.782 19.112 56.043 1.00 14.37
ATOM 896  CG  LYS 95  14.571 18.826 56.894 1.00 21.95
ATOM 897  CD  LYS 95  14.133 17.395 56.745 1.00 34.60
ATOM 898  CE  LYS 95  12.747 17.186 57.358 1.00 43.52
ATOM 899  NZ  LYS 95  12.570 17.755 58.717 1.00 45.28
ATOM 900  HZ1 LYS 95  12.928 18.670 58.895 1.00 0.00
ATOM 901  HZ2 LYS 95  13.245 17.272 59.157 1.00 0.00
ATOM 902  HZ3 LYS 95  11.741 17.465 59.222 1.00 0.00
ATOM 903  C   LYS 95  18.130 16.647 55.248 1.00 9.18
ATOM 904  O   LYS 95  18.330 17.928 54.461 1.00 10.80
ATOM 905  N   ALA 96  18.857 19.731 55.718 1.00 9.15
ATOM 906  H   ALA 96  18.629 20.237 56.527 1.00 0.00
ATOM 907  CA  ALA 96  19.975 20.204 54.898 1.00 11.98
ATOM 908  CB  ALA 96  20.547 21.497 55.455 1.00 7.21
ATOM 909  C   ALA 96  21.068 19.159 54.830 1.00 13.36
ATOM 910  O   ALA 96  21.662 18.956 53.772 1.00 15.09
ATOM 983  C   LYS 102 22.722 13.710 47.218 1.00 13.82
ATOM 984  O   LYS 102 23.048 13.145 46.180 1.00 13.50
ATOM 985  N   LEU 103 22.997 14.991 47.467 1.00 13.29
ATOM 986  H   LEU 103 22.713 15.380 48.316 1.00 0.00
ATOM 987  CA  LEU 103 23.708 15.828 46.506 1.00 12.21
ATOM 988  CB  LEU 103 23.791 17.295 56.951 1.00 7.85
ATOM 989  CG  LEU 103 22.526 18.146 46.922 1.00 8.47
ATOM 990  CD1 LEU 103 22.919 19.595 47.119 1.00 7.33
ATOM 991  CD2 LEU 103 21.801 17.977 45.599 1.00 10.39
ATOM 992  C   LEU 103 25.099 15.300 46.232 1.00 15.80
ATOM 993  O   LEU 103 25.624 15.484 45.130 1.00 20.24
ATOM 994  N   LYS 104 25.702 14.654 47.222 1.00 14.57
ATOM 995  H   LYS 104 25.253 14.573 48.089 1.00 0.00
ATOM 996  CA  LYS 104 27.024 14.064 47.048 1.00 16.23
ATOM 997  CB  LYS 104 27.551 13.495 48.367 1.00 17.01
ATOM 998  CG  LYS 104 28.432 14.446 49.132 1.00 22.33
ATOM 999  CD  LYS 104 29.206 13.692 50.185 1.00 26.94
ATOM 1000 CE  LYS 104 30.608 14.242 50.306 1.00 28.25
ATOM 1001 NZ  LYS 104 31.378 13.464 51.316 1.00 34.09
ATOM 1002 HZ1 LYS 104 31.433 12.467 51.038 1.00 0.00
ATOM 1003 HZ2 LYS 104 30.904 13.537 52.245 1.00 0.00
ATOM 1004 HZ3 LYS 104 32.342 13.853 51.405 1.00 0.00
ATOM 1005 C   LYS 104 27.011 12.946 45.999 1.00 16.92
ATOM 1006 O   LYS 104 28.037 12.651 45.400 1.00 20.96
ATOM 1007 N   ARG 105 25.854 12.327 47.790 1.00 17.39
ATOM 1008 H   ARG 105 25.072 12.599 46.306 1.00 0.00
ATOM 1009 CA  ARG 105 25.715 11.245 44.815 1.00 17.76
ATOM 1010 CB  ARG 105 24.648 10.263 45.284 1.00 22.55
ATOM 1011 CG  ARG 105 24.920 9.587 46.609 1.00 35.04
ATOM 1012 CD  ARG 105 23.658 8.879 47.073 1.00 44.94
ATOM 1013 NE  ARG 105 23.766 8.360 48.436 1.00 57.02
ATOM 1014 HE  ARG 105 24.630 7.998 48.727 1.00 0.00
ATOM 1015 CZ  ARG 105 22.772 8.365 49.321 1.00 58.01
ATOM 1016 NH1 ARG 105 21.588 8.875 48.996 1.00 56.95
ATOM 1017 HH11 ARG 105 21.437 9.249 48.082 1.00 0.00
ATOM 1018 HH12 ARG 105 20.839 8.860 49.653 1.00 0.00
ATOM 1019 NH2 ARG 105 22.949 7.817 50.516 1.00 61.23
ATOM 1020 HH21 ARG 105 23.826 7.408 50.756 1.00 0.00
ATOM 1021 HH22 ARG 105 22.196 7.815 51.179 1.00 0.00
ATOM 1022 C   ARG 105 25.297 11.748 43.437 1.00 18.60
ATOM 1023 O   ARG 105 25.125 10.955 42.504 1.00 23.60
ATOM 1024 N   GLU 106 25.013 13.041 43.345 1.00 15.40
```

-continued

```
ATOM 953  C   TYR 100 24.146 15.700 50.915 1.00 9.97
ATOM 954  O   TYR 100 24.884 15.497 49.947 1.00 8.51
ATOM 955  N   ARG 101 23.696 14.717 51.697 1.00 12.95
ATOM 956  H   ARG 101 23.108 14.936 52.453 1.00 0.00
ATOM 957  CA  ARG 101 24.077 13.325 51.462 1.00 12.96
ATOM 958  CB  ARG 101 23.419 12.396 52.492 1.00 13.49
ATOM 959  CG  ARG 101 23.793 10.921 52.328 1.00 14.43
ATOM 960  CD  ARG 101 23.137 10.023 53.381 1.00 11.92
ATOM 961  NE  ARG 101 23.671 10.254 54.726 1.00 16.66
ATOM 962  HE  ARG 101 25.545 9.853 54.943 1.00 0.00
ATOM 963  CZ  ARG 101 23.055 10.945 55.686 1.00 18.57
ATOM 964  NH1 ARG 101 21.863 11.496 55.473 1.00 13.14
ATOM 965  HH11 ARG 101 21.428 11.384 54.574 1.00 0.00
ATOM 966  HH12 ARG 101 21.406 12.002 56.188 1.00 0.00
ATOM 967  NH2 ARG 101 23.633 11.074 56.871 1.00 13.67
ATOM 968  HH21 ARG 101 24.528 10.664 57.044 1.00 0.00
ATOM 969  HH22 ARG 101 23.172 11.591 57.593 1.00 0.00
ATOM 970  C   ARG 101 23.680 12.909 50.041 1.00 14.49
ATOM 971  O   ARG 101 24.464 12.272 49.327 1.00 12.43
ATOM 972  N   LYS 102 22.462 13.262 49.643 1.00 12.41
ATOM 973  H   LYS 102 21.888 13.773 50.253 1.00 0.00
ATOM 974  CA  LYS 102 21.971 12.937 48.302 1.00 14.14
ATOM 975  CB  LYS 102 20.484 13.233 48.175 1.00 10.90
ATOM 976  CG  LYS 102 19.601 12.387 49.047 1.00 10.43
ATOM 977  CD  LYS 102 18.187 12.883 48.941 1.00 12.57
ATOM 978  CE  LYS 102 17.245 12.032 49.758 1.00 16.49
ATOM 979  NZ  LYS 102 15.842 12.523 49.654 1.00 20.07
ATOM 980  HZ1 LYS 102 15.545 12.498 48.662 1.00 0.00
ATOM 981  HZ2 LYS 102 15.809 13.505 50.005 1.00 0.00
ATOM 982  HZ3 LYS 102 15.227 11.926 50.233 1.00 0.00
ATOM 1025 H   GLU 106 25.099 13.604 44.137 1.00 0.00
ATOM 1026 CA  GLU 106 24.588 13.650 42.104 1.00 13.48
ATOM 1027 CB  GLU 106 23.639 14.802 42.405 1.00 10.05
ATOM 1028 CG  GLU 106 22.364 14.351 43.053 1.00 14.28
ATOM 1029 CD  GLU 106 21.611 13.377 42.175 1.00 22.12
ATOM 1030 OE1 GLU 106 21.330 13.700 41.000 1.00 23.22
ATOM 1031 OE2 GLU 106 21.299 12.273 42.646 1.00 23.74
ATOM 1032 C   GLU 106 25.793 14.130 41.303 1.00 12.12
ATOM 1033 O   GLU 106 26.832 14.451 41.862 1.00 11.30
ATOM 1034 N   ILE 107 25.652 14.180 39.989 1.00 13.18
ATOM 1035 H   ILE 107 24.806 13.903 39.587 1.00 0.00
ATOM 1036 CA  ILE 107 26.758 14.617 39.147 1.00 15.12
ATOM 1037 CB  ILE 107 27.479 13.374 38.500 1.00 14.49
ATOM 1038 CG2 ILE 107 26.531 12.628 37.579 1.00 13.70
ATOM 1039 CG1 ILE 107 28.789 13.770 37.809 1.00 14.83
ATOM 1040 CD1 ILE 107 29.835 14.405 38.728 1.00 8.99
ATOM 1041 C   ILE 107 26.303 15.650 38.107 1.00 16.00
ATOM 1042 O   ILE 107 27.120 16.312 37.484 1.00 19.84
ATOM 1043 N   THR 108 24.998 15.872 38.004 1.00 17.53
ATOM 1044 H   THR 108 24.380 15.392 38.587 1.00 0.00
ATOM 1045 CA  THR 108 24.484 16.836 37.037 1.00 14.06
ATOM 1046 CB  THR 108 23.548 16.172 35.968 1.00 15.28
ATOM 1047 OG1 THR 108 22.448 15.532 36.625 1.00 17.64
ATOM 1048 HG1 THR 108 21.948 16.185 37.099 1.00 0.00
ATOM 1049 CG2 THR 108 24.297 15.130 35.142 1.00 13.09
ATOM 1050 C   THR 108 23.715 17.945 37.731 1.00 15.45
ATOM 1051 O   THR 108 23.231 17.779 38.857 1.00 10.14
ATOM 1052 N   PHE 109 23.560 19.043 37.000 1.00 9.08
ATOM 1053 H   PHE 109 23.958 19.059 36.111 1.00 0.00
ATOM 1054 CA  PHE 109 22.861 20.225 37.447 1.00 9.80
ATOM 1055 CB  PHE 109 23.050 21.293 36.382 1.00 8.07
ATOM 1056 CG  PHE 109 22.144 22.454 36.520 1.00 12.25
ATOM 1057 CD1 PHE 109 22.320 23.372 37.550 1.00 9.93
ATOM 1058 CD2 PHE 109 21.091 22.626 35.630 1.00 12.66
ATOM 1059 CE1 PHE 109 21.456 24.444 37.702 1.00 13.89
ATOM 1060 CE2 PHE 109 20.215 23.699 35.769 1.00 16.94
ATOM 1061 CZ  PHE 109 20.397 24.613 36.810 1.00 15.71
ATOM 1062 C   PHE 109 21.373 19.937 37.687 1.00 16.19
ATOM 1063 O   PHE 109 20.809 20.304 38.727 1.00 16.01
ATOM 1064 N   HIS 110 20.736 19.278 36.719 1.00 15.98
ATOM 1065 H   HIS 110 21.235 19.018 35.931 1.00 0.00
ATOM 1066 CA  HIS 110 19.323 18.948 36.821 1.00 14.96
ATOM 1067 CB  HIS 110 18.750 18.574 35.451 1.00 16.50
ATOM 1068 CG  HIS 110 18.493 19.757 34.578 1.00 20.40
ATOM 1069 CD2 HIS 110 17.485 20.661 34.567 1.00 22.83
ATOM 1070 ND1 HIS 110 19.378 20.168 33.603 1.00 25.49
ATOM 1071 HD1 HIS 110 20.191 19.712 33.331 1.00 0.00
ATOM 1072 CE1 HIS 110 18.926 21.276 33.034 1.00 25.22
ATOM 1073 NE2 HIS 110 17.778 21.591 33.608 1.00 30.14
ATOM 1074 HE2 HIS 110 17.232 22.393 33.401 1.00 0.00
ATOM 1075 C   HIS 110 18.989 17.890 37.864 1.00 12.85
ATOM 1076 O   HIS 110 17.955 17.972 38.497 1.00 14.45
ATOM 1077 N   GLY 111 19.840 16.886 38.022 1.00 9.71
ATOM 1078 H   GLY 111 20.628 16.830 37.470 1.00 0.00
ATOM 1079 CA  GLY 111 19.583 15.866 39.029 1.00 12.89
ATOM 1080 C   GLY 111 19.614 16.517 40.408 1.00 15.28
ATOM 1081 O   GLY 111 18.755 16.296 41.261 1.00 14.53
ATOM 1082 N   ALA 112 20.594 17.386 40.587 1.00 12.94
ATOM 1083 H   ALA 112 21.220 17.557 39.857 1.00 0.00
ATOM 1084 CA  ALA 112 20.775 18.096 41.823 1.00 9.74
ATOM 1085 CB  ALA 112 22.064 18.885 41.767 1.00 13.72
ATOM 1086 C   ALA 112 19.609 19.028 42.031 1.00 11.07
ATOM 1087 O   ALA 112 19.055 19.091 43.123 1.00 15.67
ATOM 1088 N   LYS 113 19.230 19.768 40.997 1.00 8.32
ATOM 1089 H   LYS 113 19.692 19.688 40.144 1.00 0.00
ATOM 1090 CA  LYS 113 18.145 20.701 41.137 1.00 8.53
ATOM 1091 CB  LYS 113 17.987 21.626 39.918 1.00 10.67
ATOM 1092 CG  LYS 113 16.964 22.735 40.104 1.00 7.70
ATOM 1093 CD  LYS 113 16.939 23.720 38.939 1.00 12.62
ATOM 1094 CE  LYS 113 16.476 23.066 37.640 1.00 13.25
ATOM 1095 NZ  LYS 113 15.141 22.417 37.758 1.00 19.14
ATOM 1096 HZ1 LYS 113 14.428 23.131 38.031 1.00 0.00
ATOM 1097 HZ2 LYS 113 15.169 21.679 38.496 1.00 0.00
ATOM 1098 HZ3 LYS 113 14.866 21.988 36.854 1.00 0.00
ATOM 1099 C   LYS 113 16.803 19.988 41.424 1.00 9.66
ATOM 1100 O   LYS 113 16.016 20.454 42.234 1.00 11.59
ATOM 1101 N   GLU 114 16.578 18.850 40.784 1.00 11.24
ATOM 1102 H   GLU 114 17.231 18.529 40.141 1.00 0.00
ATOM 1103 CA  GLU 114 15.369 18.081 41.009 1.00 16.90
ATOM 1127 O   SER 116 14.950 20.960 47.227 1.00 11.86
ATOM 1128 N   LEU 117 14.654 20.651 45.019 1.00 12.30
ATOM 1129 H   LEU 117 15.027 20.299 44.178 1.00 0.00
ATOM 1130 CA  LEU 117 13.294 21.208 45.021 1.00 15.69
ATOM 1131 CB  LEU 117 12.720 21.296 43.594 1.00 12.52
ATOM 1132 CG  LEU 117 13.208 22.443 42.702 1.00 12.20
ATOM 1133 CD1 LEU 117 12.781 22.194 41.230 1.00 12.94
ATOM 1134 CD2 LEU 117 12.679 23.774 43.224 1.00 7.95
ATOM 1135 C   LEU 117 12.321 20.456 45.939 1.00 12.60
ATOM 1136 O   LEU 117 11.234 20.949 46.230 1.00 15.03
ATOM 1137 N   SER 118 12.696 19.258 46.375 1.00 14.56
ATOM 1138 H   SER 118 13.557 18.876 46.094 1.00 0.00
ATOM 1139 CA  SER 118 11.837 18.492 47.270 1.00 14.85
ATOM 1140 CB  SER 118 12.098 16.991 47.140 1.00 11.99
ATOM 1141 OG  SER 118 13.376 16.632 47.651 1.00 19.51
ATOM 1142 HG  SER 118 13.402 16.843 48.592 1.00 0.00
ATOM 1143 C   SER 118 12.051 18.935 48.724 1.00 13.49
ATOM 1144 O   SER 118 11.454 18.378 49.639 1.00 11.93
ATOM 1145 N   TYR 119 12.916 19.920 48.932 1.00 12.03
ATOM 1146 H   TYR 119 13.375 20.336 48.173 1.00 0.00
ATOM 1147 CA  TYR 119 13.193 20.408 50.271 1.00 9.11
ATOM 1148 CB  TYR 119 14.700 20.353 50.570 1.00 10.05
ATOM 1149 CG  TYR 119 15.237 18.950 50.797 1.00 10.85
ATOM 1150 CD1 TYR 119 15.611 18.139 49.718 1.00 9.48
ATOM 1151 CE1 TYR 119 16.043 16.828 49.912 1.00 8.37
ATOM 1152 CD2 TYR 119 15.324 18.408 52.088 1.00 11.10
ATOM 1153 CE2 TYR 119 15.765 17.080 52.295 1.00 8.45
ATOM 1154 CZ  TYR 119 16.114 16.306 51.201 1.00 7.77
ATOM 1155 OH  TYR 119 16.521 15.008 51.373 1.00 10.04
ATOM 1156 HH  TYR 119 16.514 14.774 52.314 1.00 0.00
ATOM 1157 C   TYR 119 12.664 21.819 50.441 1.00 9.59
ATOM 1158 O   TYR 119 12.523 22.566 49.475 1.00 11.29
ATOM 1159 N   SER 120 12.352 22.171 51.680 1.00 10.84
ATOM 1160 H   SER 120 12.469 21.523 52.398 1.00 0.00
ATOM 1161 CA  SER 120 11.843 23.485 51.990 1.00 12.68
ATOM 1162 CB  SER 120 11.317 23.512 53.429 1.00 18.92
ATOM 1163 OG  SER 120 12.284 23.052 54.365 1.00 22.03
ATOM 1164 HG  SER 120 12.495 22.136 54.145 1.00 0.00
ATOM 1165 C   SER 120 12.926 24.535 51.811 1.00 12.21
ATOM 1166 O   SER 120 14.104 24.213 51.844 1.00 12.23
ATOM 1167 N   ALA 121 12.518 25.792 51.651 1.00 12.76
ATOM 1168 H   ALA 121 11.556 25.972 51.644 1.00 0.00
ATOM 1169 CA  ALA 121 13.441 26.914 51.486 1.00 13.79
ATOM 1170 CB  ALA 121 12.663 28.203 51.273 1.00 9.93
ATOM 1171 C   ALA 121 14.415 27.084 52.666 1.00 15.83
ATOM 1172 O   ALA 121 15.554 27.506 52.463 1.00 18.89
ATOM 1173 N   GLY 122 13.962 26.792 53.889 1.00 14.13
ATOM 1174 H   GLY 122 13.040 26.488 54.008 1.00 0.00
ATOM 1175 CA  GLY 122 14.821 26.921 55.059 1.00 9.48
```

-continued

```
ATOM 1104 CB LGU 114 15.333 16.851 40.110 1.00 24.56      ATOM 1176 C GLY 122 15.946 25.902 55.039 1.00 8.10
ATOM 1105 CG GLU 114 14.960 17.113 38.673 1.00 43.69      ATOM 1177 O GLY 122 17.100 26.236 55.336 1.00 11.50
ATOM 1106 CD GLU 114 15.300 15.930 37.759 1.00 54.79      ATOM 1178 N ALA 123 15.603 24.662 54.680 1.00 6.93
ATOM 1107 OE1 GLU 114 15.628 16.176 36.571 1.00 60.55     ATOM 1179 H ALA 123 14.660 24.480 54.491 1.00 0.00
ATOM 1108 OE2 GLU 114 15.249 14.763 38.227 1.00 58.35     ATOM 1180 CA ALA 123 16.551 23.544 54.575 1.00 9.25
ATOM 1109 C GLU 114 15.276 17.625 42.465 1.00 15.80       ATOM 1181 CB ALA 123 15.803 22.246 54.325 1.00 6.69
ATOM 1110 O GLU 114 14.244 17.810 43.107 1.00 13.65       ATOM 1182 C ALA 123 17.526 23.777 53.437 1.00 10.15
ATOM 1111 N ILE 115 16.337 17.033 43.004 1.00 15.64       ATOM 1183 O ALA 123 18.701 23.431 53.536 1.00 10.03
ATOM 1112 H ILE 115 17.150 16.882 42.469 1.00 0.00        ATOM 1184 N LEU 124 17.011 24.318 52.335 1.00 10.82
ATOM 1113 CA ILE 115 16.255 16.586 44.392 1.00 16.89      ATOM 1185 H LEU 124 16.052 24.510 52.299 1.00 0.00
ATOM 1114 CB ILE 115 17.397 15.623 44.819 1.00 21.22      ATOM 1186 CA LEU 124 17.836 24.613 51.167 1.00 12.02
ATOM 1115 CG2 ILE 115 17.563 14.496 43.815 1.00 21.57     ATOM 1187 CB LEU 124 16.990 25.058 49.962 1.00 11.24
ATOM 1116 CG1 ILE 115 18.711 16.364 44.988 1.00 20.64     ATOM 1188 CG LEU 124 16.325 23.982 49.101 1.00 14.10
ATOM 1117 CD1 ILE 115 19.734 15.522 45.686 1.00 29.19     ATOM 1189 CD1 LEU 124 15.593 24.623 47.938 1.00 17.23
ATOM 1118 C ILE 115 16.156 17.727 45.389 1.00 14.46       ATOM 1190 CD2 LEU 124 17.351 23.015 48.587 1.00 10.37
ATOM 1119 O ILE 115 15.472 17.604 46.407 1.00 14.58       ATOM 1191 C LEU 124 18.855 25.676 51.479 1.00 5.00
ATOM 1120 N SER 116 16.818 18.843 45.102 1.00 11.91       ATOM 1192 O LEU 124 20.022 25.531 51.122 1.00 5.96
ATOM 1121 H SER 116 17.334 18.909 44.269 1.00 0.00        ATOM 1193 N ALA 125 18.421 26.735 52.159 1.00 8.88
ATOM 1122 CA SER 116 16.783 19.989 46.014 1.00 11.85      ATOM 1194 H ALA 125 17.479 26.790 52.419 1.00 0.00
ATOM 1123 CB SER 116 17.802 21.065 45.595 1.00 13.41      ATOM 1195 CA ALA 125 19.324 27.837 52.511 1.00 8.18
ATOM 1124 OG SER 116 19.140 20.570 45.629 1.00 11.32      ATOM 1196 CB ALA 125 18.549 29.018 53.405 1.00 7.28
ATOM 1125 HG SER 116 19.214 19.817 45.010 1.00 0.00       ATOM 1197 C ALA 125 20.369 27.344 53.485 1.00 8.63
ATOM 1126 C SER 116 15.381 20.589 46.133 1.00 12.95       ATOM 1198 O ALA 125 21.541 27.738 53.422 1.00 9.42
ATOM 1199 N SER 126 19.935 26.499 54.412 1.00 10.67       ATOM 1271 N ARG 134 32.044 25.285 53.886 1.00 12.45
ATOM 1200 H SER 126 18.989 26.257 54.447 1.00 0.00        ATOM 1272 H ARG 134 31.389 25.519 53.205 1.00 0.00
ATOM 1201 CA SER 126 20.850 25.942 55.388 1.00 12.02      ATOM 1273 CA ARG 134 32.891 24.120 53.657 1.00 9.53
ATOM 1202 CB SER 126 20.067 25.160 56.449 1.00 14.88      ATOM 1274 CB ARG 134 34.363 24.527 53.513 1.00 10.66
ATOM 1203 OG SER 126 20.917 26.641 57.470 1.00 22.88      ATOM 1275 CG ARG 134 34.705 25.392 52.285 1.00 19.69
ATOM 1204 HG SER 126 21.565 24.046 57.075 1.00 0.00       ATOM 1276 CD ARG 134 36.223 25.622 52.219 1.00 27.89
ATOM 1205 C SER 126 21.876 25.051 54.668 1.00 7.89        ATOM 1277 NE ARG 134 36.693 26.537 51.168 1.00 25.68
ATOM 1206 O SER 126 23.053 25.071 54.983 1.00 10.56       ATOM 1278 HE ARG 134 36.899 26.153 50.297 1.00 0.00
ATOM 1207 N CYS 127 21.426 24.276 53.688 1.00 9.41        ATOM 1279 CZ ARG 134 36.874 27.853 51.323 1.00 29.12
ATOM 1208 H CYS 127 20.478 24.291 53.455 1.00 0.00        ATOM 1280 NH1 ARG 134 36.603 28.446 52.481 1.00 25.56
ATOM 1209 CA CYS 127 22.331 23.407 52.948 1.00 6.08       ATOM 1281 HH11 ARG 134 36.263 27.920 53.223 1.00 0.00
ATOM 1210 CB CYS 127 21.539 22.557 51.957 1.00 4.91       ATOM 1282 HH12 ARG 134 36.739 29.431 52.593 1.00 0.00
ATOM 1211 SG CYS 127 22.497 21.234 51.199 1.00 10.63      ATOM 1283 NH2 ARG 134 37.443 28.569 50.354 1.00 25.85
ATOM 1212 C CYS 127 23.383 24.279 52.247 1.00 7.67        ATOM 1284 HH21 ARG 134 37.733 28.125 49.511 1.00 0.00
ATOM 1213 O CYS 127 24.580 23.977 52.284 1.00 11.04       ATOM 1285 HH22 ARG 134 37.574 29.556 50.473 1.00 0.00
ATOM 1214 N MET 128 22.948 25.395 51.661 1.00 5.72        ATOM 1286 C ARG 134 32.734 23.012 54.710 1.00 11.97
ATOM 1215 H MET 128 21.991 25.610 51.675 1.00 0.00        ATOM 1287 O ARG 134 33.682 22.310 55.041 1.00 12.26
ATOM 1216 CA MET 128 23.869 26.305 50.992 1.00 7.03       ATOM 1288 N MET 135 31.549 22.895 55.289 1.00 10.32
ATOM 1217 CB MET 128 23.119 27.473 50.327 1.00 5.99       ATOM 1289 H MET 135 30.838 23.533 55.085 1.00 0.00
ATOM 1218 CG MET 128 22.413 27.133 48.981 1.00 8.59       ATOM 1290 CA MET 135 31.304 21.812 56.228 1.00 13.20
ATOM 1219 SD MET 128 21.495 28.555 48.317 1.00 11.63      ATOM 1291 CB MET 135 30.159 22.159 57.172 1.00 9.31
ATOM 1220 CE MET 128 22.764 29.725 48.392 1.00 13.39      ATOM 1292 CG MET 135 30.484 23.321 58.095 1.00 16.72
ATOM 1221 C MET 128 24.880 26.836 51.999 1.00 9.78        ATOM 1293 SD MET 135 29.594 23.266 59.649 1.00 18.85
ATOM 1222 O MET 128 26.051 27.000 51.677 1.00 12.00       ATOM 1294 CE MET 135 30.752 22.203 30.639 1.00 7.14
ATOM 1223 N GLY 129 24.431 27.138 53.211 1.00 9.57        ATOM 1295 C MET 135 30.956 20.577 55.386 1.00 16.58
ATOM 1224 H GLY 129 23.483 27.039 53.433 1.00 0.00        ATOM 1296 O MET 135 30.794 19.473 55.908 1.00 18.62
ATOM 1225 CA GLY 129 25.363 27.615 54.217 1.00 12.54      ATOM 1297 N GLY 136 30.788 20.789 54.081 1.00 13.75
ATOM 1226 C GLY 129 26.402 26.546 54.541 1.00 15.15       ATOM 1298 H GLY 136 30.868 21.694 53.723 1.00 0.00
ATOM 1227 O GLY 129 27.584 26.824 54.699 1.00 15.41       ATOM 1299 CA GLY 136 30.497 19.698 53.168 1.00 9.23
ATOM 1228 N LEU 130 25.958 25.298 54.583 1.00 16.07       ATOM 1300 C GLY 136 30.952 20.130 51.786 1.00 9.05
ATOM 1229 H LEU 130 25.003 25.137 54.414 1.00 0.00        ATOM 1301 O GLY 136 31.220 21.312 51.595 1.00 10.44
ATOM 1230 CA LEU 130 26.815 24.165 54.874 1.00 14.53      ATOM 1302 N ALA 137 31.084 19.199 50.841 1.00 8.78
ATOM 1231 CB LEU 130 25.933 22.928 54.933 1.00 13.30      ATOM 1303 H ALA 137 30.881 18.270 51.062 1.00 0.00
ATOM 1232 CG LEU 130 26.499 21.651 55.501 1.00 19.80      ATOM 1304 CA ALA 137 31.502 19.538 49.478 1.00 7.06
ATOM 1233 CD1 LEU 130 25.340 20.802 55.983 1.00 20.50     ATOM 1305 CB ALA 137 33.003 19.352 49.309 1.00 7.32
ATOM 1234 CD2 LEU 130 27.298 20.934 54.411 1.00 19.97     ATOM 1306 C ALA 137 30.771 18.725 48.432 1.00 7.65
ATOM 1235 C LEU 130 27.939 24.019 53.830 1.00 14.41       ATOM 1307 O ALA 137 30.471 17.556 48.655 1.00 11.86
ATOM 1236 O LEU 130 29.094 23.766 54.166 1.00 11.24       ATOM 1308 N VAL 138 30.430 19.380 47.318 1.00 12.92
ATOM 1237 N ILE 131 27.587 24.165 52.561 1.00 12.46       ATOM 1309 H VAL 138 30.650 20.336 47.254 1.00 0.00
ATOM 1238 H ILE 131 26.645 24.335 52.344 1.00 0.00        ATOM 1310 CA VAL 138 29.747 18.761 46.169 1.00 10.65
ATOM 1239 CA ILE 131 28.564 24.077 51.486 1.00 13.33      ATOM 1311 CB VAL 138 28.233 19.106 46.136 1.00 7.32
ATOM 1240 CB ILE 131 27.865 23.949 50.094 1.00 10.82      ATOM 1312 CG1 VAL 138 27.493 18.422 47.301 1.00 4.42
ATOM 1241 CG2 ILE 131 28.915 23.970 48.988 1.00 17.49     ATOM 1313 CG2 VAL 138 27.999 20.624 46.176 1.00 3.67
ATOM 1242 CG1 ILE 131 27.041 22.660 50.003 1.00 7.85      ATOM 1314 C VAL 138 30.418 19.307 44.894 1.00 12.61
ATOM 1243 CD1 ILE 131 27.848 21.407 50.068 1.00 10.42     ATOM 1315 O VAL 138 31.216 20.247 44.964 1.00 13.30
ATOM 1244 C ILE 131 29.435 25.351 51.500 1.00 11.32       ATOM 1316 N THR 139 30.145 18.712 43.739 1.00 12.53
ATOM 1245 O ILE 131 30.660 25.288 51.398 1.00 9.76        ATOM 1317 H THR 139 29.567 17.932 43.720 1.00 0.00
ATOM 1246 N TYR 132 28.802 26.507 51.661 1.00 11.05       ATOM 1318 CA THR 139 30.736 19.226 42.501 1.00 11.01
ATOM 1247 H TYR 132 27.836 26.500 51.763 1.00 0.00        ATOM 1319 CB THR 139 30.513 18.262 41.344 1.00 9.71
ATOM 1248 CA TYR 132 29.512 27.778 51.688 1.00 13.75      ATOM 1320 OG1 THR 139 29.132 17.898 41.284 1.00 11.98
ATOM 1249 CB TYR 132 28.529 28.913 51.985 1.00 13.06      ATOM 1321 HG1 THR 139 28.888 17.482 42.106 1.00 0.00
ATOM 1250 CG TYR 132 29.177 30.277 51.998 1.00 14.32      ATOM 1322 CG2 THR 139 31.336 17.015 41.535 1.00 13.10
ATOM 1251 CD1 TYR 132 29.758 30.824 50.833 1.00 8.32      ATOM 1323 C THR 139 30.085 20.574 42.189 1.00 8.25
ATOM 1252 CE1 TYR 132 30.405 32.063 50.869 1.00 7.98      ATOM 1324 O THR 139 28.966 20.822 42.616 1.00 10.07
ATOM 1253 CD2 TYR 132 29.258 31.002 53.183 1.00 9.90      ATOM 1325 N THR 140 30.767 21.419 41.422 1.00 8.47
ATOM 1254 CE2 TYR 132 29.893 32.218 53.230 1.00 8.74      ATOM 1326 H THR 140 31.639 21.135 41.069 1.00 0.00
```

-continued

```
ATOM   1255  CZ   TYR  132  30.464  32.752  52.088  1.00  10.10
ATOM   1256  OH   TYR  132  31.066  33.981  52.240  1.00  10.50
ATOM   1257  HH   TYR  132  31.388  34.204  51.423  1.00  0.00
ATOM   1258  C    TYR  132  30.618  27.792  52.735  1.00  14.84
ATOM   1259  O    TYR  132  31.732  28.260  52.487  1.00  12.02
ATOM   1260  N    ASN  133  30.275  27.294  53.917  1.00  16.11
ATOM   1261  H    ASN  133  29.374  26.944  54.032  1.00  0.00
ATOM   1262  CA   ASN  133  31.187  27.235  55.041  1.00  14.06
ATOM   1263  CB   ASN  133  30.401  27.245  56.347  1.00  10.32
ATOM   1264  CG   ASN  133  29.832  28.617  56.664  1.00  13.22
ATOM   1265  OD1  ASN  133  30.543  26.609  56.630  1.00  14.06
ATOM   1266  ND2  ASN  133  28.541  28.676  56.968  1.00  12.50
ATOM   1267  HD21 ASN  133  28.008  27.858  56.963  1.00  0.00
ATOM   1268  HD22 ASN  133  28.172  29.568  57.155  1.00  0.00
ATOM   1269  C    ASN  133  32.130  26.043  57.976  1.00  11.53
ATOM   1270  O    ASN  133  32.919  25.824  55.887  1.00  12.37
ATOM   1343  O    GLU  141  25.043  21.915  39.564  1.00  7.25
ATOM   1344  N    VAL  142  26.520  20.640  40.689  1.00  10.61
ATOM   1345  H    VAL  142  27.444  20.317  40.736  1.00  0.00
ATOM   1346  CA   VAL  142  25.561  20.153  41.672  1.00  8.00
ATOM   1347  CB   VAL  142  26.127  18.894  42.411  1.00  7.01
ATOM   1348  CG1  VAL  142  25.362  18.605  43.682  1.00  9.50
ATOM   1349  CG2  VAL  142  26.025  17.685  41.521  1.00  6.00
ATOM   1350  C    VAL  142  25.260  21.332  42.625  1.00  9.83
ATOM   1351  O    VAL  142  24.101  21.575  42.982  1.00  11.75
ATOM   1352  N    ALA  143  23.293  22.110  42.967  1.00  9.16
ATOM   1353  H    ALA  143  27.180  21.895  42.609  1.00  0.00
ATOM   1354  CA   ALA  143  26.137  23.270  43.840  1.00  6.52
ATOM   1355  CB   ALA  143  27.502  23.882  44.171  1.00  5.45
ATOM   1356  C    ALA  143  25.255  24.296  43.129  1.00  11.05
ATOM   1357  O    ALA  143  24.456  24.986  43.763  1.00  12.06
ATOM   1358  N    PHE  144  25.403  24.402  41.807  1.00  12.68
ATOM   1359  H    PHE  144  26.066  23.849  41.353  1.00  0.00
ATOM   1360  CA   PHE  144  24.598  25.333  41.020  1.00  6.76
ATOM   1361  CB   PHE  144  25.059  25.377  39.551  1.00  7.23
ATOM   1362  CG   PHE  144  26.392  26.061  39.325  1.00  8.19
ATOM   1363  CD1  PHE  144  27.163  25.735  38.222  1.00  9.21
ATOM   1364  CD2  PHE  144  26.857  27.048  40.189  1.00  11.80
ATOM   1365  CE1  PHE  144  28.379  26.382  37.979  1.00  8.34
ATOM   1366  CE2  PHE  144  28.073  27.697  39.954  1.00  10.30
ATOM   1367  CZ   PHE  144  28.829  27.366  38.850  1.00  10.79
ATOM   1368  C    PHE  144  23.133  24.890  41.083  1.00  6.24
ATOM   1369  O    PHE  144  22.243  25.718  41.224  1.00  10.40
ATOM   1370  N    GLY  145  22.889  23.588  40.944  1.00  7.95
ATOM   1371  H    GLY  145  23.638  22.971  40.806  1.00  0.00
ATOM   1372  CA   GLY  145  21.532  23.064  41.007  1.00  9.52
ATOM   1373  C    GLY  145  20.878  23.367  42.360  1.00  13.71
ATOM   1374  O    GLY  145  19.689  23.669  42.440  1.00  16.36
ATOM   1375  N    LEU  146  21.654  23.283  43.435  1.00  11.72
ATOM   1376  H    LEU  146  22.592  23.012  43.323  1.00  0.00
ATOM   1377  CA   LEU  146  21.155  23.588  44.768  1.00  9.87
ATOM   1378  CB   LEU  146  22.230  23.268  45.821  1.00  6.53
ATOM   1379  CG   LEU  146  22.049  23.850  47.227  1.00  3.71
ATOM   1380  CD1  LEU  146  20.866  23.208  47.910  1.00  4.97
ATOM   1381  CD2  LEU  146  23.301  23.644  48.048  1.00  6.08
ATOM   1382  C    LEU  146  20.759  25.079  44.853  1.00  12.57
ATOM   1383  O    LEU  146  19.643  25.416  45.281  1.00  12.75
ATOM   1384  N    VAL  147  21.656  25.983  44.457  1.00  12.23
ATOM   1385  H    VAL  147  22.537  25.704  44.130  1.00  0.00
ATOM   1386  CA   VAL  147  21.300  27.398  44.534  1.00  12.12
ATOM   1387  CB   VAL  147  22.516  28.366  44.375  1.00  14.02
ATOM   1388  CG1  VAL  147  23.239  28.131  43.103  1.00  13.40
ATOM   1389  CG2  VAL  147  22.054  29.816  44.466  1.00  14.74
ATOM   1390  C    VAL  147  20.158  27.731  43.590  1.00  13.59
ATOM   1391  O    VAL  147  19.328  28.573  43.917  1.00  13.65
ATOM   1392  N    CYS  148  20.075  27.044  42.445  1.00  12.84
ATOM   1393  H    CYS  148  20.752  26.372  42.236  1.00  0.00
ATOM   1394  CA   CYS  148  18.977  27.292  41.496  1.00  13.53
ATOM   1395  CB   CYS  148  19.293  26.725  40.106  1.00  6.40
ATOM   1396  SG   CYS  148  20.564  27.738  39.334  1.00  11.77
ATOM   1397  C    CYS  148  17.617  26.812  42.018  1.00  12.91
ATOM   1398  O    CYS  148  16.601  27.460  41.790  1.00  15.45
ATOM   1399  N    ALA  149  17.604  25.684  42.726  1.00  17.88
ATOM   1400  H    ALA  149  18.438  25.186  42.845  1.00  0.00
ATOM   1401  CA   ALA  149  16.380  25.156  43.329  1.00  15.13
ATOM   1402  CB   ALA  149  16.648  23.807  43.981  1.00  9.57
ATOM   1403  C    ALA  149  15.904  26.160  44.386  1.00  15.41
ATOM   1404  O    ALA  149  14.718  26.471  44.472  1.00  17.40
ATOM   1405  N    THR  150  16.843  26.687  45.167  1.00  14.69
ATOM   1327  CA   THR  140  30.278  22.754  41.072  1.00  10.58
ATOM   1328  CB   THR  140  31.245  23.459  40.094  1.00  11.37
ATOM   1329  OG1  THR  140  32.573  23.362  40.589  1.00  19.59
ATOM   1330  HG1  THR  140  32.634  23.764  41.459  1.00  0.00
ATOM   1331  CG2  THR  140  30.933  24.928  39.970  1.00  11.42
ATOM   1332  C    THR  140  28.886  22.814  40.458  1.00  9.63
ATOM   1333  O    THR  140  28.068  23.645  80.844  1.00  9.01
ATOM   1334  N    GLU  141  28.627  21.954  39.483  1.00  8.40
ATOM   1335  H    GLU  141  29.300  21.295  39.233  1.00  0.00
ATOM   1336  CA   GLU  141  27.336  21.948  38.800  1.00  10.65
ATOM   1337  CB   GLU  141  27.426  21.090  37.530  1.00  13.62
ATOM   1338  CG   GLU  141  28.579  21.501  36.566  1.00  10.12
ATOM   1339  CD   GLU  141  29.953  21.031  37.030  1.00  10.60
ATOM   1340  OE1  GLU  141  30.046  19.981  37.684  1.00  16.76
ATOM   1341  OE2  GLU  141  30.952  21.713  36.755  1.00  17.34
ATOM   1342  C    GLU  141  26.188  21.494  39.722  1.00  9.83
ATOM   1415  H    CYS  151  17.337  29.032  44.202  1.00  0.00
ATOM   1416  CA   CYS  151  15.981  30.618  43.803  1.00  11.02
ATOM   1417  CB   CYS  151  16.856  30.947  42.605  1.00  8.67
ATOM   1418  SG   CYS  151  18.366  31.666  43.084  1.00  15.75
ATOM   1419  C    CYS  151  14.603  30.340  43.285  1.00  11.21
ATOM   1420  O    CYS  151  13.723  31.167  43.379  1.00  15.23
ATOM   1421  N    GLU  152  14.445  29.179  42.676  1.00  12.23
ATOM   1422  H    GLU  152  15.206  28.570  42.595  1.00  0.00
ATOM   1423  CA   GLU  152  13.170  28.772  42.138  1.00  17.47
ATOM   1424  CB   GLU  152  13.330  27.415  41.456  1.00  15.93
ATOM   1425  CG   GLU  152  12.115  26.929  40.717  1.00  21.04
ATOM   1426  CD   GLU  152  12.413  25.747  39.816  1.00  24.99
ATOM   1427  OE1  GLU  152  13.578  25.306  39.752  1.00  25.94
ATOM   1428  OE2  GLU  152  11.476  25.259  39.155  1.00  32.48
ATOM   1429  C    GLU  152  12.116  28.737  43.266  1.00  22.62
ATOM   1430  O    GLU  152  11.021  29.287  43.106  1.00  21.98
ATOM   1431  N    GLN  153  12.457  28.143  44.414  1.00  22.64
ATOM   1432  H    GLN  153  13.345  27.752  44.504  1.00  0.00
ATOM   1433  CA   GLN  153  11.522  28.077  45.539  1.00  22.96
ATOM   1434  CB   GLN  153  12.133  27.336  46.735  1.00  25.41
ATOM   1435  CG   GLN  153  12.473  25.881  46.509  1.00  26.48
ATOM   1436  CD   GLN  153  11.257  24.984  46.406  1.00  26.11
ATOM   1437  OE1  GLN  153  10.405  25.159  45.530  1.00  30.11
ATOM   1438  NE2  GLN  153  11.210  23.971  47.249  1.00  24.58
ATOM   1439  HE21 GLN  153  11.947  23.833  47.892  1.00  0.00
ATOM   1440  HE22 GLN  153  10.447  23.371  47.205  1.00  0.00
ATOM   1441  C    GLN  153  11.135  29.483  45.990  1.00  23.13
ATOM   1442  O    GLN  153  9.957   29.789  46.153  1.00  27.09
ATOM   1443  N    ILE  154  12.134  30.341  46.158  1.00  23.64
ATOM   1444  H    ILE  154  13.048  30.044  45.970  1.00  0.00
ATOM   1445  CA   ILE  154  11.931  31.713  46.646  1.00  24.34
ATOM   1446  CB   ILE  154  13.286  32.426  46.899  1.00  26.55
ATOM   1447  CG2  ILE  154  13.046  33.849  47.393  1.00  29.89
ATOM   1448  CG1  ILE  154  14.092  31.664  47.948  1.00  26.58
ATOM   1449  CD1  ILE  154  15.382  32.348  48.310  1.00  27.39
ATOM   1450  C    ILE  154  11.147  32.565  45.630  1.00  23.64
ATOM   1451  O    ILE  154  10.274  33.345  46.018  1.00  23.27
ATOM   1452  N    ALA  155  11.486  32.445  44.357  1.00  22.50
ATOM   1453  H    ALA  155  12.197  31.832  44.107  1.00  0.00
ATOM   1454  CA   ALA  155  10.816  33.216  43.326  1.00  24.60
ATOM   1455  CB   ALA  155  11.469  32.957  41.959  1.00  15.01
ATOM   1456  C    ALA  155  9.330   32.867  43.303  1.00  25.67
ATOM   1457  O    ALA  155  8.488   33.752  43.229  1.00  26.42
ATOM   1458  N    ASP  156  9.019   31.583  43.458  1.00  30.93
ATOM   1459  H    ASP  156  9.740   30.926  43.585  1.00  0.00
ATOM   1460  CA   ASP  156  7.634   31.118  43.445  1.00  36.44
ATOM   1461  CB   ASP  156  7.753   29.600  43.310  1.00  42.76
ATOM   1462  CG   ASP  156  8.105   29.112  41.959  1.00  49.60
ATOM   1463  OD1  ASP  156  8.003   29.818  40.946  1.00  54.15
ATOM   1464  OD2  ASP  156  8.647   28.010  41.874  1.00  53.52
ATOM   1465  C    ASP  156  6.820   31.577  44.642  1.00  37.91
ATOM   1466  O    ASP  156  5.595   31.622  44.567  1.00  38.75
ATOM   1467  N    SER  157  7.487   31.906  45.746  1.00  36.87
ATOM   1468  H    SER  157  8.453   31.806  45.770  1.00  0.00
ATOM   1469  CA   SER  157  6.788   32.397  46.939  1.00  36.20
ATOM   1470  CB   SER  157  7.691   32.313  48.184  1.00  30.91
ATOM   1471  OG   SER  157  8.608   33.394  48.273  1.00  16.54
ATOM   1472  HG   SER  157  9.181   33.403  47.503  1.00  0.00
ATOM   1473  C    SER  157  6.347   33.854  46.696  1.00  41.61
ATOM   1474  O    SER  157  5.419   34.354  47.344  1.00  38.48
ATOM   1475  N    GLN  158  7.050   34.525  45.783  1.00  47.31
ATOM   1476  H    GLN  158  7.786   34.078  45.331  1.00  0.00
ATOM   1477  CA   GLN  158  6.771   35.909  45.409  1.00  52.71
```

-continued

```
ATOM 1406 H THR 150 17.780 26.411 45.057 1.00 0.00      ATOM 1478 CB GLN 158 8.006 36.526 44.739 1.00 51.04
ATOM 1407 CA THR 150 16.516 27.672 46.198 1.00 15.98    ATOM 1479 CG GLN 158 9.288 36.477 45.567 1.00 49.19
ATOM 1408 CB THR 150 17.751 28.068 47.011 1.00 13.74    ATOM 1480 CD GLN 158 10.540 36.886 44.779 1.00 48.92
ATOM 1409 OG1 THR 150 18.472 26.881 47.370 1.00 15.40   ATOM 1481 OE1 GLN 158 10.489 37.188 43.583 1.00 46.55
ATOM 1410 HG1 THR 150 17.908 26.319 47.899 1.00 0.00    ATOM 1482 NE2 GLN 158 11.672 36.891 45.459 1.00 48.60
ATOM 1411 CG2 THR 150 17.330 28.823 48.286 1.00 18.44   ATOM 1483 HE21 GLN 158 11.666 36.647 46.402 1.00 0.00
ATOM 1412 C THR 150 15.895 28.920 45.585 1.00 14.15     ATOM 1484 HE22 GLN 158 12.481 37.152 44.965 1.00 0.00
ATOM 1413 O THR 150 14.891 29.408 46.085 1.00 18.21     ATOM 1485 C GLN 158 5.558 36.009 44.455 1.00 58.48
ATOM 1414 N CYS 151 16.501 29.443 44.518 1.00 14.47     ATOM 1486 O GLN 158 4.951 37.104 44.376 1.00 61.29
ATOM 1487 OT GLN 158 5.217 35.003 43.784 1.00 62.85     ATOM 1559 CG2 THR 209 42.205 23.739 85.218 1.00 23.14
ATOM 1488 CB SER 202 36.503 31.482 88.093 1.00 45.76    ATOM 1560 C THR 209 41.763 22.320 81.650 1.00 15.53
ATOM 1489 OG SER 202 37.808 31.091 87.693 1.00 43.89    ATOM 1561 O THR 209 42.573 21.507 81.209 1.00 19.41
ATOM 1490 HG SER 202 38.263 30.678 88.441 1.00 0.00     ATOM 1562 N TYR 210 40.511 22.370 81.214 1.00 13.91
ATOM 1491 C SER 202 35.492 29.342 87.320 1.00 42.83     ATOM 1563 H TYR 210 39.880 23.019 81.592 1.00 0.00
ATOM 1492 O SER 202 36.292 28.427 87.125 1.00 40.83     ATOM 1564 CA TYR 210 40.092 21.444 80.173 1.00 12.82
ATOM 1493 HT1 SER 202 37.295 29.247 89.283 1.00 0.00    ATOM 1565 CB TYR 210 38.594 21.556 79.899 1.00 13.43
ATOM 1494 HT2 SER 202 35.803 28.722 89.898 1.00 0.00    ATOM 1566 CG TYR 210 37.728 20.773 80.845 1.00 11.53
ATOM 1495 N SER 202 36.367 29.547 89.639 1.00 45.24     ATOM 1567 CD1 TYR 210 37.038 21.412 81.883 1.00 12.85
ATOM 1496 HT3 SER 202 36.479 30.200 90.432 1.00 0.00    ATOM 1568 CE1 TYR 210 36.185 20.686 82.735 1.00 11.80
ATOM 1497 CA SER 202 35.672 30.268 88.522 1.00 44.26    ATOM 1569 CD2 TYR 210 37.559 19.392 80.678 1.00 10.21
ATOM 1498 N LEU 203 34.479 29.616 86.490 1.00 39.07     ATOM 1570 CE2 TYR 210 36.712 18.657 81.516 1.00 7.26
ATOM 1499 H LEU 203 33.890 30.381 86.690 1.00 0.00      ATOM 1571 CZ TYR 210 36.025 19.310 82.539 1.00 7.27
ATOM 1500 CA LEU 203 34.231 28.798 85.311 1.00 34.20    ATOM 1572 OH TYR 210 35.154 18.589 83.325 1.00 7.76
ATOM 1501 CB LEU 203 32.999 29.288 84.556 1.00 33.82    ATOM 1573 HH TYR 210 34.749 19.169 83.973 1.00 0.00
ATOM 1502 CG LEU 203 32.147 28.180 83.921 1.00 33.57    ATOM 1574 C TYR 210 40.861 21.792 78.907 1.00 12.95
ATOM 1503 CD1 LEU 203 31.308 28.746 82.779 1.00 30.93   ATOM 1575 O TYR 210 41.433 20.925 78.261 1.00 13.94
ATOM 1504 CD2 LEU 203 33.024 27.039 43.413 1.00 37.57   ATOM 1576 N VAL 211 40.890 23.069 78.561 1.00 15.03
ATOM 1505 C LEU 203 35.441 28.890 84.388 1.00 31.19     ATOM 1577 H VAL 211 40.443 23.706 79.118 1.00 0.00
ATOM 1506 O LEU 203 35.972 27.873 83.940 1.00 30.08     ATOM 1578 CA VAL 211 41.589 23.509 77.362 1.00 16.63
ATOM 1507 N LEU 204 35.909 30.117 84.174 1.00 27.77     ATOM 1579 CB VAL 211 41.417 25.043 77.137 1.00 16.75
ATOM 1508 H LEU 204 35.472 30.881 84.586 1.00 0.00      ATOM 1580 CG1 VAL 211 42.283 25.522 75.999 1.00 13.39
ATOM 1509 CA LEU 204 37.053 30.373 83.311 1.00 26.50    ATOM 1581 CG2 VAL 211 39.966 25.651 78.801 1.00 6.94
ATOM 1510 CB LEU 204 37.363 31.872 83.243 1.00 27.74    ATOM 1582 C VAL 211 43.061 23.090 77.356 1.00 18.10
ATOM 1511 CG LEU 204 36.361 32.735 82.450 1.00 33.57    ATOM 1583 O VAL 211 43.530 22.481 76.384 1.00 19.38
ATOM 1512 CD1 LEU 204 36.818 34.183 82.453 1.00 34.61   ATOM 1584 N LEU 212 43.765 23.321 78.463 1.00 16.58
ATOM 1513 CD2 LEU 204 36.201 32.240 80.998 1.00 30.17   ATOM 1585 H LEU 212 43.332 23.744 79.224 1.00 0.00
ATOM 1514 C LEU 204 38.286 29.571 83.692 1.00 24.23     ATOM 1586 CA LEU 212 45.176 22.958 78.540 1.00 12.67
ATOM 1515 O LEU 204 39.069 29.190 82.823 1.00 24.00     ATOM 1587 CB LEU 212 45.816 23.527 79.804 1.00 17.11
ATOM 1516 N THR 205 38.432 29.260 84.975 1.00 22.66     ATOM 1588 CG LEU 212 45.843 25.052 79.896 1.00 21.80
ATOM 1517 H THR 205 37.771 29.545 85.623 1.00 0.00      ATOM 1589 CD1 LEU 212 46.459 25.467 81.212 1.00 23.26
ATOM 1518 CA THR 205 39.574 28.467 85.416 1.00 22.80    ATOM 1590 CD2 LEU 212 46.636 25.630 78.739 1.00 21.56
ATOM 1519 CB THR 205 39.830 28.604 86.927 1.00 23.16    ATOM 1591 C LEU 212 45.435 21.471 78.472 1.00 12.30
ATOM 1520 OG1 THR 205 40.291 29.933 87.211 1.00 27.63   ATOM 1592 O LEU 212 46.508 21.056 78.063 1.00 17.88
ATOM 1521 HG1 THR 205 39.637 30.576 86.910 1.00 0.00    ATOM 1593 N SER 213 44.450 20.655 78.815 1.00 14.49
ATOM 1522 CG2 THR 205 40.868 27.601 87.402 1.00 21.83   ATOM 1594 H SER 213 43.577 21.018 79.074 1.00 0.00
ATOM 1523 C THR 205 39.338 27.015 85.046 1.00 21.86     ATOM 1595 CA SER 213 44.648 19.209 78.799 1.00 14.39
ATOM 1524 O THR 205 40.260 26.308 74.638 1.00 21.85     ATOM 1596 CB SER 213 43.479 18.495 79.472 1.00 13.96
ATOM 1525 N GLU 206 38.086 26.588 85.126 1.00 22.68     ATOM 1597 OG SER 213 42.325 18.512 78.665 1.00 18.43
ATOM 1526 H GLU 206 37.373 27.199 85.410 1.00 0.00      ATOM 1598 HG SER 213 42.078 19.380 78.505 1.00 0.00
ATOM 1527 CA GLU 206 37.752 25.220 84.786 1.00 21.05    ATOM 1599 C SER 213 44.916 18.585 77.437 1.00 15.86
ATOM 1528 CB GLU 206 36.322 24.908 85.166 1.00 21.51    ATOM 1600 O SER 213 45.407 17.464 77.363 1.00 15.00
ATOM 1529 CG GLU 206 35.980 23.454 84.934 1.00 19.38    ATOM 1601 N ILE 214 44.562 19.274 76.357 1.00 18.77
ATOM 1530 CD GLU 206 34.672 23.065 85.548 1.00 21.36    ATOM 1602 H ILE 214 44.136 20.152 76.455 1.00 0.00
ATOM 1531 OE1 GLU 206 34.314 21.880 85.431 1.00 23.08   ATOM 1603 CA ILE 214 44.815 18.717 75.026 1.00 21.44
ATOM 1532 OE2 GLU 206 33.996 23.942 86.144 1.00 26.46   ATOM 1604 CB ILE 214 43.693 19.069 74.001 1.00 19.51
ATOM 1533 C GLU 206 37.930 24.992 83.296 1.00 21.34     ATOM 1605 CG2 ILE 214 42.354 18.547 74.470 1.00 14.52
ATOM 1534 O GLU 206 38.400 23.934 82.868 1.00 21.36     ATOM 1606 CG1 ILE 214 43.663 20.575 73.733 1.00 17.72
ATOM 1535 N VAL 207 37.530 25.990 82.517 1.00 22.28     ATOM 1607 CD1 ILE 214 42.710 20.977 72.639 1.00 16.15
ATOM 1536 H VAL 207 37.142 26.781 82.937 1.00 0.00      ATOM 1608 C ILE 214 46.175 19.162 74.448 1.00 23.04
ATOM 1537 CA VAL 207 37.637 25.953 81.068 1.00 17.29    ATOM 1609 O ILE 214 46.624 18.639 73.427 1.00 27.72
ATOM 1538 CB VAL 207 37.037 27.236 80.453 10.00 19.23   ATOM 1610 N ILE 215 46.810 20.139 75.083 1.00 23.66
ATOM 1539 CG1 VAL 207 37.363 27.324 78.956 1.00 18.06   ATOM 1611 H ILE 215 46.413 20.518 75.891 1.00 0.00
ATOM 1540 CG2 VAL 207 35.528 27.266 80.681 1.00 20.90   ATOM 1612 CA ILE 215 48.099 20.662 74.628 1.00 25.79
ATOM 1541 C VAL 207 39.110 25.868 80.706 1.00 17.78     ATOM 1613 CB ILE 215 48.234 22.168 74.995 1.00 25.29
ATOM 1542 O VAL 207 39.523 25.052 79.887 1.00 21.08     ATOM 1614 CG2 ILE 215 49.524 22.736 74.453 1.00 27.20
ATOM 1543 N GLU 208 39.919 26.681 81.366 1.00 18.92     ATOM 1615 CG1 ILE 215 47.052 22.950 74.429 1.00 23.49
ATOM 1544 H GLU 208 39.557 27.293 82.038 1.00 0.00      ATOM 1616 CD1 ILE 215 46.882 24.287 75.039 1.00 23.80
ATOM 1545 CA GLU 208 41.340 26.686 81.086 1.00 17.84    ATOM 1617 C ILE 215 49.264 19.872 75.248 1.00 29.29
ATOM 1546 CB GLU 208 42.036 27.785 81.880 1.00 17.11    ATOM 1618 O ILE 215 49.320 19.665 76.472 1.00 26.95
ATOM 1547 CG GLU 208 43.503 27.882 81.589 1.00 18.26    ATOM 1619 N PRO 216 50.188 19.377 74.405 1.00 32.63
ATOM 1548 CD GLU 208 44.211 28.873 82.481 1.00 22.55    ATOM 1620 CD PRO 216 50.265 19.472 72.935 1.00 36.17
ATOM 1549 OE1 GLU 208 43.533 29.622 83.224 1.00 26.35   ATOM 1621 CA PRO 216 51.321 18.621 74.943 1.00 32.44
ATOM 1550 OE2 GLU 208 45.460 28.899 82.434 1.00 25.84   ATOM 1622 CB PRO 216 52.023 18.113 73.683 1.00 33.48
ATOM 1551 C GLU 208 41.987 25.332 81.348 10.00 17.60    ATOM 1623 CG PRO 216 51.726 19.190 72.673 1.00 35.65
ATOM 1552 O GLU 208 42.847 24.906 80.570 1.00 21.38     ATOM 1624 C PRO 216 52.202 19.545 75.777 1.00 29.89
ATOM 1553 N THR 209 41.588 24.645 82.423 1.00 18.97     ATOM 1625 O PRO 216 52.264 20.762 75.544 1.00 26.07
ATOM 1554 H THR 209 40.914 25.022 83.023 1.00 0.00      ATOM 1626 N SER 217 52.848 18.965 76.775 1.00 28.39
ATOM 1555 CA THR 209 42.173 23.327 82.716 1.00 19.28    ATOM 1627 H SER 217 52.747 18.009 76.917 1.00 0.00
ATOM 1556 CB THR 209 41.799 22.770 84.123 1.00 22.75    ATOM 1628 CA SER 217 53.694 19.728 77.670 1.00 31.83
```

-continued

```
ATOM 1557 OG1 THR 209 40.389 22.550 84.200 1.00 33.54    ATOM 1629 CB SER 217 54.173 18.811 78.787 1.00 36.74
ATOM 1558 HG1 THR 209 39.924 23.378 84.048 1.00 0.00     ATOM 1630 OG SER 217 53.051 18.155 79.361 1.00 43.62
ATOM 1631 HG SER 217 52.588 17.645 78.708 1.00 0.00      ATOM 1703 CG GLN 226 50.933 34.857 80.100 1.00 56.06
ATOM 1632 C SER 217 54.858 20.434 76.973 1.00 31.11      ATOM 1704 CD GLN 226 50.740 35.034 81.608 1.00 65.41
ATOM 1633 O SER 217 55.455 19.895 76.042 1.00 29.48      ATOM 1705 OE1 GLN 226 51.682 34.873 82.389 1.00 71.36
ATOM 1634 N GLY 218 55.162 21.653 77.413 1.00 31.19      ATOM 1706 NE2 GLN 226 49.521 35.380 82.019 1.00 69.24
ATOM 1635 H GLY 218 54.650 22.057 78.150 1.00 0.00       ATOM 1707 HE21 GLN 226 48.811 35.506 81.360 1.00 0.00
ATOM 1636 CA GLY 218 56.242 22.399 76.798 1.00 31.10     ATOM 1708 HE22 GLN 226 49.396 35.496 82.982 1.00 0.00
ATOM 1637 C GLY 218 56.119 23.905 76.949 1.00 33.16      ATOM 1709 C GLN 226 48.358 33.721 79.040 1.00 26.90
ATOM 1638 O GLY 218 55.185 24.185 77.598 1.00 32.64      ATOM 1710 O GLN 226 47.762 34.651 79.586 1.00 26.58
ATOM 1639 N PRO 219 57.047 24.672 76.344 1.00 33.29      ATOM 1711 N ARG 227 48.230 33.430 77.746 1.00 28.46
ATOM 1640 CD PRO 219 58.239 24.177 75.628 1.00 30.91     ATOM 1712 H ARG 227 48.774 32.706 77.369 1.00 0.00
ATOM 1641 CA PRO 219 57.055 26.135 76.413 1.00 33.69     ATOM 1713 CA ARG 227 47.301 34.156 76.868 1.00 28.40
ATOM 1642 CB PRO 219 58.365 26.502 75.716 1.00 33.20     ATOM 1714 CB ARG 227 47.482 33.742 75.419 1.00 29.43
ATOM 1643 CG PRO 219 58.620 25.357 74.807 1.00 32.73     ATOM 1715 CG ARG 227 48.691 34.349 74.796 1.00 28.83
ATOM 1644 C PRO 219 55.855 26.808 75.772 1.00 36.42      ATOM 1716 CD ARG 227 49.207 33.479 73.692 1.00 35.73
ATOM 1645 O PRO 219 55.382 27.835 76.264 1.00 38.04      ATOM 1717 NE ARG 227 50.642 33.666 73.540 1.00 41.05
ATOM 1646 N LEU 220 53.355 26.221 74.688 1.00 37.44      ATOM 1718 HE ARG 227 51.220 32.889 73.649 1.00 0.00
ATOM 1647 H LEU 220 55.767 25.403 74.349 1.00 0.00       ATOM 1719 CZ ARG 227 51.211 34.829 73.252 1.00 42.98
ATOM 1648 CA LEU 220 54.202 26.775 73.984 1.00 36.21     ATOM 1720 NH1 ARG 227 50.460 35.910 73.072 1.00 47.92
ATOM 1649 CB LEU 220 54.025 26.095 72.623 1.00 41.05     ATOM 1721 HH11 ARG 227 49.463 35.860 73.153 1.00 0.00
ATOM 1650 CG LEU 220 53.027 26.676 71.610 1.00 43.93     ATOM 1722 HH12 ARG 227 50.888 36.792 72.859 1.00 0.00
ATOM 1651 CD1 LEU 220 53.099 28.216 72.577 1.00 42.74    ATOM 1723 NH2 ARG 227 52.532 34.924 73.195 1.00 44.69
ATOM 1652 CD2 LEU 220 53.308 26.064 70.228 1.00 43.21    ATOM 1724 HH21 ARG 227 53.090 34.116 73.359 1.00 0.00
ATOM 1653 C LEU 220 52.955 26.627 74.836 1.00 33.18      ATOM 1725 HH22 ARG 227 52.957 35.802 72.974 1.00 0.00
ATOM 1654 O LEU 220 52.096 27.505 74.844 1.00 31.72      ATOM 1726 C ARG 227 45.867 33.905 77.289 1.00 28.89
ATOM 1655 N LYS 221 52.895 25.540 75.599 1.00 32.75      ATOM 1727 O ARG 227 45.042 34.827 77.269 1.00 30.98
ATOM 1656 H LYS 221 53.622 24.890 75.550 1.00 0.00       ATOM 1728 N LEU 228 45.572 32.658 77.652 1.00 27.57
ATOM 1657 CA LYS 221 51.764 25.288 76.487 1.00 32.53     ATOM 1729 H LEU 228 46.254 31.979 77.605 1.00 0.00
ATOM 1658 CB LYS 221 51.914 23.923 77.173 1.00 31.53     ATOM 1730 CA LEU 228 44.244 32.302 78.131 1.00 27.07
ATOM 1659 CG LYS 221 50.728 23.519 78.040 1.00 29.82     ATOM 1731 CB LEU 228 44.144 30.806 78.458 1.00 26.14
ATOM 1660 CD LYS 221 50.778 22.048 78.391 1.00 28.10     ATOM 1732 CG LEU 228 43.930 29.847 77.287 1.00 26.19
ATOM 1661 CE LYS 221 49.564 21.636 79.198 1.00 21.91     ATOM 1733 CD1 LEU 228 43.862 28.428 77.813 1.00 22.88
ATOM 1662 NZ LYS 221 49.367 20.165 79.180 1.00 18.88     ATOM 1734 CD2 LEU 228 42.657 30.211 76.513 1.00 23.61
ATOM 1663 HZ1 LYS 221 50.205 19.703 79.595 1.00 0.00     ATOM 1735 C LEU 228 43.958 33.127 79.380 1.00 23.46
ATOM 1664 HZ2 LYS 221 49.241 19.843 78.212 1.00 0.00     ATOM 1736 O LEU 228 42.938 33.793 79.461 1.00 23.05
ATOM 1665 HZ3 LYS 221 48.529 19.921 79.742 1.00 0.00     ATOM 1737 N GLU 229 44.886 33.122 80.329 1.00 25.86
ATOM 1666 C LYS 221 51.717 26.403 77.527 1.00 33.59      ATOM 1738 H GLU 229 45.702 32.595 80.200 1.00 0.00
ATOM 1667 O LYS 221 50.643 26.869 77.928 1.00 31.97      ATOM 1739 CA GLU 229 44.712 33.881 81.556 1.00 26.46
ATOM 1668 N ALA 222 52.902 26.850 77.930 1.00 35.55      ATOM 1740 CB GLU 229 45.858 33.592 52.506 1.00 29.02
ATOM 1669 H ALA 222 53.711 26.447 77.562 1.00 0.00       ATOM 1741 CG GLU 229 45.736 32.220 83.117 1.00 35.68
ATOM 1670 CA ALA 222 53.035 27.918 78.915 1.00 36.45     ATOM 1742 CD GLU 229 47.055 31.639 83.590 1.00 42.02
ATOM 1671 CB ALA 222 54.493 28.048 79.348 1.00 38.57     ATOM 1743 OE1 GLU 229 47.020 30.587 84.257 1.00 47.25
ATOM 1672 C ALA 222 52.541 29.235 78.329 1.00 34.13      ATOM 1744 OE2 GLU 229 48.128 32.208 83.290 1.00 48.22
ATOM 1673 A ALA 222 51.845 30.012 78.996 1.00 32.40      ATOM 1745 C GLU 229 44.567 35.380 81.295 1.00 28.97
ATOM 1674 N GLU 223 52.902 29.470 77.072 1.00 31.05      ATOM 1746 O GLU 229 43.705 36.036 81.889 1.00 28.12
ATOM 1675 H GLU 223 53.452 28.804 76.611 1.00 0.00       ATOM 1747 N ASP 230 45.367 35.907 80.371 1.00 30.33
ATOM 1676 CA GLU 223 52.517 30.681 76.374 1.00 31.88     ATOM 1748 H ASP 230 46.005 35.330 79.913 1.00 0.00
ATOM 1677 CB GLU 223 53.179 30.713 75.010 1.00 33.98     ATOM 1749 CA ASP 230 45.309 37.322 80.020 1.00 31.37
ATOM 1678 CG GLU 223 54.682 30.818 75.116 1.00 40.16     ATOM 1750 CB ASP 230 46.459 37.705 79.096 1.00 34.93
ATOM 1679 CD GLU 223 55.380 30.540 73.804 1.00 46.19     ATOM 1751 CG ASP 230 47.790 37.849 79.830 1.00 43.53
ATOM 1680 OE1 GLU 223 54.721 30.653 72.749 1.00 46.69    ATOM 1752 OD1 ASP 230 47.814 37.851 81.088 1.00 42.08
ATOM 1681 OE2 GLU 223 56.584 30.191 73.830 1.00 49.10    ATOM 1753 OD2 ASP 230 48.826 37.965 79.131 1.00 47.31
ATOM 1682 C GLU 223 51.010 30.774 76.253 1.00 29.27      ATOM 1754 C ASP 230 43.998 37.697 79.352 1.00 33.84
ATOM 1683 O GLU 223 50.418 31.770 76.657 1.00 27.55      ATOM 1755 O ASP 230 43.461 38.778 79.608 1.00 35.17
ATOM 1684 N ILE 224 50.387 29.700 75.775 1.00 28.64      ATOM 1756 N VAL 231 43.518 36.847 78.446 1.00 31.08
ATOM 1685 H ILE 224 50.919 28.919 75.518 1.00 0.00       ATOM 1757 H VAL 231 44.005 36.027 78.242 1.00 0.00
ATOM 1686 CA ILE 224 48.932 29.653 75.627 1.00 24.57     ATOM 1758 CA VAL 231 42.256 37.117 77.761 1.00 32.04
ATOM 1687 CB ILE 224 48.475 28.322 75.026 1.00 22.57     ATOM 1759 CB VAL 231 42.030 36.166 76.550 1.00 29.32
ATOM 1688 CG2 ILE 224 46.965 28.283 74.940 1.00 20.95    ATOM 1760 CG1 VAL 231 40.688 36.435 75.898 1.00 27.10
ATOM 1689 CG1 ILE 224 49.095 28.140 73.642 1.00 21.34    ATOM 1761 CG2 VAL 231 43.133 36.337 75.535 1.00 25.64
ATOM 1690 CD1 ILE 224 49.068 26.710 73.156 1.00 30.02    ATOM 1762 C VAL 231 41.093 36.990 78.754 1.00 36.60
ATOM 1691 C ILE 224 48.265 29.851 76.980 1.00 23.70      ATOM 1763 O VAL 231 40.191 37.832 78.764 1.00 40.64
ATOM 1692 O ILE 224 47.323 30.640 77.105 1.00 24.41      ATOM 1764 N PHE 232 41.157 35.984 79.632 1.00 34.95
ATOM 1693 N ALA 225 48.765 29.150 77.996 1.00 22.80      ATOM 1765 H PHE 232 41.928 35.385 79.603 1.00 0.00
ATOM 1694 H ALA 225 49.508 28.532 77.830 1.00 0.00       ATOM 1766 CA PHE 232 40.106 35.745 80.632 1.00 38.18
ATOM 1695 CA ALA 225 48.230 29.273 79.348 1.00 21.66     ATOM 1767 CB PHE 232 40.330 34.414 81.378 1.00 33.30
ATOM 1696 CB ALA 225 49.125 28.538 80.327 1.00 26.49     ATOM 1768 CG PHE 232 40.068 33.181 80.538 1.00 28.81
ATOM 1697 C ALA 225 48.153 30.739 79.729 1.00 21.34      ATOM 1769 CD1 PHE 232 40.559 31.945 80.939 1.00 25.79
ATOM 1698 O ALA 225 47.103 31.228 80.144 1.00 21.30      ATOM 1770 CD2 PHE 232 39.329 33.254 79.356 1.00 25.06
ATOM 1699 N GLN 226 49.254 31.453 79.508 1.00 25.01      ATOM 1771 CE1 PHE 232 40.319 30.794 80.178 1.00 27.90
ATOM 1700 H GLN 226 50.037 31.011 79.110 1.00 0.00       ATOM 1772 CE2 PHE 232 39.084 32.112 78.588 1.00 25.66
ATOM 1701 CA GLN 226 49.333 32.875 79.837 1.00 30.14     ATOM 1773 CZ PHE 232 39.575 30.882 78.994 1.00 26.36
ATOM 1702 CB GLN 226 50.751 33.411 79.639 1.00 40.36     ATOM 1774 C PHE 232 40.023 36.896 81.625 1.00 39.58
ATOM 1775 O PHE 232 38.942 37.221 82.120 1.00 41.97      ATOM 1847 O GLU 240 45.378 38.202 64.693 1.00 25.96
ATOM 1776 N ALA 233 41.170 37.514 81.899 1.00 42.06      ATOM 1848 N VAL 241 45.514 39.825 66.246 1.00 24.78
ATOM 1777 H ALA 233 41.993 37.182 81.492 1.00 0.00       ATOM 1849 H VAL 241 45.050 40.549 66.715 1.00 0.00
ATOM 1778 CA ALA 233 41.251 38.651 82.813 1.00 41.28     ATOM 1850 CA VAL 241 46.898 39.456 66.603 1.00 25.87
ATOM 1779 CB ALA 233 42.658 38.793 83.349 1.00 36.00     ATOM 1851 CB VAL 241 47.459 40.657 67.517 1.00 28.94
```

-continued

```
ATOM 1780 C   ALA 233 40.834 39.932 82.108 1.00 43.84     ATOM 1852 CG1 VAL 241 48.651 40.155 68.319 1.00 31.40
ATOM 1781 O   ALA 233 40.844 41.002 82.706 1.00 45.83     ATOM 1853 CG2 VAL 241 47.869 41.846 66.670 1.00 29.28
ATOM 1782 N   GLY 234 40.498 39.822 80.827 1.00 48.25     ATOM 1854 C   VAL 241 46.991 38.185 67.291 1.00 25.79
ATOM 1783 H   GLY 234 40.497 38.951 80.388 1.00 0.00      ATOM 1855 O   VAL 241 47.911 37.402 67.023 1.00 28.70
ATOM 1784 CA  GLY 234 40.091 40.984 80.061 1.00 53.20     ATOM 1856 N   LEU 242 46.008 37.899 68.141 1.00 25.00
ATOM 1785 C   GLY 234 41.249 41.931 79.800 1.00 57.49     ATOM 1857 H   LEU 242 45.319 38.580 68.298 1.00 0.00
ATOM 1786 O   GLY 234 41.044 43.082 79.406 1.00 58.25     ATOM 1858 CA  LEU 242 45.916 36.633 68.868 1.00 22.95
ATOM 1787 N   LYS 235 42.468 41.466 80.053 1.00 60.31     ATOM 1859 CB  LEU 242 44.715 36.682 69.810 1.00 25.74
ATOM 1788 H   LYS 235 42.573 40.558 80.384 1.00 0.00      ATOM 1860 CG  LEU 242 44.994 36.696 71.303 1.00 25.17
ATOM 1789 CA  LYS 235 43.648 42.289 79.825 1.00 63.78     ATOM 1861 CD1 LEU 242 43.666 36.756 72.033 1.00 21.02
ATOM 1790 CB  LYS 235 44.803 41.862 80.741 1.00 71.11     ATOM 1862 CD2 LEU 242 45.802 35.448 71.674 1.00 28.21
ATOM 1791 CG  LYS 235 46.143 42.567 80.460 1.00 82.93     ATOM 1863 C   LEU 242 45.737 35.443 67.920 1.00 19.00
ATOM 1792 CD  LYS 235 46.041 44.109 80.405 1.00 89.87     ATOM 1864 O   LEU 242 46.388 34.411 68.067 1.00 16.60
ATOM 1793 CE  LYS 235 45.721 44.735 81.759 1.00 93.76     ATOM 1865 N   MET 243 44.830 35.600 66.961 1.00 17.56
ATOM 1794 NZ  LYS 235 45.539 46.209 81.649 1.00 94.59     ATOM 1866 H   MET 243 44.357 36.445 66.905 1.00 0.00
ATOM 1795 HZ1 LYS 235 44.758 46.419 81.005 1.00 0.00      ATOM 1867 CA  MET 243 44.524 34.568 65.983 1.00 17.74
ATOM 1796 HZ2 LYS 235 46.418 46.640 81.293 1.00 0.00      ATOM 1868 CB  MET 243 43.225 34.917 65.255 1.00 15.78
ATOM 1797 HZ3 LYS 235 45.331 46.600 82.594 1.00 0.00      ATOM 1869 CG  MET 243 42.001 34.952 66.157 1.00 13.77
ATOM 1798 C   LYS 235 44.053 42.184 78.363 1.00 61.62     ATOM 1870 SD  MET 243 41.528 33.366 66.919 1.00 15.74
ATOM 1799 O   LYS 235 44.314 43.194 77.705 1.00 63.55     ATOM 1871 CE  MET 243 40.733 32.532 65.613 1.00 10.67
ATOM 1800 N   ASN 236 44.129 40.957 77.865 1.00 58.43     ATOM 1872 C   MET 243 45.672 34.286 65.000 1.00 16.07
ATOM 1801 H   ASN 236 43.918 40.198 78.433 1.00 0.00      ATOM 1873 O   MET 243 45.918 33.139 64.630 1.00 17.62
ATOM 1802 CA  ASN 236 44.486 40.736 76.472 1.00 55.59     ATOM 1874 N   GLU 244 46.395 35.322 64.600 1.00 21.04
ATOM 1803 CB  ASN 236 45.045 39.320 76.270 1.00 52.40     ATOM 1875 H   GLU 244 46.156 36.224 64.896 1.00 0.00
ATOM 1804 CG  ASN 236 45.805 39.163 74.954 1.00 50.33     ATOM 1876 CA  GLU 244 47.534 35.139 63.700 1.00 22.88
ATOM 1805 OD1 ASN 236 45.523 39.848 73.972 1.00 48.03     ATOM 1877 CB  GLU 244 48.030 36.496 63.172 1.00 26.39
ATOM 1806 ND2 ASN 236 46.775 38.249 74.934 1.00 45.67     ATOM 1878 CG  GLU 244 49.197 36.408 62.174 1.00 31.05
ATOM 1807 HD21 ASN 236 46.951 37.720 75.736 1.00 0.00     ATOM 1879 CD  GLU 244 48.894 35.527 60.955 1.00 33.63
ATOM 1808 HD22 ASN 236 47.261 38.136 74.093 1.00 0.00     ATOM 1880 OE1 GLU 244 49.749 34.680 60.623 1.00 33.84
ATOM 1809 C   ASN 236 43.251 40.958 75.593 1.00 55.63     ATOM 1881 OE2 GLU 244 47.812 35.679 60.334 1.00 35.83
ATOM 1810 O   ASN 236 42.097 40.813 76.032 1.00 55.31     ATOM 1882 C   GLU 244 48.655 34.393 64.430 1.00 21.16
ATOM 1811 N   THR 237 43.511 41.376 74.366 1.00 53.25     ATOM 1883 O   GLU 244 49.289 33.514 63.854 1.00 21.96
ATOM 1812 H   THR 237 44.441 41.499 74.082 1.00 0.00      ATOM 1884 N   TRP 245 48.875 34.733 65.701 1.00 21.45
ATOM 1813 CA  THR 237 42.468 41.620 73.403 1.00 51.23     ATOM 1885 H   TRP 245 48.340 35.455 66.101 1.00 0.00
ATOM 1814 CB  THR 237 41.707 42.919 73.725 1.00 51.31     ATOM 1886 CA  TRP 245 49.901 34.076 66.514 1.00 24.48
ATOM 1815 OG1 THR 237 40.687 43.138 72.741 1.00 57.93     ATOM 1887 CB  TRP 245 49.914 34.661 67.941 1.00 27.17
ATOM 1816 HG1 THR 237 40.072 42.398 72.749 1.00 0.00      ATOM 1888 CG  TRP 245 50.932 34.013 68.893 1.00 30.61
ATOM 1817 CG2 THR 237 42.652 44.102 73.786 1.00 51.40     ATOM 1889 CD2 TRP 245 50.681 32.971 69.853 1.00 32.76
ATOM 1818 C   THR 237 43.129 41.633 72.028 1.00 49.50     ATOM 1890 CE2 TRP 245 51.919 32.674 70.480 1.00 33.63
ATOM 1819 O   THR 237 44.216 41.078 71.868 1.00 51.84     ATOM 1891 CE3 TRP 245 49.545 32.254 70.246 1.00 34.69
ATOM 1820 N   ASP 238 42.509 42.293 71.057 1.00 46.73     ATOM 1892 CD1 TRP 245 52.267 34.298 68.892 1.00 32.07
ATOM 1821 H   ASP 238 41.689 42.772 71.255 1.00 0.00      ATOM 1893 NE1 TRP 245 52.864 33.497 69.928 1.00 31.38
ATOM 1822 CA  ASP 238 43.005 42.337 69.674 1.00 44.41     ATOM 1894 HE1 TRP 245 53.819 33.516 70.159 1.00 0.00
ATOM 1823 CB  ASP 238 43.032 43.819 69.519 1.00 46.32     ATOM 1895 CZ2 TRP 245 52.043 31.689 71.477 1.00 36.30
ATOM 1824 CG  ASP 238 44.526 43.648 68.139 1.00 50.54     ATOM 1896 CZ3 TRP 245 49.675 31.265 71.247 1.00 38.55
ATOM 1825 OD1 ASP 238 45.580 43.438 67.522 1.00 53.28     ATOM 1897 CH2 TRP 245 50.916 30.999 71.844 1.00 33.06
ATOM 1826 OD2 ASP 238 43.601 44.348 67.667 1.00 53.75     ATOM 1898 C   TRP 245 49.583 32.588 66.576 1.00 24.04
ATOM 1827 C   ASP 238 43.071 40.913 69.154 1.00 39.10     ATOM 1899 O   TRP 245 50.438 31.731 66.337 1.00 20.97
ATOM 1828 O   ASP 238 44.140 40.306 69.006 1.00 35.55     ATOM 1900 N   LEU 246 48.325 32.296 66.879 1.00 24.79
ATOM 1829 N   LEU 239 41.874 40.404 68.898 1.00 32.36     ATOM 1901 H   LEU 246 47.699 33.031 67.048 1.00 0.00
ATOM 1830 H   LEU 239 41.096 40.974 69.054 1.00 0.00      ATOM 1902 CA  LEU 246 47.848 30.924 66.985 1.00 25.07
ATOM 1831 CA  LEU 239 41.648 39.073 68.413 1.00 28.63     ATOM 1903 CB  LEU 246 46.351 30.912 67.291 1.00 24.89
ATOM 1832 CB  LEU 239 40.165 38.916 68.102 1.00 23.74     ATOM 1904 CG  LEU 246 45.853 30.275 68.585 1.00 26.05
ATOM 1833 CG  LEU 239 39.718 37.501 67.798 1.00 20.81     ATOM 1905 CD1 LEU 246 44.356 30.340 68.547 1.00 18.05
ATOM 1834 CD1 LEU 239 40.158 36.576 68.937 1.00 18.50     ATOM 1906 CD2 LEU 246 46.330 28.829 68.700 1.00 23.56
ATOM 1835 CD2 LEU 239 38.218 37.515 67.603 1.00 14.34     ATOM 1907 C   LEU 246 48.089 30.174 65.688 1.00 24.91
ATOM 1836 C   LEU 239 42.480 38.753 67.184 1.00 31.22     ATOM 1908 O   LEU 246 48.650 29.084 65.690 1.00 26.81
ATOM 1837 O   LEU 239 42.986 37.639 67.063 1.00 32.51     ATOM 1909 N   LYS 247 47.651 30.777 64.588 1.00 24.06
ATOM 1838 N   GLU 240 42.661 39.734 66.301 1.00 32.13     ATOM 1910 H   LYS 247 47.209 31.648 64.678 1.00 0.00
ATOM 1839 H   GLU 240 42.293 40.611 66.483 1.00 0.00      ATOM 1911 CA  LYS 247 47.783 30.202 63.250 1.00 24.97
ATOM 1840 CA  GLU 240 43.423 39.516 65.070 1.00 33.79     ATOM 1912 CB  LYS 247 47.290 31.214 62.214 1.00 21.42
ATOM 1841 CB  GLU 240 43.322 40.728 64.129 1.00 41.79     ATOM 1913 CG  LYS 247 47.163 30.688 60.806 1.00 24.96
ATOM 1842 CG  GLU 240 43.896 42.032 64.658 1.00 58.76     ATOM 1914 CD  LYS 247 46.689 31.805 59.889 1.00 26.54
ATOM 1843 CD  GLU 240 45.250 42.392 64.046 1.00 68.00     ATOM 1915 CE  LYS 247 46.554 31.341 58.446 1.00 33.16
ATOM 1844 OE1 GLU 240 45.852 43.403 64.488 1.00 72.93     ATOM 1916 NZ  LYS 247 46.058 32.427 57.534 1.00 33.41
ATOM 1845 OE2 GLU 240 45.710 41.676 63.124 1.00 71.76     ATOM 1917 HZ1 LYS 247 46.728 33.223 57.547 1.00 0.00
ATOM 1846 C   GLU 240 44.867 39.126 65.321 1.00 26.92     ATOM 1918 HZ2 LYS 247 45.123 32.759 57.854 1.00 0.00
ATOM 1919 HZ3 LYS 247 45.978 32.058 56.566 1.00 0.00      ATOM 1991 CB  LEU 255 42.116 19.306 65.998 1.00 17.29
ATOM 1920 C   LYS 247 49.219 29.822 62.932 1.00 27.05     ATOM 1992 CG  LEU 255 40.734 18.824 66.457 1.00 22.10
ATOM 1921 O   LYS 247 49.473 28.786 62.314 1.00 26.64     ATOM 1993 CD1 LEU 255 40.913 18.124 67.786 1.00 21.22
ATOM 1922 N   THR 248 50.154 30.645 63.392 1.00 28.34     ATOM 1994 CD2 LEU 255 39.689 19.923 66.533 1.00 10.32
ATOM 1923 H   THR 248 49.890 31.428 63.933 1.00 0.00      ATOM 1995 C   LEU 255 42.551 21.554 67.079 1.00 16.96
ATOM 1924 CA  THR 248 51.570 30.423 63.124 1.00 31.20     ATOM 1996 O   LEU 255 41.593 22.187 67.517 1.00 14.88
ATOM 1925 CB  THR 248 52.294 31.768 62.899 1.00 27.11     ATOM 1997 N   THR 256 43.726 21.532 67.698 1.00 15.29
ATOM 1926 OG1 THR 248 52.022 32.657 63.988 1.00 30.01     ATOM 1998 H   THR 256 44.484 21.039 67.324 1.00 0.00
ATOM 1927 HG1 THR 248 52.313 32.269 64.817 1.00 0.00      ATOM 1999 CA  THR 256 43.881 22.259 68.947 1.00 16.68
ATOM 1928 CG2 THR 248 51.806 32.410 61.631 1.00 25.94     ATOM 2000 CB  THR 256 45.150 21.812 69.788 1.00 17.18
ATOM 1929 C   THR 248 52.405 29.541 64.070 1.00 33.96     ATOM 2001 OG1 THR 256 46.343 22.261 69.261 1.00 26.67
ATOM 1930 O   THR 248 53.598 29.343 63.808 1.00 37.57     ATOM 2002 HG1 THR 256 47.108 21.963 69.681 1.00 0.00
```

-continued

```
ATOM 1931 N ARG 249 51.801 29.007 65.139 1.00 33.40     ATOM 2003 CG2 THR 256 45.230 20.292 69.895 1.00 12.01
ATOM 1932 H ARG 249 50.843 29.187 65.282 1.00 0.00      ATOM 2004 C THR 256 43.899 23.738 68.578 1.00 20.08
ATOM 1933 CA ARG 249 52.513 28.152 66.107 1.00 31.70    ATOM 2005 O THR 256 43.388 24.576 69.328 1.00 22.98
ATOM 1934 CB ARG 249 51.264 27.826 67.313 1.00 27.94    ATOM 2006 N LYS 257 44.414 24.055 67.386 1.00 19.49
ATOM 1935 CG ARG 249 51.202 29.005 68.146 1.00 28.39    ATOM 2007 H LYS 257 44.782 23.352 66.815 1.00 0.00
ATOM 1936 CD ARG 249 52.394 29.831 68.538 1.00 29.29    ATOM 2008 CA LYS 257 44.440 25.443 66.916 1.00 16.20
ATOM 1937 NE ARG 249 52.783 30.729 67.461 1.00 33.71    ATOM 2009 CB LYS 257 45.227 25.580 65.608 1.00 18.79
ATOM 1938 HE ARG 249 52.182 30.821 66.692 1.00 0.00     ATOM 2010 CG LYS 257 46.730 25.614 65.807 1.00 19.72
ATOM 1939 CZ ARG 249 53.907 31.436 67.449 1.00 38.58    ATOM 2011 CD LYS 257 47.458 25.681 64.480 1.00 21.43
ATOM 1940 NH1 ARG 249 54.763 31.340 68.458 1.00 41.62   ATOM 2012 CE LYS 257 48.960 25.713 64.707 1.00 23.03
ATOM 1941 HH11 ARG 249 54.557 30.736 69.227 1.00 0.00   ATOM 2013 NZ LYS 257 49.754 26.153 63.517 1.00 20.57
ATOM 1942 HH12 ARG 249 55.605 31.876 68.452 1.00 0.00   ATOM 2014 HZ1 LYS 257 49.457 27.108 63.239 1.00 0.00
ATOM 1943 NH2 ARG 249 54.144 32.287 66.459 1.00 39.18   ATOM 2015 HZ2 LYS 257 49.572 25.492 62.733 1.00 0.00
ATOM 1944 HH21 ARG 249 53.475 32.406 65.725 1.00 0.00   ATOM 2016 HZ3 LYS 257 50.760 26.149 63.750 1.00 0.00
ATOM 1945 HH22 ARG 249 54.988 32.827 66.456 1.00 0.00   ATOM 2017 C LYS 257 43.012 25.932 66.726 1.00 12.86
ATOM 1946 C ARG 249 52.966 26.826 65.523 1.00 34.57     ATOM 2018 O LYS 257 42.669 27.034 67.141 1.00 14.09
ATOM 1947 O ARG 249 52.158 26.069 64.993 1.00 38.65     ATOM 2019 N GLY 258 42.170 25.084 66.154 1.00 12.55
ATOM 1948 N PRO 250 54.262 26.508 65.619 1.00 37.16     ATOM 2020 H GLY 258 42.490 24.214 65.855 1.00 0.00
ATOM 1949 CD PRO 250 55.426 27.207 66.175 1.00 38.70    ATOM 2021 CA GLY 258 40.778 25.446 65.956 1.00 15.35
ATOM 1950 CA PRO 250 54.647 25.214 65.051 1.00 38.55    ATOM 2022 C GLY 258 40.050 25.691 67.273 1.00 15.50
ATOM 1951 CB PRO 250 56.181 25.283 65.033 1.00 39.31    ATOM 2023 O GLY 258 39.320 26.682 67.431 1.00 13.67
ATOM 1952 CG PRO 250 56.502 26.765 65.223 1.00 40.46    ATOM 2024 N ILE 259 40.259 24.784 68.224 1.00 16.64
ATOM 1953 C PRO 250 54.161 24.175 66.058 1.00 41.32     ATOM 2025 H ILE 259 40.852 24.025 68.031 1.00 0.00
ATOM 1954 O PRO 250 53.760 24.533 67.174 1.00 39.81     ATOM 2026 CA ILE 259 39.636 27.878 69.542 1.00 14.17
ATOM 1955 N ILE 251 54.221 22.903 65.676 1.00 43.38     ATOM 2027 CB ILE 259 39.859 23.571 70.356 1.00 15.52
ATOM 1956 H ILE 251 54.559 22.703 64.787 1.00 0.00      ATOM 2028 CG2 ILE 259 39.512 23.757 71.850 1.00 11.02
ATOM 1957 CA ILE 251 53.805 21.769 66.523 1.00 46.51    ATOM 2029 CG1 ILE 259 39.014 22.464 69.731 1.00 6.64
ATOM 1958 CB ILE 251 54.707 21.566 67.821 1.00 49.95    ATOM 2030 CD1 ILE 259 39.381 21.073 70.183 1.00 10.73
ATOM 1959 CG2 ILE 251 56.187 21.729 67.472 1.00 49.50   ATOM 2031 C ILE 259 40.084 26.130 70.292 1.00 10.91
ATOM 1960 CG1 ILE 251 54.277 22.493 68.972 1.00 53.08   ATOM 2032 O ILE 259 39.255 26.836 70.838 1.00 13.73
ATOM 1961 CD1 ILE 251 54.997 22.250 70.291 1.00 56.61   ATOM 2033 N LEU 260 41.373 26.443 70.281 1.00 12.18
ATOM 1962 C ILE 251 52.316 21.655 66.898 1.00 41.74     ATOM 2034 H LEU 260 42.014 25.865 69.823 1.00 0.00
ATOM 1963 O ILE 251 51.756 20.555 66.831 1.00 42.72     ATOM 2035 CA LEU 260 41.847 27.650 70.960 1.00 11.32
ATOM 1964 N LEU 252 51.684 22.754 67.309 1.00 37.22     ATOM 2036 CB LEU 260 43.369 27.694 71.023 1.00 13.90
ATOM 1965 H LEU 252 52.163 23.600 67.371 1.00 0.00      ATOM 2037 CG LEU 260 44.033 26.747 72.013 1.00 18.17
ATOM 1966 CA LEU 252 50.265 22.718 67.671 1.00 32.33    ATOM 2038 CD1 LEU 260 45.426 26.426 71.518 1.00 16.80
ATOM 1967 CB LEU 252 49.724 24.125 67.908 1.00 28.03    ATOM 2039 CD2 LEU 260 44.034 27.359 73.421 1.00 13.15
ATOM 1968 CG LEU 252 50.062 24.767 69.243 1.00 27.67    ATOM 2040 C LEU 260 41.345 28.867 70.220 1.00 11.32
ATOM 1969 CD1 LEU 252 49.149 25.950 69.450 1.00 23.50   ATOM 2041 O LEU 260 41.007 29.873 70.833 1.00 13.99
ATOM 1970 CD2 LEU 252 49.888 23.745 70.370 1.00 30.62   ATOM 2042 N GLY 261 41.305 28.773 68.893 1.00 13.68
ATOM 1971 C LEU 252 49.445 22.061 66.571 1.00 29.96     ATOM 2043 H GLY 261 41.626 27.962 68.455 1.00 0.00
ATOM 1972 O LEU 252 49.461 22.511 65.426 1.00 33.29     ATOM 2044 CA GLY 261 40.806 29.878 68.088 1.00 12.10
ATOM 1973 N SER 253 48.760 20.974 66.894 1.00 28.11     ATOM 2045 C GLY 261 39.359 30.142 68.439 1.00 6.12
ATOM 1974 H SER 253 48.787 20.641 67.806 1.00 0.00      ATOM 2046 O GLY 261 38.939 31.273 68.618 1.00 8.51
ATOM 1975 CA SER 253 47.954 20.317 65.884 1.00 25.46    ATOM 2047 N PHE 262 38.589 29.073 68.540 1.00 9.67
ATOM 1976 CB SER 253 47.342 19.016 66.407 1.00 26.72    ATOM 2048 H PHE 262 38.970 28.200 68.359 1.00 0.00
ATOM 1977 OG SER 253 46.147 19.250 67.128 1.00 27.57    ATOM 2049 CA PHE 262 37.183 29.170 68.912 1.00 12.77
ATOM 1978 HG SER 253 45.795 18.417 67.447 1.00 0.00     ATOM 2050 CB PHE 262 36.538 27.782 68.856 1.00 10.75
ATOM 1979 C SER 253 46.855 21.277 65.430 1.00 23.91     ATOM 2051 CG PHE 262 35.095 27.751 69.278 1.00 10.80
ATOM 1980 O SER 253 46.395 22.137 66.194 1.00 20.03     ATOM 2052 CD1 PHE 262 34.102 27.451 68.349 1.00 8.33
ATOM 1981 N PRO 254 46.402 21.121 64.185 1.00 22.83     ATOM 2053 CD2 PHE 262 34.729 27.961 70.612 1.00 9.95
ATOM 1982 CD PRO 254 46.762 20.032 63.254 1.00 24.06    ATOM 2054 CE1 PHE 262 32.772 27.357 68.728 1.00 9.19
ATOM 1983 CA PRO 254 45.351 21.967 63.614 1.00 24.41    ATOM 2055 CE2 PHE 262 33.401 27.871 71.009 1.00 11.23
ATOM 1984 CB PRO 254 45.041 21.255 62.285 1.00 25.78    ATOM 2056 CZ PHE 262 32.413 27.566 70.060 1.00 11.72
ATOM 1985 CG PRO 254 46.354 20.601 61.934 1.00 24.32    ATOM 2057 C PHE 262 37.071 29.766 70.316 1.00 11.12
ATOM 1986 C PRO 254 44.087 22.042 64.502 1.00 23.16     ATOM 2058 O PHE 262 36.273 30.659 70.531 1.00 16.33
ATOM 1987 O PRO 254 43.546 23.121 64.754 1.00 19.45     ATOM 2059 N VAL 263 37.884 29.298 71.264 1.00 13.36
ATOM 1988 N LEU 255 43.625 20.880 64.953 1.00 20.07     ATOM 2060 H VAL 263 38.522 28.589 71.039 1.00 0.00
ATOM 1989 H LEU 255 44.105 20.062 64.726 1.00 0.00      ATOM 2061 CA VAL 263 37.835 29.823 72.639 1.00 15.47
ATOM 1990 CA LEU 255 42.427 20.780 65.765 1.00 19.36    ATOM 2062 CB VAL 263 38.723 28.976 73.600 1.00 17.93
ATOM 2063 CG1 VAL 263 38.886 29.672 74.947 1.00 17.24   ATOM 2135 OE1 GLU 271 33.591 37.125 66.168 1.00 48.54
ATOM 2064 CG2 VAL 263 38.079 27.609 73.822 1.00 15.21   ATOM 2136 OE2 GLU 271 32.192 38.148 67.537 1.00 53.65
ATOM 2065 C VAL 263 38.180 31.321 72.732 1.00 15.07     ATOM 2137 C GLU 271 36.516 47.789 66.791 1.00 56.14
ATOM 2066 O VAL 263 37.462 32.096 73.375 1.00 15.34     ATOM 2138 O GLU 271 37.376 41.683 65.921 1.00 56.73
ATOM 2067 N PHE 264 39.250 31.731 82.055 1.00 18.90     ATOM 2139 N ARG 272 35.817 42.907 67.005 1.00 58.86
ATOM 2068 H PHE 264 39.774 31.076 75.557 1.00 0.00      ATOM 2140 H ARG 272 35.131 42.903 67.700 1.00 0.00
ATOM 2069 CA PHE 264 39.669 33.133 72.031 1.00 21.09    ATOM 2141 CA ARG 272 36.035 44.158 66.273 1.00 61.83
ATOM 2070 CB PHE 264 40.975 33.309 71.245 1.00 21.53    ATOM 2142 CB ARG 272 37.466 44.684 66.496 1.00 66.96
ATOM 2071 CG PHE 264 42.197 32.825 71.974 1.00 24.83    ATOM 2143 CG ARG 272 37.927 44.727 67.953 1.00 78.06
ATOM 2072 CD1 PHE 264 43.274 32.288 71.266 1.00 24.52   ATOM 2144 CD ARG 272 39.442 44.981 68.089 1.00 85.70
ATOM 2073 CD2 PHE 264 42.278 32.912 73.367 1.00 22.79   ATOM 2145 NE ARG 272 40.254 44.110 37.231 1.00 93.83
ATOM 2074 CE1 PHE 264 44.405 31.848 71.940 0.00 26.06   ATOM 2146 HE ARG 272 40.797 44.536 66.532 1.00 0.00
ATOM 2075 CE2 PHE 264 43.404 21.478 74.048 1.00 21.09   ATOM 2147 CZ ARG 272 40.322 42.782 67.330 1.00 95.55
ATOM 2076 CZ PHE 264 44.466 31.946 37.343 1.00 21.31    ATOM 2148 NH1 ARG 272 39.630 42.134 68.259 1.00 96.47
ATOM 2077 C PHE 264 38.607 34.044 71.416 1.00 21.61     ATOM 2149 HH11 ARG 272 39.059 42.641 68.899 1.00 0.00
ATOM 2078 O PHE 264 38.416 35.172 71.876 1.00 19.64     ATOM 2150 HH12 ARG 272 39.694 41.143 68.323 1.00 0.00
ATOM 2079 N THR 265 37.894 33.559 70.399 1.00 20.39     ATOM 2151 NH2 ARG 272 41.063 42.095 66.470 1.00 96.37
ATOM 2080 H THR 265 38.052 32.647 70.081 1.00 0.00      ATOM 2152 HH21 ARG 272 41.576 42.569 65.754 1.00 0.00
ATOM 2081 CA THR 265 36.881 34.398 69.768 1.00 18.63    ATOM 2153 HH22 ARG 272 41.118 41.098 66.541 1.00 0.00
```

-continued

```
ATOM   2082  CB   THR 265  36.498 33.895 68.327 1.00 19.30    ATOM   2154  C    ARG 272  35.780 44.004 64.770 1.00 60.35
ATOM   2083  OG1  THR 265  35.599 32.793 68.407 1.00 33.53    ATOM   2155  O    ARG 272  36.385 44.703 63.959 1.00 62.79
ATOM   2084  HG1  THR 265  36.008 32.055 68.896 1.00 0.00     ATOM   2156  N    GLY 273  34.888 43.091 64.395 1.00 55.94
ATOM   2085  CG2  THR 265  37.704 33.409 67.602 1.00 13.43    ATOM   2157  H    GLY 273  34.429 42.558 65.070 1.00 0.00
ATOM   2086  C    THR 265  35.651 34.566 70.656 1.00 17.69    ATOM   2158  CA   GLY 273  34.595 42.894 62.982 1.00 51.40
ATOM   2087  O    THR 265  34.974 35.589 70.602 1.00 18.30    ATOM   2159  C    GLY 273  35.535 41.975 62.206 1.00 48.56
ATOM   2088  N    LEU 266  35.435 33.593 71.538 1.00 20.96    ATOM   2160  O    GLY 273  35.579 42.007 60.970 1.00 48.16
ATOM   2089  H    LEU 266  36.057 32.840 71.566 1.00 0.00     ATOM   2161  N    LEU 274  36.285 41.150 62.927 1.00 43.81
ATOM   2090  CA   LEU 266  34.300 33.579 72.470 1.00 19.74    ATOM   2162  H    LEU 274  36.219 41.166 62.898 1.00 0.00
ATOM   2091  CB   LEU 266  34.068 32.130 72.973 1.00 18.59    ATOM   2163  CA   LEU 274  37.211 40.215 62.312 1.00 37.25
ATOM   2092  CG   LEU 266  32.903 31.615 73.755 1.00 16.93    ATOM   2164  CB   LEU 274  38.187 39.675 63.368 1.00 33.69
ATOM   2093  CD1  LEU 266  31.609 31.566 72.964 1.00 16.73    ATOM   2165  CG   LEU 274  39.310 38.767 62.689 1.00 33.59
ATOM   2094  CD2  LEU 266  33.269 30.208 74.169 1.00 23.03    ATOM   2166  CD1  LEU 274  40.366 39.624 62.218 1.00 33.98
ATOM   2095  C    LEU 266  34.580 34.447 73.691 1.00 19.29    ATOM   2167  CD2  LEU 274  39.919 37.969 64.005 1.00 33.40
ATOM   2096  O    LEU 266  33.709 35.164 74.184 1.00 18.02    ATOM   2168  C    LEU 274  36.407 39.060 61.725 1.00 33.64
ATOM   2097  N    THR 267  35.811 34.361 74.175 1.00 22.16    ATOM   2169  O    LEU 274  35.660 38.393 62.444 1.00 32.62
ATOM   2098  H    THR 267  36.455 33.791 73.722 1.00 0.00     ATOM   2170  N    GLN 275  36.528 38.832 60.421 1.00 30.31
ATOM   2099  CA   THR 267  36.230 35.087 75.356 1.00 22.07    ATOM   2171  H    GLN 275  37.100 39.403 59.880 1.00 0.00
ATOM   2100  CB   THR 267  37.300 34.303 76.090 1.00 17.69    ATOM   2172  CA   GLN 275  35.805 37.720 59.808 1.00 25.26
ATOM   2101  OG1  THR 267  38.380 34.019 75.198 1.00 16.60    ATOM   2173  CB   GLN 275  36.086 37.628 58.298 1.00 19.14
ATOM   2102  HG1  THR 267  38.051 33.496 74.464 1.00 0.00     ATOM   2174  CG   GLN 275  35.616 38.829 57.480 1.00 19.44
ATOM   2103  CG2  THR 267  36.727 32.995 76.593 1.00 17.07    ATOM   2175  CD   GLN 275  34.103 39.057 57.506 1.00 16.85
ATOM   2104  C    THR 267  36.699 36.518 75.151 1.00 28.83    ATOM   2176  OE1  GLN 275  33.316 38.130 57.676 1.00 23.53
ATOM   2105  O    THR 267  36.531 37.355 76.036 1.00 32.54    ATOM   2177  NE2  GLN 275  33.696 40.294 57.319 1.00 15.80
ATOM   2106  N    VAL 268  37.302 36.811 74.005 1.00 32.30    ATOM   2178  HE21 GLN 275  34.357 41.007 57.184 1.00 0.00
ATOM   2107  H    VAL 268  37.429 36.117 73.331 1.00 0.00     ATOM   2179  HE22 GLN 275  32.739 40.465 57.338 1.00 0.00
ATOM   2108  CA   VAL 268  37.789 38.163 73.745 1.00 36.85    ATOM   2180  C    GLN 275  36.303 36.451 60.494 1.00 24.15
ATOM   2109  CB   VAL 268  38.437 38.528 72.326 1.00 36.24    ATOM   2181  O    GLN 275  37.432 36.412 60.993 1.00 26.83
ATOM   2110  CG1  VAL 268  37.415 38.714 71.275 1.00 30.68    ATOM   2182  N    ARG 276  35.451 35.440 60.570 1.00 21.69
ATOM   2111  CG2  VAL 268  39.691 39.115 72.357 1.00 27.04    ATOM   2183  H    ARG 276  34.548 35.536 60.213 1.00 0.00
ATOM   2112  C    VAL 268  36.627 39.156 73.898 1.00 43.33    ATOM   2184  CA   ARG 276  35.838 34.164 61.167 1.00 19.65
ATOM   2113  O    VAL 268  35.847 38.847 73.545 1.00 43.53    ATOM   2185  CB   ARG 276  34.647 33.192 61.111 1.00 17.59
ATOM   2114  N    PRO 269  36.887 40.337 74.489 1.00 48.08    ATOM   2186  CG   ARG 276  33.468 33.638 62.002 1.00 15.00
ATOM   2115  CD   PRO 269  38.152 40.854 75.035 1.00 51.38    ATOM   2187  CD   ARG 276  33.857 33.488 63.474 1.00 14.70
ATOM   2116  CA   PRO 269  35.816 41.321 74.659 1.00 52.01    ATOM   2188  NE   ARG 276  33.091 34.297 64.418 1.00 12.83
ATOM   2117  CB   PRO 269  36.545 42.530 75.529 1.00 50.38    ATOM   2189  HE   ARG 276  33.399 35.210 64.577 1.00 0.00
ATOM   2118  CG   PRO 269  37.971 42.331 74.848 1.00 52.06    ATOM   2190  CZ   ARG 276  31.999 33.886 65.065 1.00 18.90
ATOM   2119  C    PRO 269  35.162 41.648 73.322 1.00 54.55    ATOM   2191  NH1  ARG 276  31.499 32.668 64.883 1.00 19.00
ATOM   2120  O    PRO 269  33.935 41.638 73.194 1.00 55.57    ATOM   2192  HH11 ARG 276  31.935 32.030 64.261 1.00 0.00
ATOM   2121  N    SER 270  35.983 41.898 72.311 1.00 56.02    ATOM   2193  HH12 ARG 276  30.673 32.393 65.386 1.00 0.00
ATOM   2122  H    SER 270  36.951 41.870 72.440 1.00 0.00     ATOM   2194  NH2  ARG 276  31.422 34.687 65.948 1.00 18.90
ATOM   2123  CA   SER 270  35.433 42.204 71.010 1.00 55.44    ATOM   2195  HH21 ARG 276  31.812 35.596 66.119 1.00 0.00
ATOM   2124  CB   SER 270  35.222 43.713 70.850 1.00 59.59    ATOM   2196  HH22 ARG 276  30.603 34.397 66.434 1.00 0.00
ATOM   2125  OG   SER 270  34.455 44.000 69.687 1.00 63.26    ATOM   2197  C    ARG 276  37.059 33.661 60.369 1.00 19.56
ATOM   2126  HG   SER 270  33.591 43.592 69.782 1.00 0.00     ATOM   2198  O    ARG 276  37.226 34.020 59.203 1.00 18.15
ATOM   2127  C    SER 270  36.269 41.663 69.866 1.00 53.06    ATOM   2199  N    ARG 277  37.906 32.846 60.988 1.00 15.03
ATOM   2128  O    SER 270  37.502 41.682 69.900 1.00 48.03    ATOM   2200  H    ARG 277  37.712 32.558 61.903 1.00 0.00
ATOM   2129  N    GLU 271  35.556 41.139 68.876 1.00 53.04    ATOM   2201  CA   ARG 277  39.131 32.373 60.341 1.00 17.54
ATOM   2130  H    GLU 271  34.585 41.106 68.983 1.00 0.00     ATOM   2202  CB   ARG 277  40.292 32.406 61.347 1.00 16.22
ATOM   2131  CA   GLU 271  36.147 40.597 67.667 1.00 54.48    ATOM   2203  CG   ARG 277  40.521 33.775 62.033 1.00 19.01
ATOM   2131  CB   GLU 271  35.123 39.725 66.938 1.00 54.93    ATOM   2204  CD   ARG 277  41.174 34.832 61.126 1.00 19.17
ATOM   2133  CG   GLU 271  34.516 38.613 67.795 1.00 54.99    ATOM   2205  NE   ARG 277  40.214 35.788 60.564 1.00 26.26
ATOM   2134  CD   GLU 271  33.349 37.911 67.114 1.00 52.97    ATOM   2206  HE   ARG 277  39.293 35.742 60.887 1.00 0.00
ATOM   2207  CZ   ARG 277  40.511 36.715 59.646 1.00 24.81    ATOM   2279  CB   ALA 283  40.798 23.264 63.007 1.00 18.53
ATOM   2208  NH1  ARG 277  41.741 36.830 59.166 1.00 26.15    ATOM   2280  C    ALA 283  38.766 21.855 62.555 1.00 16.97
ATOM   2209  HH11 ARG 277  42.464 36.211 59.491 1.00 0.00     ATOM   2281  O    ALA 283  38.775 20.702 62.988 1.00 14.00
ATOM   2210  HH12 ARG 277  41.951 37.512 58.472 1.00 0.00     ATOM   2282  N    LEU 284  37.695 22.632 62.611 1.00 15.85
ATOM   2211  NH2  ARG 277  39.573 37.528 59.195 1.00 26.84    ATOM   2283  H    LEU 284  37.747 23.542 62.250 1.00 0.00
ATOM   2212  HH21 ARG 277  38.640 37.451 59.538 1.00 0.00     ATOM   2284  CA   LEU 284  36.454 22.165 63.202 1.00 16.34
ATOM   2213  HH22 ARG 277  39.803 38.208 58.500 1.00 0.00     ATOM   2285  CB   LEU 284  35.806 23.300 63.996 1.00 9.09
ATOM   2214  C    ARG 277  39.086 31.009 59.646 1.00 17.93    ATOM   2286  CG   LEU 284  36.690 23.937 65.073 1.00 8.16
ATOM   2215  O    ARG 277  38.617 30.034 60.207 1.00 17.46    ATOM   2287  CD1  LEU 284  36.018 25.180 65.567 1.00 8.60
ATOM   2216  N    ARG 278  39.616 30.941 58.431 1.00 17.74    ATOM   2288  CD2  LEU 284  36.938 22.963 66.204 1.00 5.36
ATOM   2217  H    ARG 278  39.984 31.756 58.032 1.00 0.00     ATOM   2289  C    LEU 284  35.423 21.544 62.250 1.00 20.99
ATOM   2218  CA   ARG 278  39.638 29.695 57.669 1.00 19.27    ATOM   2290  O    LEU 284  34.694 20.633 62.657 1.00 23.47
ATOM   2219  CB   ARG 278  40.315 29.913 56.302 1.00 26.70    ATOM   2291  N    ASN 285  35.363 22.006 60.999 1.00 20.31
ATOM   2220  CG   ARG 278  40.541 28.655 55.424 1.00 30.07    ATOM   2292  H    ASN 285  35.985 22.707 60.724 1.00 0.00
ATOM   2221  CD   ARG 278  39.279 28.146 54.708 1.00 33.95    ATOM   2293  CA   ASN 285  34.378 21.494 60.024 1.00 26.25
ATOM   2222  NE   ARG 278  39.490 26.851 54.037 1.00 38.49    ATOM   2294  CB   ASN 285  34.666 21.980 58.605 1.00 21.03
ATOM   2223  HE   ARG 278  39.252 26.054 54.517 1.00 0.00     ATOM   2295  CG   ASN 285  34.267 23.431 58.407 1.00 21.30
ATOM   2224  CZ   ARG 278  39.961 26.681 52.795 1.00 38.09    ATOM   2296  OD1  ASN 285  33.589 24.020 59.255 1.00 22.55
ATOM   2225  NH1  ARG 278  40.283 37.726 52.039 1.00 35.69    ATOM   2297  ND2  ASN 285  34.698 24.022 57.304 1.00 19.92
ATOM   2226  HH11 ARG 278  40.179 28.656 52.402 1.00 0.00     ATOM   2298  HD21 ASN 285  35.246 23.532 56.665 1.00 0.00
ATOM   2227  HH12 ARG 278  40.648 27.595 51.119 1.00 0.00     ATOM   2299  HD21 ASN 285  34.444 24.968 57.168 1.00 0.00
ATOM   2228  NH2  ARG 278  40.121 25.452 52.312 1.00 33.68    ATOM   2300  C    ASN 285  34.068 20.007 60.040 1.00 28.14
ATOM   2229  HH21 ARG 278  39.871 24.660 52.860 1.00 0.00     ATOM   2301  O    ASN 285  32.906 19.631 59.964 1.00 28.81
ATOM   2230  HH22 ARG 278  40.472 25.329 51.380 1.00 0.00     ATOM   2302  N    GLY 286  35.088 19.156 60.051 1.00 34.18
ATOM   2231  C    ARG 278  40.352 28.582 58.416 1.00 17.18    ATOM   2303  H    GLY 286  36.000 19.483 60.013 1.00 0.00
ATOM   2232  O    ARG 278  39.894 27.448 58.396 1.00 19.40    ATOM   2304  CA   GLY 286  34.821 17.727 60.158 1.00 39.04
```

-continued

| | |
|---|---|
| ATOM 2233 N PHE 279 41.461 28.895 59.087 1.00 17.77 | ATOM 2305 C GLY 286 34.957 16.711 59.036 1.00 39.96 |
| ATOM 2234 H PHE 279 41.786 29.820 59.100 1.00 0.00 | ATOM 2306 O GLY 286 34.456 15.589 59.201 1.00 45.42 |
| ATOM 2235 CA PHE 279 42.198 27.853 59.796 1.00 13.89 | ATOM 2307 N ASN 287 35.625 17.078 57.937 1.00 34.10 |
| ATOM 2236 CB PHE 279 43.552 28.347 60.342 1.00 14.71 | ATOM 2308 H ASN 287 35.974 17.984 57.918 1.00 0.00 |
| ATOM 2237 CG PHE 279 43.484 29.183 61.607 1.00 15.65 | ATOM 2309 CA ASN 287 35.861 16.211 56.761 1.00 29.60 |
| ATOM 2238 CD1 PHE 279 43.717 28.594 62.858 1.00 18.80 | ATOM 2310 CB ASN 287 36.539 14.865 57.139 1.00 34.52 |
| ATOM 2239 CD2 PHE 279 43.341 30.571 61.542 1.00 15.68 | ATOM 2311 CG ASN 287 35.548 13.700 57.352 1.00 40.80 |
| ATOM 2240 CE1 PHE 279 43.823 29.369 64.033 1.00 13.51 | ATOM 2312 OD1 ASN 287 34.322 13.886 57.421 1.00 43.97 |
| ATOM 2241 CE2 PHE 279 43.447 31.359 62.710 1.00 19.29 | ATOM 2313 ND2 ASN 287 36.094 12.484 57.464 1.00 36.28 |
| ATOM 2242 CZ PHE 279 43.691 30.750 63.958 1.00 14.33 | ATOM 2314 HD21 ASN 287 37.057 12.835 57.409 1.00 0.00 |
| ATOM 2243 C PHE 279 41.365 27.191 60.865 1.00 14.00 | ATOM 2315 HD22 ASN 287 35.475 11.736 57.596 1.00 0.00 |
| ATOM 2244 O PHE 279 41.463 25.985 61.082 1.00 13.69 | ATOM 2316 C ASN 287 34.737 16.009 55.741 1.00 25.40 |
| ATOM 2245 N VAL 280 40.511 27.979 61.503 1.00 16.14 | ATOM 2317 O ASN 287 34.931 15.338 54.730 1.00 22.82 |
| ATOM 2246 H VAL 280 40.460 28.923 61.263 1.00 0.00 | ATOM 2318 N GLY 288 33.576 16.602 55.991 1.00 19.10 |
| ATOM 2247 CA VAL 280 39.635 27.464 62.543 1.00 14.61 | ATOM 2319 H GLY 288 33.455 17.110 56.808 1.00 0.00 |
| ATOM 2248 CB VAL 280 39.015 28.620 63.371 1.00 16.28 | ATOM 2320 CA GLY 288 32.475 16.497 55.048 1.00 18.41 |
| ATOM 2249 CG1 VAL 280 37.946 28.083 64.339 1.00 12.84 | ATOM 2321 C GLY 288 31.564 15.295 55.133 1.00 17.17 |
| ATOM 2250 CG2 VAL 280 40.118 29.344 64.129 1.00 12.25 | ATOM 2322 O GLY 288 30.639 15.168 54.342 1.00 14.79 |
| ATOM 2251 C VAL 280 38.543 26.653 61.872 1.00 12.07 | ATOM 2323 N ASP 289 31.823 14.404 56.079 1.00 19.90 |
| ATOM 2252 O VAL 280 38.233 25.531 62.294 1.00 15.69 | ATOM 2324 H ASP 289 32.585 14.563 56.676 1.00 0.00 |
| ATOM 2253 N GLN 281 38.003 27.202 60.791 1.00 12.46 | ATOM 2325 CA ASP 289 31.015 13.208 56.269 1.00 17.92 |
| ATOM 2254 H GLN 281 38.323 28.080 60.492 1.00 0.00 | ATOM 2326 CB ASP 289 31.700 12.331 57.328 1.00 24.19 |
| ATOM 2255 CA GLN 281 36.946 26.541 60.046 1.00 12.48 | ATOM 2327 CG ASP 289 31.065 10.951 57.479 1.00 27.65 |
| ATOM 2256 CB GLN 281 36.460 27.428 58.890 1.00 12.05 | ATOM 2328 OD1 ASP 289 30.310 10.489 56.596 1.00 32.15 |
| ATOM 2257 CG GLN 281 35.85 28.769 59.325 1.00 15.34 | ATOM 2329 OD2 ASP 289 31.352 10.310 58.507 1.00 37.02 |
| ATOM 2258 CD GLN 281 35.847 29.820 58.199 1.00 18.27 | ATOM 2330 C ASP 289 29.614 13.609 56.745 1.00 19.07 |
| ATOM 2259 OE1 GLN 281 36.473 29.640 57.151 1.00 21.65 | ATOM 2331 O ASP 289 29.464 14.189 57.829 1.00 17.44 |
| ATOM 2260 NE2 GLN 281 35.182 30.939 58.442 1.00 16.98 | ATOM 2332 N PRO 290 28.566 13.315 55.950 1.00 16.17 |
| ATOM 2261 HE21 GLN 281 34.726 31.050 59.312 1.00 0.00 | ATOM 2333 CD PRO 290 28.532 12.778 54.573 1.00 14.59 |
| ATOM 2262 HE22 GLN 281 35.161 31.610 57.734 1.00 0.00 | ATOM 2334 CA PRO 290 27.221 13.689 56.397 1.00 14.74 |
| ATOM 2263 C GLN 281 37.437 25.197 59.522 1.00 13.34 | ATOM 2335 CB PRO 290 26.333 13.334 55.195 1.00 12.58 |
| ATOM 2264 O GLN 281 36.746 24.192 59.640 1.00 16.51 | ATOM 2336 CG PRO 290 27.116 12.282 54.458 1.00 13.57 |
| ATOM 2265 N ASN 282 38.656 25.149 59.010 1.00 14.65 | ATOM 2337 C PRO 290 26.771 12.973 57.670 1.00 16.11 |
| ATOM 2266 H ASN 282 39.205 25.937 58.997 1.00 0.00 | ATOM 2338 O PRO 290 25.947 13.495 58.423 1.00 17.73 |
| ATOM 2267 CA ASN 282 39.175 23.897 58.493 1.00 13.22 | ATOM 2339 N ASN 291 27.316 11.784 57.919 1.00 15.95 |
| ATOM 2268 CB ASN 282 40.482 24.125 57.766 1.00 22.94 | ATOM 2340 H ASN 291 27.977 11.429 57.290 1.00 0.00 |
| ATOM 2269 CG ASN 282 40.298 24.887 56.482 1.00 26.80 | ATOM 2341 CA ASN 291 26.934 11.010 59.098 1.00 15.36 |
| ATOM 2270 OD1 ASN 282 39.206 24.902 55.902 1.00 26.92 | ATOM 2342 CB ASN 291 27.544 9.607 59.045 1.00 20.14 |
| ATOM 2271 ND2 ASN 282 41.366 25.534 56.025 1.00 29.37 | ATOM 2343 CG ASN 291 26.957 8.751 57.914 1.00 29.95 |
| ATOM 2272 HD21 ASN 282 42.201 25.499 56.524 1.00 0.00 | ATOM 2344 OD1 ASN 291 25.764 8.840 57.603 1.00 27.64 |
| ATOM 2273 HD22 ASN 282 41.250 26.042 55.195 1.00 0.00 | ATOM 2345 ND2 ASN 291 27.800 7.926 57.287 1.00 35.21 |
| ATOM 2274 C ASN 282 39.381 22.867 59.575 1.00 16.97 | ATOM 2346 HD21 ASN 291 28.743 7.888 57.559 1.00 0.00 |
| ATOM 2275 O ASN 282 39.181 21.676 59.346 1.00 15.36 | ATOM 2347 HD22 ASN 291 27.439 7.374 56.563 1.00 0.00 |
| ATOM 2276 N ALA 283 39.770 23.335 60.758 1.00 17.24 | ATOM 2348 C ASN 291 27.338 11.725 60.376 1.00 15.24 |
| ATOM 2277 H ALA 283 39.905 24.298 60.854 1.00 0.00 | ATOM 2349 O ASN 291 26.555 11.838 61.326 1.00 14.36 |
| ATOM 2278 CA ALA 283 40.023 22.474 61.927 1.00 20.01 | ATOM 2350 N ASN 292 28.562 12.227 60.383 1.00 13.11 |
| ATOM 2351 H ASN 292 29.154 12.105 59.616 1.00 0.00 | ATOM 2423 CG LEU 299 26.056 18.212 70.751 1.00 5.81 |
| ATOM 2352 CA ASN 292 29.087 12.956 61.516 1.00 13.18 | ATOM 2424 CD1 LEU 299 25.444 17.859 72.104 1.00 5.01 |
| ATOM 2353 CB ASN 292 30.596 13.107 61.355 1.00 19.78 | ATOM 2425 CD2 LEU 299 27.537 17.895 70.753 1.00 3.65 |
| ATOM 2354 CG ASN 292 31.211 14.071 62.302 1.00 28.71 | ATOM 2426 C LEU 299 23.402 19.024 69.742 1.00 9.73 |
| ATOM 2355 OD1 ASN 292 31.514 15.209 61.938 1.00 29.73 | ATOM 2427 O LEU 299 22.973 19.451 70.808 1.00 13.20 |
| ATOM 2356 ND2 ASN 292 31.412 13.630 63.545 1.00 34.11 | ATOM 2428 N TYR 300 23.510 19.781 68.653 1.00 10.11 |
| ATOM 2357 HD21 ASN 292 31.183 12.741 63.846 1.00 0.00 | ATOM 2429 H TYR 300 23.872 19.379 67.834 1.00 0.00 |
| ATOM 2358 HD22 ASN 292 31.760 14.303 64.150 1.00 0.00 | ATOM 2430 CA TYR 300 23.122 21.186 68.629 1.00 9.02 |
| ATOM 2359 C ASN 292 28.362 14.309 61.643 1.00 13.32 | ATOM 2431 CB TYR 300 23.367 21.785 67.241 1.00 7.95 |
| ATOM 2360 O ASN 292 28.010 14.731 62.741 1.00 15.59 | ATOM 2432 CG TYR 300 22.788 23.158 67.068 1.00 10.20 |
| ATOM 2361 N MET 293 28.057 14.946 60.514 1.00 14.57 | ATOM 2433 CD1 TYR 300 23.295 24.238 67.779 1.00 16.87 |
| ATOM 2362 H MET 293 28.334 14.557 59.661 1.00 0.00 | ATOM 2434 CE1 TYR 300 22.747 25.512 67.643 1.00 15.45 |
| ATOM 2363 CA MET 293 27.336 16.222 60.527 1.00 11.47 | ATOM 2435 CD2 TYR 300 21.717 23.379 66.210 1.00 9.46 |
| ATOM 2364 CB MET 293 27.230 16.798 59.111 1.00 11.95 | ATOM 2436 CE2 TYR 300 21.162 24.646 66.059 1.00 8.57 |
| ATOM 2365 CG MET 293 28.489 17.469 58.600 1.00 17.06 | ATOM 2437 CZ TYR 300 21.680 25.704 66.774 1.00 14.54 |
| ATOM 2366 SD MET 293 29.105 18.779 59.711 1.00 21.66 | ATOM 2438 OH TYR 300 21.169 26.969 66.597 1.00 17.24 |
| ATOM 2367 CE MET 293 27.790 20.093 59.487 1.00 17.21 | ATOM 2439 HH TYR 300 21.605 27.561 67.185 1.00 0.00 |
| ATOM 2368 C MET 293 25.928 16.047 61.119 1.00 11.57 | ATOM 2440 C TYR 300 21.660 21.374 69.014 1.00 6.78 |
| ATOM 2369 O MET 293 25.407 16.938 61.809 1.00 13.99 | ATOM 2441 O TYR 300 21.318 22.323 69.072 1.00 11.35 |
| ATOM 2370 N ASP 294 25.319 14.894 60.842 1.00 11.64 | ATOM 2442 N ARG 301 20.796 20.490 68.542 1.00 5.73 |
| ATOM 2371 H ASP 294 25.785 14.237 60.287 1.00 0.00 | ATOM 2443 H ARG 301 21.109 19.768 67.960 1.00 0.00 |
| ATOM 2372 CA ASP 294 23.984 14.571 61.326 1.00 11.13 | ATOM 2444 CA ARG 301 19.384 20.569 68.865 1.00 7.64 |
| ATOM 2373 CB ASP 294 23.558 13.193 60.804 1.00 11.26 | ATOM 2445 CB ARG 301 18.647 19.416 68.174 1.00 8.01 |
| ATOM 2374 CG ASP 294 22.290 12.661 61.475 1.00 12.41 | ATOM 2446 CG ARG 301 17.181 19.168 68.563 1.00 14.79 |
| ATOM 2375 OD1 ASP 294 21.227 13.331 61.454 1.00 12.07 | ATOM 2447 CD ARG 301 16.339 18.583 67.379 1.00 20.64 |
| ATOM 2376 OD2 ASP 294 22.363 11.541 62.023 1.00 14.66 | ATOM 2448 NE ARG 301 17.140 17.736 66.487 1.00 28.98 |
| ATOM 2377 C ASP 294 24.031 14.572 62.842 1.00 11.54 | ATOM 2449 HE ARG 301 17.909 17.271 66.872 1.00 0.00 |
| ATOM 2378 O ASP 294 23.175 15.168 53.493 1.00 10.58 | ATOM 2450 CZ ARG 301 16.905 17.539 65.186 1.00 31.08 |
| ATOM 2379 N LYS 295 25.073 13.947 63.385 1.00 9.77 | ATOM 2451 NH1 ARG 301 15.867 18.122 64.590 1.00 20.46 |
| ATOM 2380 H LYS 295 25.736 13.544 62.788 1.00 0.00 | ATOM 2452 HH11 ARG 301 15.253 18.717 65.106 1.00 0.00 |
| ATOM 2381 CA LYS 295 25.274 13.844 64.820 1.00 11.01 | ATOM 2453 HH12 ARG 301 15.702 17.971 63.611 1.00 0.00 |
| ATOM 2382 CB LYS 295 26.405 12.861 65.132 1.00 12.17 | ATOM 2454 NH2 ARG 301 17.736 16.769 64.470 1.00 29.91 |
| ATOM 2383 CG LYS 295 26.112 11.414 64.721 1.00 15.92 | ATOM 2455 HH21 ARG 301 18.524 16.341 64.906 1.00 0.00 |

-continued

| | | | | | | | | | | | | | | |
|---|---|---|---|---|---|---|---|---|---|---|---|---|---|---|
| ATOM | 2384 | CD | LYS | 295 | 24.745 | 10.935 | 65.238 | 1.00 | 26.08 | ATOM | 2456 | HH22 | ARG | 301 | 17.561 | 16.620 | 63.493 | 1.00 | 0.00 |
| ATOM | 2385 | CE | LYS | 295 | 24.650 | 10.986 | 66.779 | 1.00 | 32.27 | ATOM | 2457 | C | ARG | 301 | 19.255 | 20.508 | 70.392 | 1.00 | 11.97 |
| ATOM | 2386 | NZ | LYS | 295 | 23.340 | 10.508 | 67.328 | 1.00 | 35.24 | ATOM | 2458 | O | ARG | 301 | 18.539 | 21.306 | 71.008 | 1.00 | 8.66 |
| ATOM | 2387 | HZ1 | LYS | 295 | 23.187 | 9.519 | 67.040 | 1.00 | 0.00 | ATOM | 2459 | N | LYS | 302 | 20.032 | 19.621 | 71.005 | 1.00 | 12.43 |
| ATOM | 2388 | HZ2 | LYS | 295 | 22.568 | 11.098 | 66.951 | 1.00 | 0.00 | ATOM | 2460 | H | LYS | 302 | 20.624 | 19.048 | 70.476 | 1.00 | 0.00 |
| ATOM | 2389 | HZ3 | LYS | 295 | 23.355 | 10.573 | 68.362 | 1.00 | 0.00 | ATOM | 2461 | CA | LYS | 302 | 20.001 | 19.473 | 72.456 | 1.00 | 13.80 |
| ATOM | 2390 | C | LYS | 295 | 25.576 | 15.194 | 65.449 | 1.00 | 9.04 | ATOM | 2462 | CB | LYS | 302 | 20.659 | 18.163 | 72.872 | 1.00 | 11.66 |
| ATOM | 2391 | O | LYS | 295 | 25.142 | 15.478 | 66.568 | 1.00 | 10.34 | ATOM | 2463 | CG | LYS | 302 | 19.857 | 16.963 | 72.470 | 1.00 | 10.77 |
| ATOM | 2392 | N | ALA | 296 | 26.345 | 16.017 | 64.746 | 1.00 | 7.72 | ATOM | 2464 | CD | LYS | 302 | 20.610 | 15.694 | 72.793 | 1.00 | 10.43 |
| ATOM | 2393 | H | ALA | 296 | 26.690 | 15.740 | 63.873 | 1.00 | 0.00 | ATOM | 2465 | CE | LYS | 302 | 19.802 | 14.507 | 72.347 | 1.00 | 11.53 |
| ATOM | 2394 | CA | ALA | 296 | 26.671 | 17.333 | 65.621 | 1.00 | 5.19 | ATOM | 2466 | NZ | LYS | 302 | 20.469 | 13.216 | 72.662 | 1.00 | 13.56 |
| ATOM | 2395 | CB | ALA | 296 | 27.715 | 18.004 | 64.381 | 1.00 | 6.61 | ATOM | 2467 | HZ1 | LYS | 302 | 20.601 | 13.136 | 73.690 | 1.00 | 0.00 |
| ATOM | 2396 | C | ALA | 296 | 25.392 | 18.172 | 65.358 | 1.00 | 6.09 | ATOM | 2468 | HZ2 | LYS | 302 | 21.393 | 13.174 | 81.187 | 1.00 | 0.00 |
| ATOM | 2397 | O | ALA | 296 | 25.250 | 18.972 | 66.277 | 1.00 | 8.56 | ATOM | 2469 | HZ3 | LYS | 302 | 19.871 | 12.432 | 72.327 | 1.00 | 0.00 |
| ATOM | 2398 | N | VAL | 297 | 24.444 | 17.955 | 64.434 | 1.00 | 10.76 | ATOM | 2470 | C | LYS | 302 | 20.615 | 20.659 | 73.195 | 1.00 | 10.42 |
| ATOM | 2399 | H | VAL | 297 | 24.613 | 17.284 | 63.743 | 1.00 | 0.00 | ATOM | 2471 | O | LYS | 302 | 20.032 | 21.158 | 74.153 | 1.00 | 10.98 |
| ATOM | 2400 | CA | VAL | 297 | 23.162 | 18.673 | 64.415 | 1.00 | 7.41 | ATOM | 2472 | N | LEU | 303 | 21.766 | 21.128 | 72.730 | 1.00 | 6.22 |
| ATOM | 2401 | CB | VAL | 297 | 22.457 | 18.528 | 63.038 | 1.00 | 8.39 | ATOM | 2473 | H | LEU | 303 | 22.179 | 20.704 | 71.953 | 1.00 | 0.00 |
| ATOM | 2402 | CG1 | VAL | 297 | 21.046 | 19.133 | 63.088 | 1.00 | 8.02 | ATOM | 2474 | CA | LEU | 303 | 22.419 | 22.262 | 73.349 | 1.00 | 10.05 |
| ATOM | 2403 | CG2 | VAL | 297 | 23.293 | 19.198 | 61.971 | 1.00 | 3.74 | ATOM | 2475 | CB | LEU | 303 | 23.755 | 22.554 | 72.689 | 1.00 | 7.08 |
| ATOM | 2404 | C | VAL | 297 | 22.226 | 18.206 | 65.526 | 1.00 | 5.23 | ATOM | 2476 | CG | LEU | 303 | 24.884 | 21.545 | 72.876 | 1.00 | 10.45 |
| ATOM | 2405 | O | VAL | 297 | 21.463 | 18.982 | 66.087 | 1.00 | 8.24 | ATOM | 2477 | CD1 | LEU | 303 | 26.131 | 22.045 | 72.162 | 1.00 | 10.81 |
| ATOM | 2406 | N | LYS | 298 | 22.247 | 16.917 | 65.800 | 1.00 | 6.55 | ATOM | 2478 | CD2 | LEU | 303 | 25.193 | 21.339 | 74.328 | 1.00 | 6.09 |
| ATOM | 2407 | H | LYS | 298 | 22.817 | 16.323 | 65.271 | 1.00 | 0.00 | ATOM | 2479 | C | LEU | 303 | 21.571 | 23.524 | 73.310 | 1.00 | 16.52 |
| ATOM | 2408 | CA | LYS | 298 | 21.442 | 16.349 | 66.869 | 1.00 | 7.19 | ATOM | 2480 | O | LEU | 303 | 21.736 | 24.392 | 74.168 | 1.00 | 18.88 |
| ATOM | 2409 | CB | LYS | 298 | 21.566 | 14.828 | 66.867 | 1.00 | 7.37 | ATOM | 2481 | N | LYS | 304 | 20.659 | 23.607 | 72.336 | 1.00 | 18.39 |
| ATOM | 2410 | CG | LYS | 298 | 20.667 | 14.133 | 65.879 | 1.00 | 15.04 | ATOM | 2482 | H | LYS | 304 | 20.588 | 22.865 | 71.696 | 1.00 | 0.00 |
| ATOM | 2411 | CD | LYS | 298 | 21.327 | 12.896 | 65.347 | 1.00 | 20.63 | ATOM | 2483 | CA | LYS | 304 | 19.769 | 24.766 | 72.150 | 1.00 | 20.75 |
| ATOM | 2412 | CE | LYS | 298 | 20.322 | 12.005 | 64.644 | 1.00 | 28.28 | ATOM | 2484 | CB | LYS | 304 | 18.923 | 25.594 | 70.882 | 1.00 | 23.75 |
| ATOM | 2413 | NZ | LYS | 298 | 19.419 | 12.789 | 63.771 | 1.00 | 37.61 | ATOM | 2485 | CG | LYS | 304 | 19.216 | 25.550 | 69.747 | 1.00 | 31.46 |
| ATOM | 2414 | HZ1 | LYS | 298 | 19.980 | 13.301 | 63.063 | 1.00 | 0.00 | ATOM | 2486 | CD | LYS | 304 | 18.784 | 26.980 | 70.060 | 1.00 | 44.15 |
| ATOM | 2415 | HZ2 | LYS | 298 | 18.901 | 13.478 | 64.358 | 1.00 | 0.00 | ATOM | 2487 | CE | LYS | 304 | 18.941 | 27.875 | 68.834 | 1.00 | 45.35 |
| ATOM | 2416 | HZ3 | LYS | 298 | 18.748 | 12.156 | 63.304 | 1.00 | 0.00 | ATOM | 2488 | NZ | LYS | 304 | 18.712 | 29.306 | 69.151 | 1.00 | 51.31 |
| ATOM | 2417 | C | LYS | 298 | 21.943 | 16.907 | 68.204 | 1.00 | 7.36 | ATOM | 2489 | HZ1 | LYS | 304 | 19.398 | 29.618 | 69.868 | 1.00 | 0.00 |
| ATOM | 2418 | O | LYS | 298 | 21.145 | 17.190 | 69.089 | 1.00 | 9.72 | ATOM | 2490 | HZ2 | LYS | 304 | 17.747 | 29.434 | 69.514 | 1.00 | 0.00 |
| ATOM | 2419 | N | LEU | 299 | 23.263 | 16.984 | 68.376 | 1.00 | 7.00 | ATOM | 2491 | HZ3 | LYS | 304 | 18.836 | 29.875 | 68.287 | 1.00 | 0.00 |
| ATOM | 2420 | H | LEU | 299 | 23.858 | 16.644 | 67.676 | 1.00 | 0.00 | ATOM | 2492 | C | LYS | 304 | 18.824 | 24.907 | 73.324 | 1.00 | 18.42 |
| ATOM | 2421 | CA | LEU | 299 | 23.831 | 17.556 | 69.599 | 1.00 | 7.71 | ATOM | 2493 | O | LYS | 304 | 18.238 | 25.961 | 73.549 | 1.00 | 22.41 |
| ATOM | 2422 | CB | LEU | 299 | 25.353 | 17.473 | 69.593 | 1.00 | 3.79 | ATOM | 2494 | N | ARG | 305 | 18.639 | 23.822 | 74.048 | 1.00 | 16.95 |
| ATOM | 2495 | H | ARG | 305 | 19.098 | 22.988 | 73.807 | 1.00 | 0.00 | ATOM | 2567 | CA | GLY | 311 | 24.602 | 20.545 | 80.033 | 1.00 | 8.82 |
| ATOM | 2496 | CA | ARG | 305 | 17.757 | 23.842 | 75.188 | 1.00 | 19.62 | ATOM | 2568 | O | GLY | 311 | 24.465 | 19.471 | 79.423 | 1.00 | 9.64 |
| ATOM | 2497 | CB | ARG | 305 | 16.964 | 22.546 | 75.230 | 1.00 | 21.07 | ATOM | 2569 | N | ALA | 312 | 25.191 | 21.615 | 79.522 | 1.00 | 8.08 |
| ATOM | 2498 | CG | ARG | 305 | 16.172 | 22.311 | 73.957 | 1.00 | 25.07 | ATOM | 2570 | H | ALA | 312 | 25.250 | 22.428 | 80.063 | 1.00 | 0.00 |
| ATOM | 2499 | CD | ARG | 305 | 15.393 | 21.039 | 74.043 | 1.00 | 26.97 | ATOM | 2571 | CA | ALA | 312 | 25.769 | 21.630 | 78.189 | 1.00 | 8.48 |
| ATOM | 2500 | NE | ARG | 305 | 14.736 | 20.740 | 72.777 | 1.00 | 31.36 | ATOM | 2572 | CB | ALA | 312 | 26.292 | 23.023 | 77.873 | 1.00 | 8.53 |
| ATOM | 2501 | HE | ARG | 305 | 14.150 | 21.425 | 72.388 | 1.00 | 0.00 | ATOM | 2573 | C | ALA | 312 | 26.895 | 20.598 | 78.093 | 1.00 | 9.64 |
| ATOM | 2502 | CZ | ARG | 305 | 14.889 | 19.604 | 72.109 | 1.00 | 32.19 | ATOM | 2574 | O | ALA | 312 | 26.918 | 19.772 | 77.172 | 1.00 | 9.55 |
| ATOM | 2503 | NH1 | ARG | 305 | 15.691 | 18.651 | 72.579 | 1.00 | 34.71 | ATOM | 2575 | N | LYS | 313 | 27.817 | 20.623 | 79.050 | 1.00 | 5.87 |
| ATOM | 2504 | HH11 | ARG | 305 | 16.176 | 18.789 | 73.443 | 1.00 | 0.00 | ATOM | 2576 | H | LYS | 313 | 27.749 | 21.278 | 79.766 | 1.00 | 0.00 |
| ATOM | 2505 | HH12 | ARG | 305 | 15.793 | 17.791 | 72.082 | 1.00 | 0.00 | ATOM | 2577 | CA | LYS | 313 | 28.919 | 19.672 | 79.049 | 1.00 | 6.70 |
| ATOM | 2506 | NH2 | ARG | 305 | 14.199 | 19.400 | 70.993 | 1.00 | 32.82 | ATOM | 2578 | CB | LYS | 313 | 29.931 | 20.006 | 80.169 | 1.00 | 7.83 |
| ATOM | 2507 | HH21 | ARG | 305 | 13.576 | 20.106 | 70.656 | 1.00 | 0.00 | ATOM | 2579 | CG | LYS | 313 | 31.208 | 19.156 | 80.129 | 1.00 | 8.27 |
| ATOM | 2508 | HH22 | ARG | 305 | 14.306 | 18.543 | 70.489 | 1.00 | 0.00 | ATOM | 2580 | CD | LYS | 313 | 32.274 | 19.689 | 81.073 | 1.00 | 6.98 |
| ATOM | 2509 | C | ARG | 305 | 18.505 | 24.039 | 76.499 | 1.00 | 21.81 | ATOM | 2581 | CE | LYS | 313 | 31.776 | 19.685 | 82.508 | 1.00 | 9.13 |
| ATOM | 2510 | O | ARG | 305 | 17.892 | 24.305 | 77.530 | 1.00 | 24.20 | ATOM | 2582 | NZ | LYS | 313 | 31.522 | 18.308 | 83.035 | 1.00 | 10.81 |
| ATOM | 2511 | N | GLU | 306 | 19.828 | 23.922 | 76.470 | 1.00 | 18.02 | ATOM | 2583 | HZ1 | LYS | 313 | 32.413 | 17.764 | 83.005 | 1.00 | 0.00 |
| ATOM | 2512 | H | GLU | 306 | 20.281 | 23.767 | 75.617 | 1.00 | 0.00 | ATOM | 2584 | HZ2 | LYS | 313 | 30.815 | 17.835 | 82.440 | 1.00 | 0.00 |
| ATOM | 2513 | CA | GLU | 306 | 20.615 | 24.068 | 77.691 | 1.00 | 11.09 | ATOM | 2585 | HZ3 | LYS | 313 | 31.184 | 18.363 | 84.013 | 1.00 | 0.00 |
| ATOM | 2514 | CB | GLU | 306 | 21.958 | 23.344 | 77.541 | 1.00 | 9.94 | ATOM | 2586 | C | LYS | 313 | 28.413 | 18.225 | 79.184 | 1.00 | 9.48 |
| ATOM | 2515 | CG | GLU | 306 | 21.874 | 21.910 | 77.107 | 1.00 | 6.81 | ATOM | 2587 | O | LYS | 313 | 28.935 | 17.322 | 78.542 | 1.00 | 10.99 |
| ATOM | 2516 | CD | GLU | 306 | 21.317 | 21.009 | 78.175 | 1.00 | 14.41 | ATOM | 2588 | N | GLU | 314 | 27.354 | 18.016 | 79.958 | 1.00 | 9.89 |
| ATOM | 2517 | OE1 | GLU | 306 | 21.414 | 21.345 | 79.370 | 1.00 | 16.53 | ATOM | 2589 | H | GLU | 314 | 26.926 | 18.774 | 80.402 | 1.00 | 0.00 |
| ATOM | 2518 | OE2 | GLU | 306 | 20.761 | 19.955 | 77.827 | 1.00 | 22.60 | ATOM | 2590 | CA | GLU | 314 | 26.828 | 16.674 | 80.165 | 1.00 | 9.87 |
| ATOM | 2519 | C | GLU | 306 | 20.917 | 25.517 | 77.969 | 1.00 | 10.43 | ATOM | 2591 | CB | GLU | 314 | 25.869 | 16.642 | 81.371 | 1.00 | 10.30 |
| ATOM | 2520 | O | GLU | 306 | 21.054 | 26.301 | 77.044 | 1.00 | 8.17 | ATOM | 2592 | CG | GLU | 314 | 25.387 | 15.239 | 81.785 | 1.00 | 13.21 |
| ATOM | 2521 | N | ILE | 307 | 21.023 | 25.874 | 79.244 | 1.00 | 12.01 | ATOM | 2593 | CD | GLU | 314 | 26.454 | 14.374 | 82.499 | 1.00 | 17.97 |
| ATOM | 2522 | H | ILE | 307 | 20.833 | 25.217 | 79.940 | 1.00 | 0.00 | ATOM | 2594 | OE1 | GLU | 314 | 27.470 | 14.909 | 42.994 | 1.00 | 21.28 |
| ATOM | 2523 | CA | ILE | 307 | 21.403 | 27.237 | 79.616 | 1.00 | 12.96 | ATOM | 2595 | OE2 | GLU | 314 | 26.258 | 13.147 | 82.593 | 1.00 | 13.39 |
| ATOM | 2524 | CB | ILE | 307 | 20.236 | 28.095 | 80.236 | 1.00 | 12.97 | ATOM | 2596 | C | GLU | 314 | 26.199 | 16.027 | 78.928 | 1.00 | 10.09 |
| ATOM | 2525 | CG2 | ILE | 307 | 19.125 | 28.303 | 79.199 | 1.00 | 15.84 | ATOM | 2597 | O | GLU | 314 | 26.416 | 14.838 | 78.695 | 1.00 | 10.37 |
| ATOM | 2526 | CG1 | ILE | 307 | 19.679 | 27.440 | 51.509 | 1.00 | 11.68 | ATOM | 2598 | N | ILE | 315 | 25.389 | 16.741 | 78.149 | 1.00 | 12.08 |
| ATOM | 2527 | CD1 | ILE | 307 | 18.792 | 28.362 | 82.351 | 1.00 | 8.49 | ATOM | 2599 | H | ILE | 315 | 25.170 | 17.673 | 78.379 | 1.00 | 0.00 |
| ATOM | 2528 | C | ILE | 307 | 22.576 | 27.199 | 80.591 | 1.00 | 11.34 | ATOM | 2600 | CA | ILE | 315 | 24.832 | 16.088 | 76.954 | 1.00 | 11.34 |
| ATOM | 2529 | O | ILE | 307 | 23.133 | 28.239 | 80.920 | 1.00 | 13.88 | ATOM | 2601 | CB | ILE | 315 | 23.705 | 16.862 | 76.258 | 1.00 | 16.41 |
| ATOM | 2530 | N | THR | 308 | 22.968 | 26.013 | 81.053 | 1.00 | 9.66 | ATOM | 2602 | CG2 | ILE | 315 | 22.353 | 16.420 | 76.770 | 1.00 | 22.26 |
| ATOM | 2531 | H | THR | 308 | 22.518 | 25.209 | 80.757 | 1.00 | 0.00 | ATOM | 2603 | CG1 | ILE | 315 | 23.976 | 18.353 | 76.322 | 1.00 | 3.15 |
| ATOM | 2532 | CA | THR | 308 | 24.082 | 25.925 | 81.998 | 1.00 | 9.42 | ATOM | 2604 | CD1 | ILE | 315 | 23.084 | 19.134 | 75.442 | 1.00 | 21.44 |
| ATOM | 2533 | CB | THR | 308 | 23.683 | 25.241 | 83.373 | 1.00 | 10.90 | ATOM | 2605 | C | ILE | 315 | 25.913 | 15.886 | 75.911 | 1.00 | 5.97 |
| ATOM | 2534 | OG1 | THR | 308 | 23.318 | 23.864 | 83.160 | 1.00 | 17.40 | ATOM | 2606 | O | ILE | 315 | 25.863 | 14.936 | 75.143 | 1.00 | 9.76 |

-continued

| | | | | | | | | | | |
|---|---|---|---|---|---|---|---|---|---|---|
|ATOM|2535|HG1|THR|308|22.532|23.846|82.591|1.00|0.00| |
|ATOM|2536|CG2|THR|308|22.530|26.007|84.095|1.00|9.88| |
|ATOM|2537|C|THR|308|25.291|25.186|81.431|1.00|7.68| |
|ATOM|2538|O|THR|308|25.154|24.314|80.573|1.00|12.31| |
|ATOM|2539|N|PHE|309|26.463|25.534|81.954|1.00|7.15| |
|ATOM|2540|H|PHE|309|36.474|26.251|82.627|1.00|0.00| |
|ATOM|2541|CA|PHE|309|27.741|24.941|81.583|1.00|10.36| |
|ATOM|2542|CB|PHE|309|28.853|25.564|82.435|1.00|4.51| |
|ATOM|2543|CG|PHE|309|30.163|24.838|82.339|1.00|7.97| |
|ATOM|2544|CD1|PHE|309|31.010|25.052|81.246|1.00|9.69| |
|ATOM|2545|CD2|PHE|309|30.538|23.911|83.319|1.00|7.03| |
|ATOM|2546|CE1|PHE|309|21.193|24.345|81.109|1.00|6.61| |
|ATOM|2547|CE2|PHE|309|31.728|23.189|83.196|1.00|6.73| |
|ATOM|2548|CZ|PHE|309|32.561|23.411|82.086|1.00|7.86| |
|ATOM|2549|C|PHE|309|27.719|23.444|81.823|1.00|11.68| |
|ATOM|2550|O|PHE|309|28.121|22.656|80.968|1.00|13.44| |
|ATOM|2551|N|HIS|310|27.261|23.053|83.006|1.00|13.27| |
|ATOM|2552|H|HIS|310|26.947|23.720|83.648|1.00|0.00| |
|ATOM|2553|CA|HIS|310|27.217|21.655|83.351|1.00|11.98| |
|ATOM|2554|CB|HIS|310|26.860|21.462|84.815|1.00|15.73| |
|ATOM|2555|CG|HIS|310|26.676|20.034|85.184|1.00|11.24| |
|ATOM|2556|CD2|HIS|310|27.599|19.060|85.464|1.00|9.87| |
|ATOM|2557|ND1|HIS|310|25.470|19.400|85.146|1.00|16.13| |
|ATOM|2558|HD1|HIS|310|24.598|19.834|84.991|1.00|0.00| |
|ATOM|2559|CE1|HIS|310|25.616|18.113|85.362|1.00|15.93| |
|ATOM|2560|NE2|HIS|310|26.914|17.885|85.558|1.00|16.87| |
|ATOM|2561|HE2|HIS|310|27.314|17.005|85.735|1.00|0.00| |
|ATOM|2562|C|HIS|310|26.248|20.860|82.481|1.00|12.95| |
|ATOM|2563|O|HIS|310|26.558|19.734|82.077|1.00|12.90| |
|ATOM|2564|N|GLY|311|25.060|21.414|52.258|1.00|10.96| |
|ATOM|2565|H|GLY|311|24.844|22.285|82.645|1.00|0.00| |
|ATOM|2566|CA|GLY|311|24.073|20.734|81.438|1.00|11.14| |
|ATOM|2639|CD2|TYR|319|26.261|13.497|69.551|1.00|10.75| |
|ATOM|2640|CE2|TYR|319|24.877|13.527|69.411|1.00|8.24| |
|ATOM|2641|CZ|TYR|319|24.090|13.918|70.489|1.00|10.13| |
|ATOM|2642|OH|TYR|319|22.712|13.926|70.364|1.00|12.82| |
|ATOM|2643|HH|TYR|319|22.469|13.627|69.495|1.00|0.00| |
|ATOM|2644|C|TYR|319|30.303|12.183|71.337|1.00|16.52| |
|ATOM|2645|O|TYR|319|31.097|12.447|72.244|1.00|16.79| |
|ATOM|2646|N|SER|320|30.687|11.661|70.172|1.00|13.62| |
|ATOM|2647|H|SER|320|30.000|11.455|69.505|1.00|0.00| |
|ATOM|2648|CA|SER|320|32.087|11.391|69.892|1.00|14.04| |
|ATOM|2649|CB|SER|320|32.220|10.526|68.638|1.00|18.38| |
|ATOM|2650|OG|SER|320|31.901|11.267|67.471|1.00|21.74| |
|ATOM|2651|HG|SER|320|30.999|11.575|67.521|1.00|0.00| |
|ATOM|2652|C|SER|320|32.838|12.680|69.670|1.00|13.69| |
|ATOM|2653|O|SER|320|32.246|13.688|69.321|1.00|17.20| |
|ATOM|2654|N|ALA|321|34.159|12.615|69.781|1.00|14.55| |
|ATOM|2655|H|ALA|321|34.567|11.579|70.020|1.00|0.00| |
|ATOM|2656|CA|ALA|321|35.029|13.771|69.580|1.00|14.54| |
|ATOM|2657|CB|ALA|321|36.489|13.352|69.735|1.00|17.29| |
|ATOM|2658|C|ALA|321|34.821|14.383|68.200|1.00|12.07| |
|ATOM|2659|O|ALA|321|35.033|15.582|67.998|1.00|13.71| |
|ATOM|2660|N|GLY|322|34.454|13.538|67.248|1.00|13.47| |
|ATOM|2661|H|GLY|322|34.317|12.593|67.463|1.00|0.00| |
|ATOM|2662|CA|GLY|322|34.237|13.993|65.887|1.00|15.49| |
|ATOM|2663|C|GLY|322|32.976|14.818|65.732|1.00|14.78| |
|ATOM|2664|O|GLY|322|32.968|15.810|64.991|1.00|16.40| |
|ATOM|2665|N|ALA|323|31.881|14.342|66.327|1.00|11.91| |
|ATOM|2666|H|ALA|323|31.946|13.536|66.881|1.00|0.00| |
|ATOM|2667|CA|ALA|323|30.608|15.041|66.250|1.00|11.53| |
|ATOM|2668|CB|ALA|323|29.495|14.171|66.754|1.00|5.28| |
|ATOM|2669|C|ALA|323|30.692|16.319|67.057|1.00|12.61| |
|ATOM|2670|O|ALA|323|30.058|17.326|66.720|1.00|13.81| |
|ATOM|2671|N|LEU|324|31.515|16.279|68.100|1.00|9.94| |
|ATOM|2672|H|LEU|324|31.994|14.452|68.301|1.00|0.00| |
|ATOM|2673|CA|LEU|324|31.720|17.421|68.973|1.00|8.79| |
|ATOM|2674|CB|LEU|324|32.497|16.994|70.218|1.00|13.93| |
|ATOM|2675|CG|LEU|324|31.761|16.143|71.253|1.00|14.65| |
|ATOM|2676|CD1|LEU|324|32.776|15.501|72.188|1.00|21.09| |
|ATOM|2677|CD2|LEU|324|30.761|16.980|72.023|1.00|13.81| |
|ATOM|2678| |LEU|324|32.462|18.555|68.262|1.00|10.41| |
|ATOM|2679|O|LEU|324|32.078|19.723|68.371|1.00|11.89| |
|ATOM|2680|N|ALA|325|33.515|18.215|67.525|1.00|10.43| |
|ATOM|2681|H|ALA|325|33.783|17.276|67.480|1.00|0.00| |
|ATOM|2682|CA|ALA|325|34.296|19.221|66.802|1.00|8.57| |
|ATOM|2683|CB|ALA|325|35.519|18.587|66.160|1.00|10.40| |
|ATOM|2684|C|ALA|325|33.430|19.877|65.746|1.00|4.56| |
|ATOM|2685|O|ALA|325|33.418|21.088|65.618|1.00|11.53| |
|ATOM|2607|N|SER|316|26.893|16.779|75.886|1.00|7.34| |
|ATOM|2608|H|SER|316|26.880|17.534|76.517|1.00|0.00| |
|ATOM|2609|CA|SER|316|27.990|16.696|74.926|1.00|6.45| |
|ATOM|2610|CB|SER|316|28.904|17.911|75.066|1.00|6.72| |
|ATOM|2611|OG|SER|316|28.229|19.094|74.683|1.00|8.15| |
|ATOM|2612|HG|SER|316|28.813|19.846|74.799|1.00|0.00| |
|ATOM|2613|C|SER|316|28.794|15.412|75.118|1.00|12.37| |
|ATOM|2614|O|SER|316|29.350|14.863|74.165|1.00|11.95| |
|ATOM|2615|N|LEU|317|28.826|14.921|76.356|1.00|13.97| |
|ATOM|2616|H|LEU|317|28.344|15.396|77.071|1.00|0.00| |
|ATOM|2617|CA|LEU|317|29.552|13.705|76.694|1.00|11.99| |
|ATOM|2618|CB|LEU|317|29.611|13.538|78.216|1.00|12.81| |
|ATOM|2619|CG|LEU|317|30.431|14.580|79.001|1.00|17.31| |
|ATOM|2620|CD1|LEU|317|30.330|14.316|80.504|1.00|15.91| |
|ATOM|2621|CD2|LEU|317|31.899|14.563|78.550|1.00|17.80| |
|ATOM|2622|C|LEU|317|28.960|12.457|76.029|1.00|15.63| |
|ATOM|2623|O|LEU|317|29.594|11.394|76.005|1.00|16.20| |
|ATOM|2624|N|SER|318|27.739|12.562|75.506|1.00|15.11| |
|ATOM|2625|H|SER|318|27.236|13.398|75.579|1.00|0.00| |
|ATOM|2626|CA|SER|318|27.137|11.419|74.826|1.00|11.86| |
|ATOM|2627|CB|SER|318|25.613|11.385|75.008|1.00|15.54| |
|ATOM|2628|OG|SER|318|24.998|12.546|74.482|1.00|22.77| |
|ATOM|2629|HG|SER|318|25.307|13.306|74.918|1.00|0.00| |
|ATOM|2630|C|SER|318|27.505|11.405|73.339|1.00|15.03| |
|ATOM|2631|O|SER|318|27.091|10.509|72.606|1.00|17.55| |
|ATOM|2632|N|TYR|319|28.389|12.313|72.926|1.00|14.09| |
|ATOM|2633|H|TYR|319|28.766|12.947|73.568|1.00|0.00| |
|ATOM|2634|CA|TYR|319|28.806|12.403|71.525|1.00|12.76| |
|ATOM|2635|CB|TYR|319|28.375|13.755|70.930|1.00|10.14| |
|ATOM|2636|CG|TYR|319|26.875|13.856|70.761|1.00|12.67| |
|ATOM|2637|CD1|TYR|319|26.060|14.251|71.824|1.00|6.01| |
|ATOM|2638|CE1|TYR|319|24.677|14.283|71.697|1.00|7.18| |
|ATOM|2711|H|GLY|329|32.095|22.695|65.112|1.00|0.00| |
|ATOM|2712|CA|GLY|329|32.109|24.286|63.733|1.00|10.69| |
|ATOM|2713|C|GLY|329|30.796|24.936|63.316|1.00|10.39| |
|ATOM|2714|O|GLY|329|30.808|26.032|62.776|1.00|12.00| |
|ATOM|2715|N|LEU|330|29.669|24.278|63.570|1.00|4.79| |
|ATOM|2716|H|LEU|330|29.719|23.386|63.968|1.00|0.00| |
|ATOM|2717|CA|LEU|330|28.367|24.841|63.253|1.00|8.84| |
|ATOM|2718|CB|LEU|330|27.246|23.969|63.812|1.00|6.31| |
|ATOM|2719|CG|LEU|330|26.997|22.592|63.224|1.00|10.14| |
|ATOM|2720|CD1|LEU|330|25.850|21.945|63.971|1.00|11.07| |
|ATOM|2721|CD2|LEU|330|26.662|22.706|61.744|1.00|14.61| |
|ATOM|2722|C|LEU|330|28.257|26.208|63.905|1.00|8.14| |
|ATOM|2723|O|LEU|330|27.894|27.190|63.266|1.00|14.59| |
|ATOM|2724|N|ILE|331|28.569|26.258|65.190|1.00|10.75| |
|ATOM|2725|H|ILE|331|28.831|25.426|65.637|1.00|0.00| |
|ATOM|2726|CA|ILE|331|28.518|29.491|65.973|1.00|8.61| |
|ATOM|2727|CB|ILE|331|28.724|27.154|67.486|1.00|14.63| |
|ATOM|2728|CG2|ILE|331|28.877|28.412|68.303|1.00|15.69| |
|ATOM|2729|CG1|ILE|331|27.514|26.371|68.020|1.00|11.64| |
|ATOM|2730|CD1|ILE|331|27.776|25.653|69.307|1.00|13.02| |
|ATOM|2731|C|ILE|331|29.512|28.555|65.472|1.00|9.88| |
|ATOM|2732|O|ILE|331|29.152|29.714|65.260|1.00|9.23| |
|ATOM|2733|N|TYR|332|30.741|28.150|65.183|1.00|8.51| |
|ATOM|2734|H|TYR|332|30.985|27.208|65.317|1.00|0.00| |
|ATOM|2735|CA|TYR|332|31.742|29.089|64.696|1.00|9.89| |
|ATOM|2736|CB|TYR|332|33.102|28.404|64.633|1.00|7.30| |
|ATOM|2737|CG|TYR|332|34.244|29.357|64.406|1.00|10.37| |
|ATOM|2738|CD1|TYR|332|34.724|30.164|65.439|1.00|9.94| |
|ATOM|2739|CE1|TYR|332|35.792|30.038|65.229|1.00|7.63| |
|ATOM|2740|CD2|TYR|332|34.858|29.447|63.155|1.00|11.58| |
|ATOM|2741|CE2|TYR|332|35.921|30.311|62.934|1.00|14.42| |
|ATOM|2742|CZ|TYR|332|36.385|13.103|63.972|1.00|13.17| |
|ATOM|2743|OH|TYR|332|37.445|31.938|63.710|1.00|13.95| |
|ATOM|2744|HH|TYR|332|37.652|32.429|64.514|1.00|0.00| |
|ATOM|2745|C|TYR|332|31.383|29.638|63.318|1.00|11.07| |
|ATOM|2746|O|TYR|332|31.773|30.746|62.966|1.00|11.27| |
|ATOM|2747|N|ASN|333|30.643|28.849|62.538|1.00|12.83| |
|ATOM|2748|H|ASN|333|30.374|27.972|62.880|1.00|0.00| |
|ATOM|2749|CA|ASN|333|30.241|29.232|61.184|1.00|10.24| |
|ATOM|2750|CB|ASN|333|30.038|27.987|60.338|1.00|4.03| |
|ATOM|2751|CG|ASN|333|31.323|27.336|59.965|1.00|9.06| |
|ATOM|2752|OD1|ASN|333|32.375|27.954|60.020|1.00|9.53| |
|ATOM|2753|ND2|ASN|333|31.262|26.074|59.605|1.00|9.96| |
|ATOM|2754|HD21|ASN|333|30.405|25.605|59.610|1.00|0.00| |
|ATOM|2755|HD22|ASN|333|32.111|25.625|59.373|1.00|0.00| |
|ATOM|2756|C|ASN|333|28.960|30.041|61.163|1.00|14.77| |
|ATOM|2757|O|ASN|333|28.474|30.406|60.088|1.00|14.34| |

-continued

| | | | | | | | | | |
|---|---|---|---|---|---|---|---|---|---|
|ATOM|2686|N SER 326|32.662|19.080|65.016|1.00|8.36|||
|ATOM|2687|H SER 326|32.685|18.114|65.163|1.00|0.00|||
|ATOM|2688|CA SER 326|31.800|19.638|63.987|1.00|10.75|||
|ATOM|2689|CB SER 326|31.294|18.537|63.064|1.00|6.06|||
|ATOM|2690|OG SER 326|32.399|17.399|62.357|1.00|13.88|||
|ATOM|2691|HG SER 326|33.012|17.638|62.982|1.00|0.00|||
|ATOM|2692|C SER 326|30.667|20.478|64.591|1.00|12.64|||
|ATOM|2693|O SER 326|30.231|21.464|63.992|1.00|11.71|||
|ATOM|2694|N CYS 327|30.205|20.118|65.788|1.00|12.50|||
|ATOM|2695|H CYS 327|30.543|19.307|66.224|1.00|0.00|||
|ATOM|2696|CA CYS 327|29.173|20.922|66.443|1.00|9.23|||
|ATOM|2697|CB CYS 327|28.634|20.233|67.695|1.00|4.17|||
|ATOM|2698|SG CYS 327|27.219|21.118|68.396|1.00|11.27|||
|ATOM|2699|C CYS 327|29.791|22.298|66.783|1.00|8.75|||
|ATOM|2700|O CYS 327|29.138|23.326|66.688|1.00|9.40|||
|ATOM|2701|N MET 328|31.066|22.316|67.153|1.00|6.97|||
|ATOM|2702|H MET 328|31.558|21.471|67.239|1.00|0.00|||
|ATOM|2703|CA MET 328|31.742|23.567|67.443|1.00|5.18|||
|ATOM|2704|CB MET 328|33.145|23.305|67.996|1.00|4.83|||
|ATOM|2705|CG MET 328|33.175|22.929|69.500|1.00|7.46|||
|ATOM|2706|SD MET 328|34.824|22.610|70.205|1.00|10.23|||
|ATOM|2707|CE MET 328|35.534|24.168|70.112|1.00|2.00|||
|ATOM|2708|C MET 328|31.838|24.373|66.159|1.00|7.71|||
|ATOM|2709|O MET 328|31.787|25.596|66.184|1.00|7.55|||
|ATOM|2710|N GLY 329|32.015|23.668|65.045|1.00|11.52|||
|ATOM|2783|O MET 335|22.914|27.375|62.243|1.00|21.65|||
|ATOM|2784|N GLY 336|24.535|27.800|63.727|1.00|17.39|||
|ATOM|2785|H GLY 336|25.486|28.002|63.847|1.00|0.00|||
|ATOM|2786|CA GLY 336|23.728|27.561|64.906|1.00|16.17|||
|ATOM|2787|C GLY 336|24.244|28.549|65.937|1.00|17.50|||
|ATOM|2788|O GLY 336|25.339|29.101|65.758|1.00|17.86|||
|ATOM|2789|N ALA 337|23.471|28.816|66.987|1.00|15.42|||
|ATOM|2790|H ALA 337|22.613|28.390|67.070|1.00|0.00|||
|ATOM|2791|CA ALA 337|23.896|29.751|68.025|1.00|13.47|||
|ATOM|2792|CB ALA 337|23.237|31.104|67.855|1.00|16.73|||
|ATOM|2793|C ALA 337|23.577|29.195|69.389|1.00|14.36|||
|ATOM|2794|O ALA 337|22.557|28.547|69.578|1.00|17.81|||
|ATOM|2795|N VAL 338|24.410|29.539|70.361|1.00|14.94|||
|ATOM|2796|H VAL 338|25.141|30.163|70.181|1.00|0.00|||
|ATOM|2797|CA VAL 338|24.262|29.037|71.723|1.00|16.42|||
|ATOM|2798|CB VAL 338|25.041|27.691|71.770|1.00|16.57|||
|ATOM|2799|CG1 VAL 338|26.444|27.873|72.284|1.00|15.56|||
|ATOM|2800|CG2 VAL 338|24.273|26.643|72.459|1.00|23.51|||
|ATOM|2801|C VAL 338|24.845|30.105|72.962|1.00|17.49|||
|ATOM|2802|O VAL 338|25.582|30.994|72.236|1.00|16.55|||
|ATOM|2803|N THR 339|24.494|30.060|73.986|1.00|17.19|||
|ATOM|2804|H THR 339|23.867|29.360|74.300|1.00|0.00|||
|ATOM|2805|CA THR 339|25.030|31.037|74.962|1.00|16.56|||
|ATOM|2806|CB THR 339|24.249|31.079|76.321|1.00|14.23|||
|ATOM|2807|OG1 THR 339|24.423|29.853|77.040|1.00|17.38|||
|ATOM|2808|HG1 THR 339|25.328|29.719|77.234|1.00|0.00|||
|ATOM|2809|CG2 THR 339|22.763|31.303|76.083|1.00|19.66|||
|ATOM|2810|C THR 339|26.480|30.704|75.255|1.00|12.10|||
|ATOM|2811|O THR 339|26.881|29.559|75.149|1.00|13.55|||
|ATOM|2812|N THR 340|27.251|31.695|75.658|1.00|11.94|||
|ATOM|2813|H THR 340|26.864|32.596|75.770|1.00|0.00|||
|ATOM|2814|CA THR 340|28.665|31.495|75.946|1.00|15.32|||
|ATOM|2815|CB THR 340|29.319|32.822|76.381|1.00|19.16|||
|ATOM|2816|OG1 THR 340|29.006|33.827|75.415|1.00|20.58|||
|ATOM|2817|HG1 THR 340|29.371|33.550|74.578|1.00|0.00|||
|ATOM|2818|CG2 THR 340|30.827|32.684|76.466|1.00|19.52|||
|ATOM|2819|C THR 340|28.948|30.399|76.972|1.00|12.71|||
|ATOM|2820|O THR 340|29.887|29.632|76.807|1.00|12.19|||
|ATOM|2821|N GLU 341|28.100|30.295|77.990|1.00|10.08|||
|ATOM|2822|H GLU 341|27.344|30.917|78.031|1.00|0.00|||
|ATOM|2823|CA GLU 341|28.243|29.283|79.043|1.00|13.73|||
|ATOM|2824|CB GLU 341|27.184|29.525|80.149|1.00|18.89|||
|ATOM|2825|CG GLU 341|27.208|30.952|80.818|1.00|35.09|||
|ATOM|2826|CD GLU 341|26.251|32.032|80.178|1.00|38.66|||
|ATOM|2827|OE1 GLU 341|25.190|32.386|80.797|1.00|31.21|||
|ATOM|2828|OE2 GLU 341|36.596|32.565|79.087|1.00|31.75|||
|ATOM|2829|C GLU 341|28.085|27.856|78.463|1.00|13.64|||
|ATOM|2830|O GLU 341|28.824|26.921|78.807|1.00|11.29|||
|ATOM|2831|N VAL 342|27.068|27.694|77.625|1.00|12.75|||
|ATOM|2832|H VAL 342|26.480|28.445|77.448|1.00|0.00|||
|ATOM|2833|CA VAL 342|26.784|26.431|76.959|1.00|9.60|||
|ATOM|2834|CB VAL 342|25.456|26.534|76.154|1.00|9.98|||
|ATOM|2835|CG1 VAL 342|25.147|25.230|75.462|1.00|9.26|||
|ATOM|2836|CG2 VAL 342|24.316|26.930|77.061|1.00|9.74|||
|ATOM|2758|N ARG 334|28.379|30.251|62.347|1.00|15.99|||
|ATOM|2759|H ARG 334|28.811|29.886|63.152|1.00|0.00|||
|ATOM|2760|CA ARG 334|27.132|31.006|62.527|1.00|14.30|||
|ATOM|2761|CB ARG 334|27.201|32.385|61.860|1.00|12.13|||
|ATOM|2762|CG ARG 334|28.467|33.159|62.160|1.00|12.54|||
|ATOM|2763|CD ARG 334|28.415|35.548|61.550|1.00|14.86|||
|ATOM|2764|NE ARG 334|29.745|35.121|61.408|1.00|13.78|||
|ATOM|2765|HE ARG 334|30.288|34.824|60.652|1.00|0.00|||
|ATOM|2766|CZ ARG 334|30.276|36.016|62.232|1.00|18.36|||
|ATOM|2767|NH1 ARG 334|29.596|36.451|63.275|1.00|22.12|||
|ATOM|2768|HH11 ARG 334|28.674|36.108|63.453|1.00|0.00|||
|ATOM|2769|HH12 ARG 334|30.001|37.126|63.894|1.00|0.00|||
|ATOM|2770|NH2 ARG 334|31.478|36.511|61.983|1.00|17.96|||
|ATOM|2771|HH21 ARG 334|31.988|36.217|61.178|1.00|0.00|||
|ATOM|2772|HH22 ARG 334|31.876|37.188|62.607|1.00|0.00|||
|ATOM|2773|C ARG 334|25.940|30.245|61.991|1.00|15.31|||
|ATOM|2774|O ARG 334|24.923|30.840|61.653|1.00|18.76|||
|ATOM|2775|N MET 335|26.083|28.928|61.884|1.00|15.35|||
|ATOM|2776|H MET 335|26.933|28.524|62.148|1.00|0.00|||
|ATOM|2777|CA MET 335|25.020|28.066|61.382|1.00|15.46|||
|ATOM|2778|CB MET 335|25.613|26.792|60.817|1.00|13.01|||
|ATOM|2779|CG MET 335|26.576|27.059|59.698|1.00|17.95|||
|ATOM|2780|SD MET 335|27.318|25.562|59.112|1.00|33.34|||
|ATOM|2781|CE MET 335|25.814|24.584|58.716|1.00|30.01|||
|ATOM|2782|C MET 335|24.046|27.736|62.497|1.00|16.27|||
|ATOM|2855|C PHE 344|31.895|25.092|77.548|1.00|10.59|||
|ATOM|2856|O PHE 344|32.887|24.363|77.560|1.00|14.02|||
|ATOM|2857|N GLY 345|30.676|24.663|77.880|1.00|9.18|||
|ATOM|2858|H GLY 345|29.932|25.305|77.905|1.00|0.00|||
|ATOM|2859|CA GLY 345|30.431|23.265|78.193|1.00|7.24|||
|ATOM|2860|C GLY 345|30.816|22.355|77.028|1.00|10.74|||
|ATOM|2861|O GLY 345|31.500|21.346|77.232|1.00|8.67|||
|ATOM|2862|N LEU 346|30.369|22.693|75.813|1.00|11.73|||
|ATOM|2863|H LEU 346|29.793|23.487|75.736|1.00|0.00|||
|ATOM|2864|CA LEU 346|30.703|21.925|74.593|1.00|8.91|||
|ATOM|2865|CB LEU 346|30.090|22.594|73.341|1.00|7.42|||
|ATOM|2866|CG LEU 346|30.508|22.120|71.930|1.00|6.63|||
|ATOM|2867|CD1 LEU 346|30.113|20.665|71.722|1.00|2.85|||
|ATOM|2868|CD2 LEU 346|29.846|22.974|70.851|1.00|5.26|||
|ATOM|2869|C LEU 346|32.223|21.831|74.402|1.00|6.21|||
|ATOM|2870|O LEU 346|32.743|20.760|74.134|1.00|7.04|||
|ATOM|2871|N VAL 347|32.908|22.967|74.518|1.00|6.57|||
|ATOM|2872|H VAL 347|32.407|23.793|74.703|1.00|0.00|||
|ATOM|2873|CA VAL 347|34.363|23.056|74.368|1.00|7.97|||
|ATOM|2874|CB VAL 347|34.862|24.498|74.642|1.00|11.21|||
|ATOM|2875|CG1 VAL 347|36.381|24.512|74.879|1.00|13.97|||
|ATOM|2876|CG2 VAL 347|34.495|25.437|73.495|1.00|7.51|||
|ATOM|2877|C VAL 347|35.073|22.120|75.341|1.00|10.24|||
|ATOM|2878|O VAL 337|36.029|21.433|74.973|1.00|9.62|||
|ATOM|2879|N CYS 348|34.586|22.079|76.582|1.00|11.21|||
|ATOM|2880|H CYS 348|33.810|22.636|76.811|1.00|0.00|||
|ATOM|2881|CA CYS 348|35.187|21.241|77.620|1.00|8.37|||
|ATOM|2882|CB CYS 348|34.715|21.692|78.994|1.00|8.63|||
|ATOM|2883|SG CYS 348|35.450|23.266|79.481|1.00|16.28|||
|ATOM|2884|C CYS 348|34.957|19.759|77.427|1.00|7.38|||
|ATOM|2885|O CYS 348|35.823|18.936|77.746|1.00|9.09|||
|ATOM|2886|N ALA 349|33.791|19.399|76.908|1.00|8.67|||
|ATOM|2887|H ALA 349|33.109|20.076|76.695|1.00|0.00|||
|ATOM|2888|CA ALA 349|33.535|17.994|76.652|1.00|7.20|||
|ATOM|2889|CB ALA 349|32.081|17.777|76.294|1.00|6.86|||
|ATOM|2890|C ALA 349|34.448|17.557|75.508|1.00|8.04|||
|ATOM|2891|O ALA 349|35.072|16.504|75.594|1.00|12.59|||
|ATOM|2892|N THR 350|34.572|18.387|74.463|1.00|13.57|||
|ATOM|2893|H THR 350|34.084|19.240|74.461|1.00|0.00|||
|ATOM|2894|CA THR 350|35.423|18.056|73.309|1.00|12.48|||
|ATOM|2895|CB THR 350|35.302|19.079|72.119|1.00|11.62|||
|ATOM|2896|OG1 THR 350|36.073|20.238|72.399|1.00|25.07|||
|ATOM|2897|HG1 THR 350|36.995|20.003|72.503|1.00|0.00|||
|ATOM|2898|CG2 THR 350|33.888|19.526|71.940|1.00|3.73|||
|ATOM|2899|C THR 350|36.879|17.956|73.755|1.00|10.28|||
|ATOM|2900|O THR 350|37.589|17.027|73.382|1.00|14.11|||
|ATOM|2901|N CYS 351|37.342|18.917|74.540|1.00|11.19|||
|ATOM|2902|H CYS 351|36.766|19.665|74.800|1.00|0.00|||
|ATOM|2903|CA CYS 351|38.717|18.850|75.025|1.00|13.10|||
|ATOM|2904|CB CYS 351|29.052|20.064|75.878|1.00|7.05|||
|ATOM|2905|SG CYS 351|39.198|21.617|74.987|1.00|12.54|||
|ATOM|2906|C CYS 351|38.927|17.571|75.852|1.00|16.59|||
|ATOM|2907|O CYS 351|39.894|16.8839|75.635|1.00|15.17|||
|ATOM|2908|N GLU 352|37.994|17.275|76.760|1.00|16.15|||

-continued

| | | | | | | | | | | | | | |
|---|---|---|---|---|---|---|---|---|---|---|---|---|---|
| ATOM | 2837 | C | VAL | 342 | 27.947 | 26.138 | 75.993 | 1.00 | 11.29 | ATOM | 2909 | H | GLU 352 37.217 17.857 76.863 1.00 0.00 |

```
ATOM   2837  C    VAL 342   27.947  26.138  75.993  1.00  11.29     ATOM   2909  H    GLU 352   37.217  17.857  76.863  1.00   0.00
ATOM   2838  O    VAL 342   28.403  24.999  75.883  1.00  12.19     ATOM   2910  CA   GLU 352   38.123  16.084  77.600  1.00  14.25
ATOM   2839  N    ALA 343   28.404  27.167  75.274  1.00  10.18     ATOM   2911  CB   GLU 352   36.929  15.969  78.578  1.00  14.59
ATOM   2840  H    ALA 343   27.980  28.036  75.376  1.00   0.00     ATOM   2912  CG   GLU 352   37.173  14.954  79.709  1.00  13.70
ATOM   2841  CA   ALA 343   29.524  27.028  74.337  1.00  10.07     ATOM   2913  CD   GLU 352   37.031  13.498  79.276  1.00  13.27
ATOM   2842  CB   ALA 343   29.837  28.384  73.706  1.00   9.90     ATOM   2914  OE1  GLU 352   36.108  13.206  78.486  1.00  12.42
ATOM   2843  C    ALA 343   30.736  26.490  75.120  1.00  12.16     ATOM   2915  OE2  GLU 352   37.807  12.638  79.755  1.00  16.07
ATOM   2844  O    ALA 343   31.438  25.589  74.656  1.00  10.31     ATOM   2916  C    GLU 352   38.188  14.844  76.731  1.00  13.50
ATOM   2845  N    PHE 344   30.943  27.017  76.331  1.00  12.47     ATOM   2917  O    GLU 352   39.051  13.992  76.937  1.00  12.79
ATOM   2846  H    PHE 344   30.340  27.719  76.645  1.00   0.00     ATOM   2918  N    GLN 353   37.291  14.747  75.753  1.00  12.33
ATOM   2847  CA   PHE 344   32.033  26.582  77.214  1.00  13.30     ATOM   2919  H    GLN 353   36.644  15.467  75.626  1.00   0.00
ATOM   2848  CB   PHE 344   32.016  27.372  78.533  1.00  18.23     ATOM   2920  CA   GLN 353   37.270  13.599  74.857  1.00  15.93
ATOM   2849  CG   PHE 344   32.678  28.724  78.460  1.00  21.49     ATOM   2921  CB   GLN 353   36.091  13.712  73.880  1.00  20.18
ATOM   2850  CD1  PHE 344   32.308  29.730  79.349  1.00  25.39     ATOM   2922  CG   GLN 353   34.706  13.664  74.552  1.00  23.36
ATOM   2851  CD2  PHE 344   33.675  28.989  77.523  1.00  23.26     ATOM   2923  CD   GLN 353   34.161  12.251  74.710  1.00  29.07
ATOM   2852  CE1  PHE 344   32.927  30.991  79.310  1.00  28.66     ATOM   2924  OE1  GLN 353   34.862  11.343  75.164  1.00  32.63
ATOM   2853  CE2  PHE 344   34.301  30.241  77.474  1.00  26.03     ATOM   2925  NE2  GLN 353   32.909  12.059  74.337  1.00  27.25
ATOM   2854  CZ   PHE 344   33.927  31.242  78.363  1.00  27.84     ATOM   2926  HE21 GLN 353   32.399  12.824  73.976  1.00   0.00
ATOM   2927  HE22 GLN 353   32.549  11.182  74.446  1.00   0.00     ATOM   2999  O1   HOH 509   35.509  34.054  50.366  1.00  28.21
ATOM   2928  C    GLN 353   38.600  13.409  74.101  1.00  15.86     ATOM   3000  H1   HOH 509   36.107  34.284  51.088  1.00   0.00
ATOM   2929  O    GLN 353   39.115  12.303  74.004  1.00  17.10     ATOM   3001  H2   HOH 509   36.024  33.534  49.772  1.00   0.00
ATOM   2930  N    ILE 354   39.165  14.495  73.600  1.00  16.42     ATOM   3002  O1   HOH 510   34.933  29.155  39.816  1.00  17.84
ATOM   2931  H    ILE 354   38.178  15.358  73.723  1.00   0.00     ATOM   3003  H1   HOH 510   34.218  29.305  40.439  1.00   0.00
ATOM   2932  CA   ILE 354   40.419  14.448  72.865  1.00  15.89     ATOM   3004  H2   HOH 510   34.758  28.333  39.412  1.00   0.00
ATOM   2933  CB   ILE 354   40.734  15.828  72.264  1.00  15.56     ATOM   3005  O1   HOH 511   32.156  31.380  36.574  1.00   7.04
ATOM   2934  CG2  ILE 354   42.126  15.823  71.624  1.00  13.85     ATOM   3006  H1   HOH 511   31.929  30.636  37.023  1.00   0.00
ATOM   2935  CG1  ILE 354   39.629  16.204  71.258  1.00  16.39     ATOM   3007  H2   HOH 511   31.780  31.315  35.697  1.00   0.00
ATOM   2936  CD1  ILE 354   39.605  17.672  70.824  1.00  15.26     ATOM   3008  O1   HOH 512   36.121  30.620  43.066  1.00  21.42
ATOM   2937  C    ILE 354   41.547  14.032  73.795  1.00  18.65     ATOM   3009  H1   HOH 512   35.422  30.730  43.712  1.00   0.00
ATOM   2938  O    ILE 354   42.322  13.123  73.490  1.00  17.76     ATOM   3010  H2   HOH 512   35.887  31.294  42.397  1.00   0.00
ATOM   2939  N    ALA 355   41.628  14.714  74.931  1.00  18.52     ATOM   3011  O1   HOH 513   32.964  30.772  33.972  1.00  14.70
ATOM   2940  H    ALA 355   40.978  15.420  75.103  1.00   0.00     ATOM   3012  H1   HOH 513   32.633  31.248  33.208  1.00   0.00
ATOM   2941  CA   ALA 355   42.644  14.446  75.923  1.00  16.17     ATOM   3013  H2   HOH 513   32.875  29.849  33.758  1.00   0.00
ATOM   2942  CB   ALA 355   42.456  15.374  77.101  1.00  18.27     ATOM   3014  O1   HOH 514   40.740  31.037  44.455  1.00  23.55
ATOM   2943  C    ALA 355   42.540  12.996  76.376  1.00  16.93     ATOM   3015  H1   HOH 514   40.322  31.620  43.854  1.00   0.00
ATOM   2944  O    ALA 355   43.540  12.298  76.507  1.00  16.12     ATOM   3016  H2   HOH 514   40.840  30.227  43.965  1.00   0.00
ATOM   2945  N    ASP 356   41.315  12.532  76.566  1.00  14.46     ATOM   3017  O1   HOH 515   37.112  31.979  55.782  1.00  13.43
ATOM   2946  H    ASP 356   40.554  13.108  76.386  1.00   0.00     ATOM   3018  H1   HOH 515   36.492  31.236  55.780  1.00   0.00
ATOM   2947  CA   ASP 356   41.089  11.168  77.012  1.00  16.37     ATOM   3019  H2   HOH 515   37.691  31.766  56.528  1.00   0.00
ATOM   2948  CB   ASP 356   39.607  10.963  77.351  1.00  12.46     ATOM   3020  O1   HOH 516   34.932  33.743  57.726  1.00  16.34
ATOM   2949  CG   ASP 356   39.386   9.811  78.302  1.00   9.76     ATOM   3021  H1   HOH 516   35.651  34.371  57.865  1.00   0.00
ATOM   2950  OD1  ASP 356   40.259   9.602  79.156  1.00  12.73     ATOM   3022  H2   HOH 516   35.135  33.039  58.319  1.00   0.00
ATOM   2951  OD2  ASP 356   38.367   9.098  78.200  1.00  13.11     ATOM   3023  O1   HOH 517   32.992  35.898  59.122  1.00  13.65
ATOM   2952  C    ASP 356   41.559  10.109  76.004  1.00  18.28     ATOM   3024  H1   HOH 517   32.337  36.031  58.412  1.00   0.00
ATOM   2953  O    ASP 356   41.825   8.969  76.375  1.00  16.16     ATOM   3025  H2   HOH 517   33.543  36.652  59.040  1.00   0.00
ATOM   2954  N    SER 357   41.629  10.478  74.731  1.00  25.77     ATOM   3026  O1   HOH 518   14.064  17.135  60.635  1.00  55.52
ATOM   2955  H    SER 357   41.388  11.394  74.485  1.00   0.00     ATOM   3027  H1   HOH 518   14.963  16.813  60.568  1.00   0.00
ATOM   2956  CA   SER 357   42.053   9.553  73.678  1.00  30.13     ATOM   3028  H2   HOH 518   13.906  16.402  59.956  1.00   0.00
ATOM   2957  CB   SER 357   41.483   9.982  72.321  1.00  33.88     ATOM   3029  O1   HOH 519   12.446  20.018  54.033  1.00  15.26
ATOM   2958  OG   SER 357   40.076   9.818  72.244  1.00  43.35     ATOM   3030  H1   HOH 519   12.575  20.616  54.773  1.00   0.00
ATOM   2959  HG   SER 357   39.849   8.907  72.419  1.00   0.00     ATOM   3031  H2   HOH 519   12.614  19.150  54.431  1.00   0.00
ATOM   2960  C    SER 357   43.567   9.452  73.549  1.00  30.70     ATOM   3032  O1   HOH 520   20.474  15.871  62.473  1.00  11.21
ATOM   2961  O    SER 357   44.079   8.479  73.009  1.00  32.33     ATOM   3033  H1   HOH 520   21.285  15.847  62.978  1.00   0.00
ATOM   2962  N    GLN 358   44.260  10.504  73.966  1.00  35.85     ATOM   3034  H2   HOH 520   20.056  16.690  62.676  1.00   0.00
ATOM   2963  H    GLN 358   43.785  11.252  74.373  1.00   0.00     ATOM   3035  O1   HOH 521   20.705  14.732  59.125  1.00  12.83
ATOM   2964  CA   GLN 358   45.712  10.572  73.895  1.00  39.48     ATOM   3036  H1   HOH 521   21.403  14.640  58.502  1.00   0.00
ATOM   2965  CB   GLN 358   46.154  12.034  73.938  1.00  40.72     ATOM   3037  H2   HOH 521   20.067  15.324  58.723  1.00   0.00
ATOM   2966  CG   GLN 358   45.553  12.900  72.842  1.00  42.43     ATOM   3038  O1   HOH 522   21.233  12.291  57.983  1.00  12.36
ATOM   2967  CD   GLN 358   45.689  14.388  73.136  1.00  48.68     ATOM   3039  H1   HOH 522   20.778  12.810  57.348  1.00   0.00
ATOM   2968  OE1  GLN 358   45.967  14.793  74.269  1.00  51.49     ATOM   3040  H2   HOH 522   21.565  11.520  57.533  1.00   0.00
ATOM   2969  NE2  GLN 358   45.481  15.213  72.115  1.00  51.68     ATOM   3041  O1   HOH 523   13.306  53.673  1.00  20.29
ATOM   2970  HE21 GLN 358   45.256  18.841  71.243  1.00   0.00     ATOM   3042  H1   HOH 523   14.912  13.680  53.140  1.00   0.00
ATOM   2971  HE22 GLN 358   45.575  16.170  72.298  1.00   0.00     ATOM   3043  H2   HOH 523   15.145  12.776  54.328  1.00   0.00
ATOM   2972  C    GLN 358   46.398   9.792  75.017  1.00  41.97     ATOM   3044  O1   HOH 524   14.552  10.615  51.652  1.00  29.13
ATOM   2973  O    GLN 358   47.610   9.493  74.853  1.00  44.23     ATOM   3045  H1   HOH 524   13.775  10.065  51.586  1.00   0.00
ATOM   2974  OT   GLN 358   45.729   9.503  76.042  1.00  39.09     ATOM   3046  H2   HOH 524   15.267  10.000  51.866  1.00   0.00
ATOM   2975  O1   HOH 501   21.113  21.834  31.125  1.00  34.11     ATOM   3047  O1   HOH 525   26.412  10.425  50.161  1.00  21.16
ATOM   2976  H1   HOH 501   20.569  22.495  31.526  1.00   0.00     ATOM   3048  H1   HOH 525   27.168  10.793  50.610  0.00   0.00
ATOM   2977  H2   HOH 501   21.864  22.333  30.772  1.00   0.00     ATOM   3049  H2   HOH 525   25.871  11.187  49.943  1.00   0.00
ATOM   2978  O1   HOH 502   16.027  23.882  32.958  1.00  19.80     ATOM   3050  O1   HOH 526   28.657  16.318  44.297  1.00  10.28
ATOM   2979  H1   HOH 502   16.158  23.419  32.150  1.00   0.00     ATOM   3051  H1   HOH 526   28.391  16.679  43.468  1.00   0.00
ATOM   2980  H2   HOH 502   15.086  23.733  33.200  1.00   0.00     ATOM   3052  H2   HOH 526   27.806  16.001  44.665  1.00   0.00
ATOM   2981  O1   HOH 503   14.494  37.841  36.012  1.00  26.64     ATOM   3053  O1   HOH 527   28.310  18.186  38.834  1.00  11.71
ATOM   2982  H1   HOH 503   14.011  37.975  35.200  1.00   0.00     ATOM   3054  H1   HOH 527   28.155  17.321  39.222  1.00   0.00
ATOM   2983  H2   HOH 503   14.861  36.932  35.886  1.00   0.00     ATOM   3055  H2   HOH 527   27.936  18.078  37.943  1.00   0.00
ATOM   2984  O1   HOH 504   24.785  43.283  29.843  1.00  41.72     ATOM   3056  O1   HOH 528   23.160  13.587  38.766  1.00  11.23
ATOM   2985  H1   HOH 504   24.046  42.664  29.813  1.00   0.00     ATOM   3057  H1   HOH 528   23.349  13.948  37.885  1.00   0.00
ATOM   2986  H2   HOH 504   24.485  44.028  29.328  1.00   0.00     ATOM   3058  H2   HOH 528   22.372  14.053  39.041  1.00   0.00
ATOM   2987  O1   HOH 505   24.609  34.687  30.302  1.00  29.71     ATOM   3059  O1   HOH 529    9.507  21.350  48.406  1.00  23.08
```

-continued

| | | |
|---|---|---|
| ATOM 2988 H1 HOH 505 24.843 35.356 29.653 1.00 0.00 | | ATOM 3060 H1 HOH 529 10.286 21.320 47.818 1.00 0.00 |
| ATOM 2989 H2 HOH 505 24.190 35.172 30.968 1.00 0.00 | | ATOM 3061 H2 HOH 529 8.828 20.950 47.880 1.00 0.00 |
| ATOM 2990 O1 HOH 506 35.336 38.962 49.998 1.00 23.91 | | ATOM 3062 O1 HOH 530 35.924 27.794 54.972 1.00 14.10 |
| ATOM 2991 H1 HOH 506 35.753 39.055 50.828 1.00 0.00 | | ATOM 3063 H1 HOH 530 36.607 28.458 55.108 1.00 0.00 |
| ATOM 2992 H2 HOH 506 35.012 38.056 49.955 1.00 0.00 | | ATOM 3064 H2 HOH 530 36.124 27.392 54.150 1.00 0.00 |
| ATOM 2993 O1 HOH 507 30.302 40.821 56.153 1.00 2.00 | | ATOM 3065 O1 HOH 531 31.190 23.605 44.871 1.00 22.64 |
| ATOM 2994 H1 HOH 507 29.583 40.377 55.722 1.00 0.00 | | ATOM 2066 H1 HOH 531 30.810 24.408 44.486 1.00 0.00 |
| ATOM 2995 H2 HOH 507 30.902 40.142 56.438 1.00 0.00 | | ATOM 2067 H2 HOH 531 30.729 22.895 44.415 1.00 0.00 |
| ATOM 2996 O1 HOH 508 32.683 35.011 50.212 1.00 9.76 | | ATOM 2068 O1 HOH 532 8.072 35.577 49.772 1.00 9.91 |
| ATOM 2997 H1 HOH 508 31.900 34.649 50.413 1.00 0.00 | | ATOM 2069 H1 HOH 532 8.548 36.077 50.422 1.00 0.00 |
| ATOM 2998 H2 HOH 508 32.600 35.145 49.303 1.00 0.00 | | ATOM 2070 H2 HOH 532 7.247 35.987 49.656 1.00 0.00 |
| ATOM 3071 O1 HOH 533 45.213 20.999 82.495 1.00 23.69 | | ATOM 3143 O1 HOH 557 24.340 26.762 57.198 1.00 29.86 |
| ATOM 3072 H1 HOH 533 45.907 20.881 81.842 1.00 0.00 | | ATOM 3144 H1 HOH 557 23.871 27.500 56.759 1.00 0.00 |
| ATOM 3073 H2 HOH 533 44.415 21.134 81.969 1.00 0.00 | | ATOM 3145 H2 HOH 557 24.760 27.183 57.934 1.00 0.00 |
| ATOM 3074 O1 HOH 534 47.201 19.833 81.157 1.00 17.76 | | ATOM 3146 O1 HOH 558 26.379 30.155 58.148 1.00 10.16 |
| ATOM 3075 H1 HOH 534 46.964 19.911 80.228 1.00 0.00 | | ATOM 3147 H1 HOH 558 26.928 29.399 58.399 1.00 0.00 |
| ATOM 3076 H2 HOH 534 47.549 20.689 81.401 1.00 0.00 | | ATOM 3148 H2 HOH 558 26.723 30.844 58.725 1.00 0.00 |
| ATOM 3077 O1 HOH 535 48.572 15.906 76.182 1.00 29.31 | | ATOM 3149 O1 HOH 559 13.369 12.800 56.988 1.00 40.74 |
| ATOM 3078 H1 HOH 535 48.443 16.537 76.895 1.00 0.00 | | ATOM 3150 H1 HOH 559 12.635 12.453 56.463 1.00 0.00 |
| ATOM 3079 H2 HOH 535 47.657 15.791 75.836 1.00 0.00 | | ATOM 3151 H2 HOH 559 14.077 12.176 56.830 1.00 0.00 |
| ATOM 3080 O1 HOH 536 55.029 34.083 73.481 1.00 40.49 | | ATOM 3152 O1 HOH 560 53.861 23.078 74.598 1.00 47.23 |
| ATOM 3081 H1 HOH 536 55.819 33.750 73.902 1.00 0.00 | | ATOM 3153 H1 HOH 560 53.956 23.050 75.549 1.00 0.00 |
| ATOM 3082 H2 HOH 536 54.617 33.307 73.094 1.00 0.00 | | ATOM 3154 H2 HOH 560 53.274 22.301 74.446 1.00 0.00 |
| ATOM 3083 O1 HOH 537 50.980 36.933 65.633 1.00 44.62 | | ATOM 3155 O1 HOH 561 48.624 20.162 69.741 1.00 19.26 |
| ATOM 3084 H1 HOH 537 51.900 37.081 65.437 1.00 0.00 | | ATOM 3156 H1 HOH 561 49.369 19.604 69.997 1.00 0.00 |
| ATOM 3085 H2 HOH 537 50.746 36.133 65.175 1.00 0.00 | | ATOM 3157 H2 HOH 561 48.182 19.644 69.059 1.00 0.00 |
| ATOM 3086 O1 HOH 538 43.014 31.670 58.158 1.00 3.46 | | ATOM 3158 O1 HOH 562 37.820 34.373 64.745 1.00 15.33 |
| ATOM 3087 H1 HOH 538 42.583 32.266 57.558 1.00 0.00 | | ATOM 3159 H1 HOH 562 37.850 33.656 65.323 1.00 0.00 |
| ATOM 3088 H2 HOH 538 43.956 31.791 57.967 1.00 0.00 | | ATOM 3160 H2 HOH 562 37.975 35.155 65.301 1.00 0.00 |
| ATOM 3089 O1 HOH 539 28.529 10.869 68.204 1.00 10.19 | | ATOM 3161 O1 HOH 563 26.510 28.479 82.830 1.00 20.91 |
| ATOM 3090 H1 HOH 539 29.270 10.962 67.620 1.00 0.00 | | ATOM 3162 H1 HOH 563 26.501 29.397 82.536 1.00 0.00 |
| ATOM 3091 H2 HOH 539 27.777 10.817 67.594 1.00 0.00 | | ATOM 3163 H2 HOH 563 25.698 28.133 82.465 1.00 0.00 |
| ATOM 3092 O1 HOH 540 18.863 15.829 69.006 1.00 11.06 | | ATOM 3164 O1 HOH 564 35.083 17.450 63.254 1.00 28.49 |
| ATOM 3093 H1 HOH 540 18.641 14.930 69.228 1.00 0.00 | | ATOM 3165 H1 HOH 564 34.249 17.114 63.557 1.00 0.00 |
| ATOM 3094 H2 HOH 540 19.791 15.910 69.192 1.00 0.00 | | ATOM 3166 H2 HOH 564 34.874 18.055 62.539 1.00 0.00 |
| ATOM 3095 O1 HOH 541 16.474 15.926 70.889 1.00 13.53 | | ATOM 3167 O1 HOH 565 34.570 32.464 85.654 1.00 38.87 |
| ATOM 3096 H1 HOH 541 15.831 15.250 71.030 1.00 0.00 | | ATOM 3168 H1 HOH 565 34.239 31.595 85.561 1.00 0.00 |
| ATOM 3097 H2 HOH 541 16.083 16.738 71.204 1.00 0.00 | | ATOM 3169 H2 HOH 565 35.383 32.452 86.127 1.00 0.00 |
| ATOM 3098 O1 HOH 542 24.752 9.611 61.454 1.00 34.29 | | ATOM 3170 O1 HOH 566 27.590 32.106 29.612 1.00 29.25 |
| ATOM 3099 H1 HOH 542 24.372 10.478 61.588 1.00 0.00 | | ATOM 3171 H1 HOH 566 26.708 32.425 29.591 1.00 0.00 |
| ATOM 3100 H2 HOH 542 25.681 9.801 61.309 1.00 0.00 | | ATOM 3172 H2 HOH 566 27.517 31.161 29.565 1.00 0.00 |
| ATOM 3101 O1 HOH 543 19.120 19.082 75.742 1.00 31.85 | | ATOM 3173 O1 HOH 567 35.194 34.042 36.435 1.00 26.99 |
| ATOM 3102 H1 HOH 543 18.979 18.494 76.468 1.00 0.00 | | ATOM 3174 H1 HOH 567 35.566 34.492 35.707 1.00 0.00 |
| ATOM 3103 H2 HOH 543 19.758 19.728 76.057 1.00 0.00 | | ATOM 3175 H2 HOH 567 35.900 33.706 36.949 1.00 0.00 |
| ATOM 3104 O1 HOH 544 20.890 23.564 81.292 1.00 7.35 | | ATOM 3176 O1 HOH 568 16.603 20.218 77.754 1.00 33.83 |
| ATOM 3105 H1 HOH 544 21.473 22.863 80.979 1.00 0.00 | | ATOM 3177 H1 HOH 568 16.886 19.313 77.800 1.00 0.00 |
| ATOM 3106 H2 HOH 544 20.108 23.467 80.725 1.00 0.00 | | ATOM 3178 H2 HOH 568 15.639 20.159 77.731 1.00 0.00 |
| ATOM 3107 O1 HOH 545 23.258 30.530 79.524 1.00 24.15 | | ATOM 3179 O1 HOH 569 44.260 42.711 49.744 1.00 49.42 |
| ATOM 3108 H1 HOH 545 23.170 29.756 80.060 1.00 0.00 | | ATOM 3180 H1 HOH 569 43.569 42.272 50.249 1.00 0.00 |
| ATOM 3109 H2 HOH 545 22.877 31.208 80.059 1.00 0.00 | | ATOM 3181 H2 HOH 569 45.049 42.209 49.943 1.00 0.00 |
| ATOM 3110 O1 HOH 546 28.803 17.795 82.962 1.00 11.68 | | ATOM 3182 O1 HOH 570 21.872 48.032 53.264 1.00 41.45 |
| ATOM 3111 H1 HOH 546 29.360 17.056 83.227 1.00 0.00 | | ATOM 3183 H1 HOH 570 22.620 48.612 53.236 1.00 0.00 |
| ATOM 3112 H2 HOH 546 27.954 17.405 82.768 1.00 0.00 | | ATOM 3184 H2 HOH 570 21.783 47.696 52.361 1.00 0.00 |
| ATOM 3113 O1 HOH 547 30.182 20.906 85.733 1.00 23.69 | | ATOM 3185 O1 HOH 571 12.792 32.834 61.142 1.00 21.34 |
| ATOM 3114 H1 HOH 547 29.256 20.762 85.836 1.00 0.00 | | ATOM 3186 H1 HOH 571 11.962 32.850 61.572 1.00 0.00 |
| ATOM 3115 H2 HOH 547 30.305 21.821 86.021 1.00 0.00 | | ATOM 3187 H2 HOH 571 13.363 32.323 61.709 1.00 0.00 |
| ATOM 3116 O1 HOH 548 22.573 11.792 73.330 1.00 29.86 | | ATOM 3188 O1 HOH 572 17.695 12.090 61.460 1.00 25.70 |
| ATOM 3117 H1 HOH 548 22.027 11.157 73.769 1.00 0.00 | | ATOM 3189 H1 HOH 572 17.582 13.022 61.236 1.00 0.00 |
| ATOM 3118 H2 HOH 548 22.105 12.046 72.546 1.00 0.00 | | ATOM 3190 H2 HOH 572 16.812 11.737 61.464 1.00 0.00 |
| ATOM 3119 O1 HOH 549 26.762 31.362 66.476 1.00 19.77 | | ATOM 3191 O1 HOH 573 19.834 11.716 53.122 1.00 21.51 |
| ATOM 3120 H1 HOH 549 27.481 30.835 66.104 1.00 0.00 | | ATOM 3192 H1 HOH 573 19.651 12.580 52.717 1.00 0.00 |
| ATOM 3121 H2 HOH 549 25.999 30.809 66.387 1.00 0.00 | | ATOM 3193 H2 HOH 573 20.774 11.693 53.217 1.00 0.00 |
| ATOM 3122 O1 HOH 550 36.271 10.655 77.620 1.00 12.01 | | ATOM 3194 O1 HOH 574 21.268 11.375 45.183 1.00 26.95 |
| ATOM 3123 H1 HOH 550 36.338 11.487 77.960 1.00 0.00 | | ATOM 3195 H1 HOH 574 21.824 11.796 45.845 1.00 0.00 |
| ATOM 3124 H2 HOH 550 35.441 10.668 77.127 1.00 0.00 | | ATOM 3196 H2 HOH 574 21.467 11.858 44.429 1.00 0.00 |
| ATOM 3125 O1 HOH 551 15.409 35.471 35.400 1.00 21.53 | | ATOM 3197 O1 HOH 575 31.324 22.466 47.474 1.00 15.68 |
| ATOM 3126 H1 HOH 551 15.910 35.092 36.113 1.00 0.00 | | ATOM 3198 H1 HOH 575 31.326 22.189 46.553 1.00 0.00 |
| ATOM 3127 H2 HOH 551 15.393 34.800 34.719 1.00 0.00 | | ATOM 3199 H2 HOH 575 31.377 23.423 47.421 1.00 0.00 |
| ATOM 3128 O1 HOH 552 11.203 40.791 44.564 1.00 45.20 | | ATOM 3200 O1 HOH 576 33.771 20.240 41.075 1.00 19.98 |
| ATOM 3129 H1 HOH 552 12.144 40.650 44.489 1.00 0.00 | | ATOM 3201 H1 HOH 576 34.128 20.649 40.260 1.00 0.00 |
| ATOM 3130 H2 HOH 552 10.822 39.934 44.337 1.00 0.00 | | ATOM 3202 H2 HOH 576 34.195 19.384 41.088 1.00 0.00 |
| ATOM 3131 O1 HOH 553 15.641 41.263 47.151 1.00 18.63 | | ATOM 3203 O1 HOH 577 6.251 37.204 48.560 1.00 24.53 |
| ATOM 3132 H1 HOH 553 15.949 40.445 47.518 1.00 0.00 | | ATOM 3204 H1 HOH 577 5.978 36.403 48.041 1.00 0.00 |
| ATOM 3133 H2 HOH 553 15.775 41.187 46.203 1.00 0.00 | | ATOM 3205 H2 HOH 577 6.452 36.906 49.406 1.00 0.00 |
| ATOM 3134 O1 HOH 554 18.730 37.027 57.126 1.00 27.98 | | ATOM 3206 O1 HOH 578 3.214 32.888 43.239 1.00 32.15 |
| ATOM 3135 H1 HOH 554 18.564 36.463 56.358 1.00 0.00 | | ATOM 3207 H1 HOH 578 4.089 32.749 43.668 1.00 0.00 |
| ATOM 3136 H2 HOH 554 19.443 36.558 57.577 1.00 0.00 | | ATOM 3208 H2 HOH 578 3.258 33.840 43.082 1.00 0.00 |
| ATOM 3137 O1 HOH 555 16.938 39.005 58.568 1.00 38.75 | | ATOM 3209 O1 HOH 579 56.568 34.393 67.441 1.00 49.59 |
| ATOM 3138 H1 HOH 555 17.197 39.899 58.352 1.00 0.00 | | ATOM 3210 H1 HOH 579 56.311 34.641 66.555 1.00 0.00 |

-continued

| | |
|---|---|
| ATOM 3139 H2 HOH 555 17.772 38.497 58.439 1.00 0.00 | ATOM 3211 H2 HOH 579 57.351 34.920 67.636 1.00 0.00 |
| ATOM 3140 O1 HOH 556 18.892 30.925 56.057 1.00 23.90 | ATOM 3212 O1 HOH 580 58.741 36.148 68.590 1.00 32.81 |
| ATOM 3141 H1 HOH 556 18.795 30.584 56.919 1.00 0.00 | ATOM 3213 H1 HOH 580 58.738 37.120 68.606 1.00 0.00 |
| ATOM 3142 H2 HOH 556 19.544 31.632 56.110 1.00 0.00 | ATOM 3214 H2 HOH 580 58.745 35.930 67.671 1.00 0.00 |
| ATOM 3215 O1 HOH 581 39.287 14.270 67.499 1.00 27.97 | ATOM 3287 O1 HOH 605 36.759 26.472 88.853 1.00 37.02 |
| ATOM 3216 H1 HOH 581 39.735 13.617 68.033 1.00 0.00 | ATOM 3288 H1 HOH 605 37.215 27.264 89.016 1.00 0.00 |
| ATOM 3217 H2 HOH 581 38.408 14.341 67.837 1.00 0.00 | ATOM 3289 H2 HOH 605 37.052 25.865 89.547 1.00 0.00 |
| ATOM 3218 O1 HOH 582 28.772 30.853 71.752 1.00 31.27 | ATOM 3290 O1 HOH 606 45.889 12.777 77.808 1.00 29.70 |
| ATOM 3219 H1 HOH 582 29.020 30.472 72.403 1.00 0.00 | ATOM 3291 H1 HOH 606 46.668 13.027 78.263 1.00 0.00 |
| ATOM 3220 H2 HOH 582 27.819 30.976 71.645 1.00 0.00 | ATOM 3292 H2 HOH 606 46.100 11.889 77.426 1.00 0.00 |
| ATOM 3221 O1 HOH 583 26.666 31.233 69.212 1.00 18.23 | ATOM 3293 O1 HOH 607 31.969 23.314 50.191 1.00 38.01 |
| ATOM 3222 H1 HOH 583 26.111 30.606 68.803 1.00 0.00 | ATOM 3294 H1 HOH 607 32.051 22.367 50.238 1.00 0.00 |
| ATOM 3223 H2 HOH 583 26.463 31.287 70.130 1.00 0.00 | ATOM 3295 H2 HOH 607 32.538 23.517 49.481 1.00 0.00 |
| ATOM 3224 O1 HOH 584 28.515 33.652 72.493 1.00 32.78 | ATOM 3296 O1 HOH 608 34.488 26.820 47.965 1.00 37.07 |
| ATOM 3225 H1 HOH 584 28.746 33.818 73.377 1.00 0.00 | ATOM 3297 H1 HOH 608 34.171 26.367 47.165 1.00 0.00 |
| ATOM 3226 H2 HOH 584 29.077 34.230 71.971 1.00 0.00 | ATOM 3298 H2 HOH 608 34.253 26.192 48.656 1.00 0.00 |
| ATOM 3227 O1 HOH 585 33.452 31.259 68.561 1.00 18.22 | ATOM 3299 O1 HOH 609 22.027 49.801 35.605 1.00 36.28 |
| ATOM 3228 H1 HOH 585 34.169 31.848 68.460 1.00 0.00 | ATOM 3300 H1 HOH 609 21.466 49.284 35.038 1.00 0.00 |
| ATOM 3229 H2 HOH 585 32.798 31.604 67.959 1.00 0.00 | ATOM 3301 H2 HOH 609 22.457 50.431 35.038 1.00 0.00 |
| ATOM 3230 O1 HOH 586 38.431 40.677 59.022 1.00 29.80 | ATOM 3302 O1 HOH 610 34.267 19.550 45.395 1.00 41.99 |
| ATOM 3231 H1 HOH 586 39.024 41.173 58.436 1.00 0.00 | ATOM 3303 H1 HOH 610 34.071 20.126 44.666 1.00 0.00 |
| ATOM 3232 H2 HOH 586 38.787 39.792 59.006 1.00 0.00 | ATOM 3304 H2 HOH 610 35.224 19.450 45.388 1.00 0.00 |
| ATOM 3233 O1 HOH 587 14.214 22.425 34.386 1.00 33.05 | ATOM 3305 O1 HOH 611 52.119 25.683 61.288 1.00 41.57 |
| ATOM 3234 H1 HOH 587 13.445 21.830 34.508 1.00 0.00 | ATOM 3306 H1 HOH 611 51.694 26.226 61.981 1.00 0.00 |
| ATOM 3235 H2 HOH 587 14.727 21.982 33.728 1.00 0.00 | ATOM 3307 H2 HOH 611 52.670 25.093 61.763 1.00 0.00 |
| ATOM 3236 O1 HOH 588 11.513 23.667 35.426 1.00 42.66 | ATOM 3308 O1 HOH 612 37.621 20.380 57.482 1.00 34.82 |
| ATOM 3237 H1 HOH 588 12.378 23.931 35.082 1.00 0.00 | ATOM 3309 H1 HOH 612 38.060 19.607 57.100 1.00 0.00 |
| ATOM 3238 H2 HOH 588 11.508 24.024 36.320 1.00 0.00 | ATOM 3310 H2 HOH 612 36.838 20.510 56.991 1.00 0.00 |
| ATOM 3239 O1 HOH 589 13.301 30.707 39.584 1.00 29.17 | |
| ATOM 3240 H1 HOH 589 13.479 30.983 40.491 1.00 0.00 | |
| ATOM 3241 H2 HOH 589 13.621 31.461 39.079 1.00 0.00 | |
| ATOM 3242 O1 HOH 590 19.672 44.315 53.325 1.00 41.86 | |
| ATOM 3243 H1 HOH 590 19.608 44.468 52.368 1.00 0.00 | |
| ATOM 3244 H2 HOH 590 19.001 43.668 53.491 1.00 0.00 | |
| ATOM 3245 O1 HOH 591 39.643 38.244 53.938 1.00 27.16 | |
| ATOM 3246 H1 HOH 591 39.900 39.085 54.329 1.00 0.00 | |
| ATOM 3247 H2 HOH 591 38.704 38.198 54.058 1.00 0.00 | |
| ATOM 3248 O1 HOH 592 18.025 32.839 57.830 1.00 32.72 | |
| ATOM 3249 H1 HOH 592 18.946 32.662 57.857 1.00 0.00 | |
| ATOM 3250 H2 HOH 592 17.664 32.568 58.686 1.00 0.00 | |
| ATOM 3251 O1 HOH 593 17.303 10.921 54.069 1.00 26.92 | |
| ATOM 3252 H1 HOH 593 18.237 10.758 54.241 1.00 0.00 | |
| ATOM 3253 H2 HOH 593 17.350 11.747 53.536 1.00 0.00 | |
| ATOM 3254 O1 HOH 594 20.129 9.475 51.235 1.00 24.40 | |
| ATOM 3255 H1 HOH 594 20.501 8.710 50.822 1.00 0.00 | |
| ATOM 3256 H2 HOH 594 20.735 10.190 51.037 1.00 0.00 | |
| ATOM 3257 O1 HOH 595 9.777 26.290 50.831 1.00 37.95 | |
| ATOM 3258 H1 HOH 595 8.909 26.442 50.397 1.00 0.00 | |
| ATOM 3259 H2 HOH 595 9.816 27.023 51.445 1.00 0.00 | |
| ATOM 3260 O1 HOH 596 50.629 25.842 82.360 1.00 59.98 | |
| ATOM 3261 H1 HOH 596 50.530 25.393 83.200 1.00 0.00 | |
| ATOM 3262 H2 HOH 596 50.950 26.712 52.589 1.00 0.00 | |
| ATOM 3263 O1 HOH 597 48.511 43.589 61.934 1.00 37.97 | |
| ATOM 3264 H1 HOH 597 47.854 43.556 62.597 1.00 0.00 | |
| ATOM 3265 H2 HOH 597 48.406 42.811 61.392 1.00 0.00 | |
| ATOM 3266 O1 HOH 598 36.392 36.630 64.471 1.00 18.46 | |
| ATOM 3267 H1 HOH 598 35.592 37.143 64.368 1.00 0.00 | |
| ATOM 3268 H2 HOH 598 36.881 36.849 63.658 1.00 0.00 | |
| ATOM 3269 O1 HOH 599 32.970 38.963 63.176 1.00 36.80 | |
| ATOM 3279 H1 HOH 599 32.057 39.224 63.225 1.00 0.00 | |
| ATOM 3271 H2 HOH 599 33.135 38.453 63.965 1.00 0.00 | |
| ATOM 3272 O1 HOH 600 33.301 30.677 60.530 1.00 29.65 | |
| ATOM 3273 H1 HOH 600 32.930 29.769 60.462 1.00 0.00 | |
| ATOM 3274 H2 HOH 600 32.913 30.997 61.360 1.00 0.00 | |
| ATOM 3275 O1 HOH 601 32.209 18.034 57.926 1.00 16.83 | |
| ATOM 3276 H1 HOH 601 32.571 18.189 58.807 1.00 0.00 | |
| ATOM 3277 H2 HOH 601 32.293 17.089 57.803 1.00 0.00 | |
| ATOM 3278 O1 HOH 602 42.025 13.710 67.531 1.00 41.72 | |
| ATOM 3279 H1 HOH 602 42.000 13.498 68.453 1.00 0.00 | |
| ATOM 3280 H2 HOH 602 42.530 14.512 67.456 1.00 0.00 | |
| ATOM 3281 O1 HOH 603 32.784 8.013 66.048 1.00 31.46 | |
| ATOM 3282 H1 HOH 603 33.139 7.169 65.772 1.00 0.00 | |
| ATOM 3283 H2 HOH 603 33.424 8.293 66.718 1.00 0.00 | |
| ATOM 3284 O1 HOH 604 42.347 32.216 46.922 1.00 26.11 | |
| ATOM 3285 H1 HOH 604 42.468 33.068 47.176 1.00 0.00 | |
| ATOM 3286 H2 HOH 604 43.218 31.862 47.060 1.00 0.00 | |

In yet a further embodiment, the present invention provides a crystallized polypeptide having the three-dimensional crystal structure set forth in the previous table. The present invention also provides a method for designing a candidate compound for screening as an antiviral for the prevention or treatment of influenza virus infection, comprising evaluating the three-dimensional crystal structure set forth in the previous table and synthesizing a candidate compound based on the three-dimensional crystal structure. In a further embodiment, the candidate compound is a peptide. In yet another embodiment, the present invention provides for the use of the three-dimensional crystal structure as set forth in the previous table for screening candidate compounds for inhibition of influenza virus M1.

In a further embodiment, the present invention provides for the use of the N-terminal domain of M1 as described herein for screening candidate compounds for inhibition of influenza virus M1.

The present invention also provides a crystallized N-terminal domain of M1.

The use of the crystal structure to design candidate antivirals may be accomplished in the following fashion. Once the crystal structure of the target (e.g., the N-terminal domain of M1) is determined, computer modeling is conducted (using such as programs DOCK or Multiple Copy Simultaneous Search (MCSS)) to construct candidate inhibitor compounds based on the crystal structure. These compounds are chemically synthesized and their biological activity is assayed. For those compounds which show activity, they are associated or complexed with the crystal for further X-ray diffraction analysis to map the interactions of the compound with the crystal structure.

From the resulting inhibitor-target crystal structure, one of ordinary skill in the art could construct further improved candidate compounds. The steps set forth in the preceding paragraph are repeated and refined as desired.

With this in mind, examples using the preferred embodiments of the above-described methods and structures are set forth hereinbelow. Other features of the invention will become apparent from the following examples, which are for illustrative purposes only and are not intended as a limitation upon the present invention.

EXAMPLE I

Virus Preparation

Since M1 constitutes 40% of the total protein in the influenza virus, intact virions were used as the source for purification of the M1 protein. This also ensures that the M1 protein under study is authentic. Attempts to express the whole protein or M1 fragments in *E. coli* failed to produce any useful protein. Influenza virus strain A/PR/8/34 was inoculated in 11-day-old embryonated eggs (Hyvac Lab, Iowa) followed by incubation at 34.5° C. for 48 hours. The allantoic fluid was harvested at the end of incubation, and was centrifuged at 8,000 rpm in a Beckman JA10 rotor for 20 minutes at 4° C. Virus which stayed in the supernatant was concentrated by about 15 fold through an Amicon concentrator in a 4° C. cold room. The virus was pelleted in a Beckman Ti 45 rotor at 20K rpm for three hours at 4° C. The virus pellet was then soaked in $Ca^{++}Mg^{++}$-Saline (0.2 mM $CaCl_2$, 0.8 mM $MgCl_2$, 0.15 M NaCl) solution overnight. The softened pellet was resuspended by pipetting gently to complete suspension. The virus solution was then subjected to centrifugation on a 10%–40% linear sucrose gradient in a Beckman SW28 rotor at 17K rpm for 40 minutes at 4° C. The virus band was collected from the upper middle area, and was pelleted again in a Beckman SW28 rotor at 25K rpm for three hours at 4° C. Finally, the virus was resuspended in $Ca^{++}Mg^{++}$-Saline solution for storage.

EXAMPLE II

Protein Extraction and Purification

In order to strip off the lipid membrane and the membrane embedded surface proteins, 1 M1 of the purified virus preparation was loaded on a three-step sucrose gradient (8). The gradient consisted of, from bottom to top, 3 M1 32% sucrose and 5 M1 17% sucrose in 0.15 M NaCl, 10 mM Hepes (pH 7.2) containing 1% of nonionic detergent NP40, and 2 M1 10% sucrose in 0.15 M NaCl, 10 mM Hepes (pH 7.2) without detergent. After centrifugation in a Beckman SW41 rotor at 21 K rpm for three hours at 4° C., the M1-RNP complex was pelleted to the bottom of the centrifuge tube whereas the membrane associated proteins stayed in the gradient solution. The pellet of the M1-RNP complex was resuspended in 1 M1 of 50 mM $NaH_2PO_4$ 50 mM, 5 mM Benzamidine and 0.02% $NaN_3$ (pH of from 3.0 to 5.0, preferably 4.0) to release the M1 protein from the M1-RNP complex (8). The RNP cores (lacking M1) were removed by centrifugation in a Beckman SW55 rotor at 22K rpm for one hour at 4° C.

The M1 protein was further purified by gel filtration in a column of Superdex 75 (Pharmacia) mounted on a Pharmacia FPLC system. The M1 protein was pooled about 62 minutes after sample injection at a flow rate of 1 M1/min. Compared with the molecular weights of the protein standards, the apparent molecular weight of the eluted M1 protein was about 50 kd. Because the molecular weight of M1 monomer derived from its amino acid sequence was expected to be 27 kd (11), the M1 protein appears to form a dimer in solution at acidic pH.

However, the M1 protein was not stable when concentrated to 5 mg/ml prior to crystallization. A stable fragment of 18 Kd was identified after two week storage of the concentrated protein sample at room temperature. Dot-blotting showed that this major fragment of the M1 protein was still recognized by rabbit anti-M1 polyclonal antibodies. The molecular weight of the fragment was determined by Mass Spectrum (PE Sciex API III) to be 18,230 dalton. The M1 fragment remained soluble after transfer of the concentrated protein into a buffer with pH 7.2. The soluble fragment, at pH 7.2, was then incubated with M1-free RNP cores obtained during M1 purification. The mixture was pelleted and analyzed by SDS-PAGE gel. The gel showed that, similar to the native M1 protein, the M1 fragment was still able to bind RNP cores at neutral pH.

Since this fragment can still bind to RNP cores, M1 can be conceptualized as a two-domain protein. The C-terminal domain binds the RNP cores through hydrophilic interactions which can be interrupted by reducing the pH. The N-terminal domain binds the membrane. Without wishing to be bound by theory, the N-terminal domain probably has hydrophobic properties because the intact M1 protein aggregates at neutral pH while the C-terminal domain binds the RNP cores through hydrophilic interactions which can be interrupted by reducing the pH. The N-terminal end thus binds the membrane. The concept of a two domain protein is consistent with the function of M1. During virus production, M1 is synthesized and transported to the nucleus as a dimer where it binds to RNP cores by the C-terminal domain. This is consistent with the RNA binding and anti-transcriptase activity data which were mapped by monoclonal antibodies to be within the amino acid sequence at from position 90 to position 164. The association of M1 with RNP cores signals, perhaps through a conformational change of M1, the transportation of the M1-RNP complex to the assembly site on the cellular membrane. Only the RNP-associated M1 N-terminal domain can bind to the membrane and the C-terminal tails of the spike glycoproteins, HA and NAA. This completes the function of M1 during virion assembly. During virion entry, the C-terminal domain of M1 is dissociated from the RNP cores due to the low pH of the fusion endosome while the N-terminal domain remains associated with the membrane and the spike glycoprotein tails by hydrophobic interactions. The dissociation of M1 releases naked RNP cores and uncovers the signal for nucleus targeting carried by RNP cores. The virion M1 could not block the transportation of entering RNP cores into the nucleus because of conformational changes induced by low pH. Unlike the matrix protein of human immunodeficiency virus (HIV) and simian immunodeficiency virus (SIV), which are single domain proteins forming a trimer, the M1 protein is a two domain protein functioning as a dimer. The membrane anchoring of M1 occurs through an entirely separate N-terminal protein domain, rather than a covalent myristoyl modification, as found in HIV and SIV matrix proteins.

EXAMPLE III

Crystallization, Data Collection and Processing

Crystallization was carried out in hanging drops by the vapor diffusion method. However, one of skill in the art would recognize that other crystallization methods may be used. For instance, a temperature variation method may be used to produce crystals, while crystallization in outer space may be used to improve resolution. Nonetheless, for the hanging drop method, the protein concentration was about 5 mg/ml. Large crystals (0.05 mm×0.05 mm×0.3 mm) of the 18 kd M1 protein fragment could be grown at 20° C. over 20% PEG 3350 in two months. X-ray diffraction data were collected at the Brookhaven National Laboratory on beaM1ine X-12C. 60 frames from two crystals were collected and the data were processed by the HKL package. The crystals were classified as belonging to space group $P3_121$ or $P3_221$ with a =68.74Å, c=136.57 Å. The data were about 56% complete to 2.35 U resolution and the Rsymm was 0.11 when reflections with 1>2*sigma(1) were included in the statistics. The Vm value is 2.50 for two monomers per asymmetric unit, which is within the range of normal protein crystals. A further native data set (to 2.1 Å resolution) was collected at NSLS under cryo conditions and the statistics are shown in Table 1.

TABLE 1

The Native Data from NSLS Synchrotron

| Res. limits (Å) | | I/sigma (I) | Rsymm % | % of observations | Observations/ reflections |
|---|---|---|---|---|---|
| 25.00 | 3.78 | 44.1 | 2.7 | 95.4 | 2.8 |
| 3.78 | 3.00 | 42.4 | 3.9 | 96.0 | 3.0 |
| 3.00 | 2.62 | 33.0 | 5.4 | 95.9 | 3.0 |
| 2.62 | 2.38 | 24.6 | 7.8 | 96.0 | 3.0 |
| 2.38 | 2.21 | 18.5 | 10.2 | 95.9 | 3.0 |
| 2.21 | 2.08 | 9.11 | 17.5 | 88.6 | 2.6 |
| All | | 33.7 | 4.6 | 94.7 | 2.9 |

Space group: $P3_121$, a = b = 67.17 Å, c-135.30 Å

Because there are no reported homologous structures to M1, the structural solution relies on the conventional multiple isomorphous replacement method. Three data sets were collected under identical conditions from a SIEMENS Highstar multiwire detector, mounted on a Rigaku rotating anode source with the Oxford cryo system. These three data sets are a new native and two derivative data sets. The statistics are shown in Table 2.

TABLE 2

Refinement of heavy Atom Parameters

| | Native | $K_2PtCl_4$ | $K2OsFCl_6$ |
|---|---|---|---|
| Resolution | 3.5Å | 3.5Å | 3.5Å |
| Completeness | 96.2% | 94.4% | 75.9% |
| Rsymm | 4.2% | 4.7% | 3.1% |
| Rcullis | | 0.77 | 0.76 |
| Phasing power | | 1.19 | 1.89 |
| Position | | .577, .385, .439 | .514, .115, .477 |

FOM = 0.52

Figure 2A:
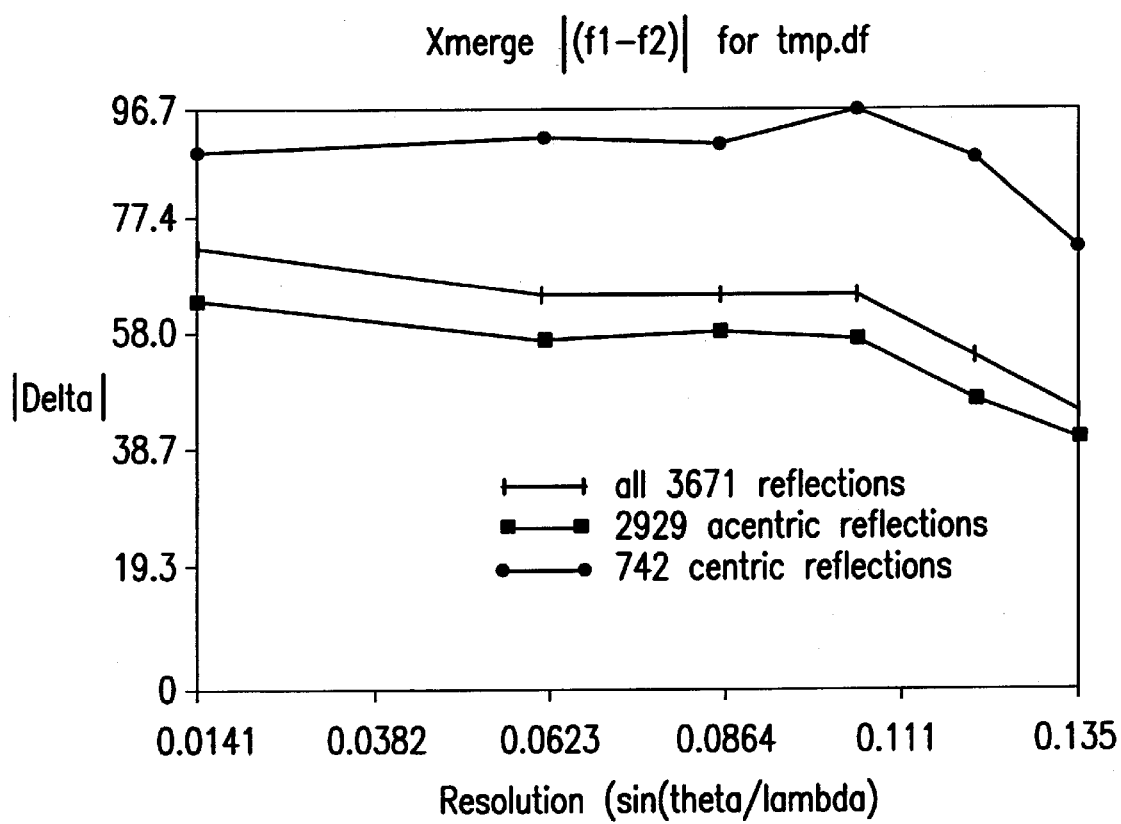
FIG. 2a shows the structure factor amplitude difference between native and Pt derivative data sets versus resolution. From top to bottom, the curves are for all reflections, acentric reflections and centric reflections, respectively.
Figure 2B:
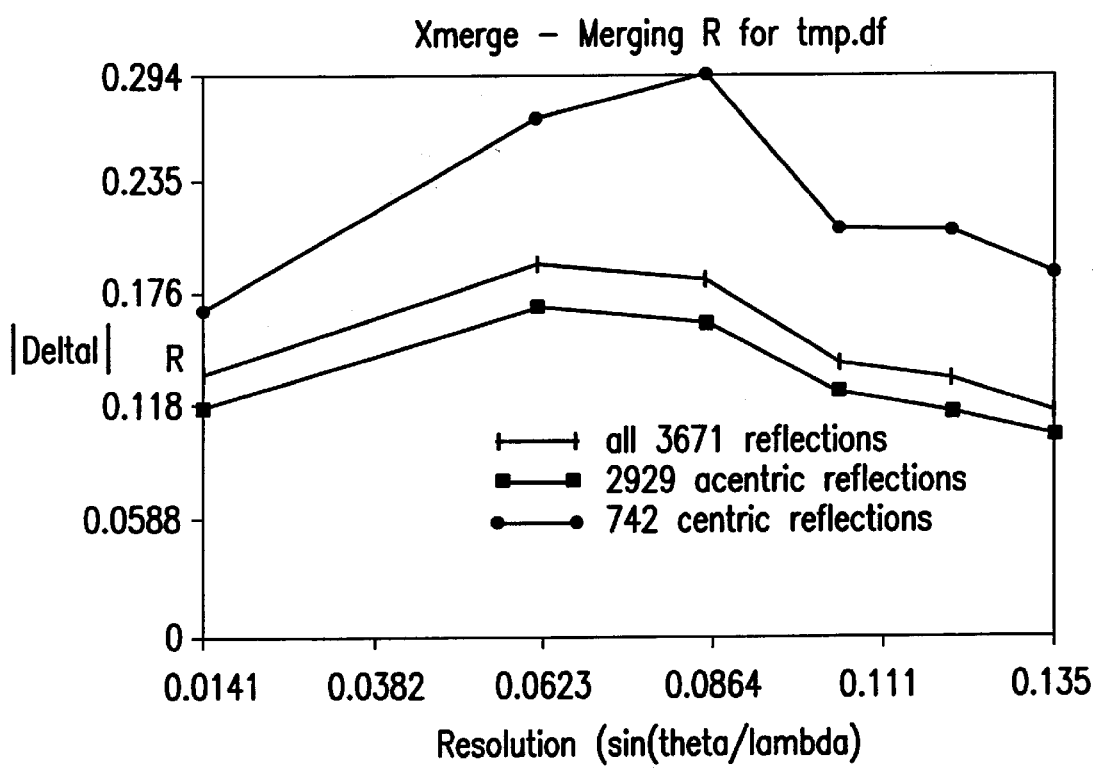
FIG. 2b shows the merging R-factor between native and Pt derivative data sets versus resolution. From top to bottom, the curves are for all reflections, acentric reflections and centric reflections, respectively.
Figure 2C:
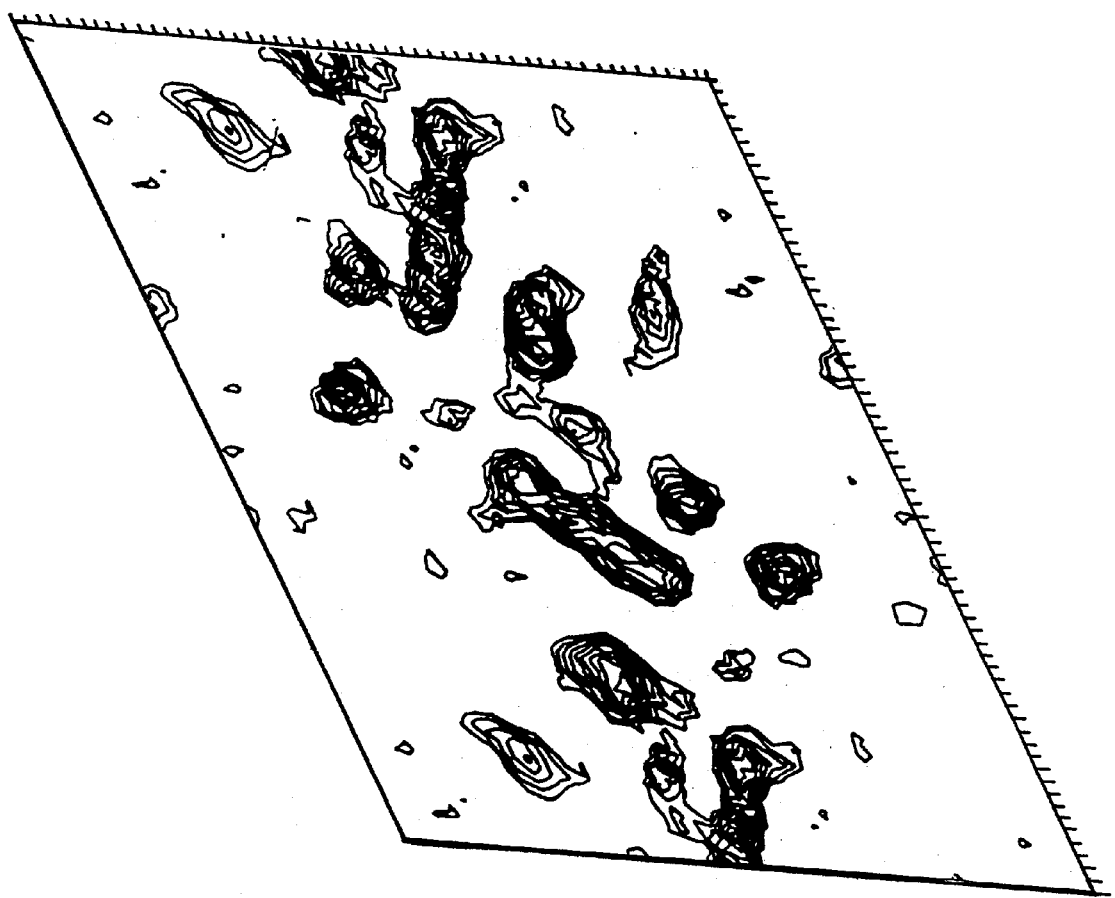
FIG. 2c shows a section of solvent flattened map (FOM= 0.89) at 5 Å resolution.
Figure 2D:
FIG. 2d shows a slice of electron density map at 3.5 Å resolution corresponding to an alpha-helix.

The Harker section of the difference patterns of the Os and Pt derivatives are shown in FIGS. 1a, 1b, 1c, 1d, 2a, 2b, 2c and 2d. The amplitude difference and merging R factors versus resolution for the two derivatives are shown also shown in FIGS. 1a, 1b, 1c, 1d, 2a, 2b, 2c and 2d. Finally, a section of solvent flattened map (FOM=0.89) at 5 Å resolution is shown in FIG. 2c, and a region corresponding to an α-helix at 3.5 Å is shown in FIG. 2d.

REFERENCES

The following references are incorporated in their entirety herein by this reference:

1. Pons, M. W., Schulze, I. T., Hirst, G. K. and Hauser, R., *Isolation and characterization of the ribonucleoprotein of influenza virus*, VIROLOGY 39:250–259 (1969).
2. Helenius, A., *Unpacking the incoming influenza virus,* CELL 69:577–578 (1992).
3. Ye, Z., Pal, R., Fox, W. and Wagner, R. R., *Functional and antigenic domains of the matrix* (M1) *protein of influenza A virus,* J. VIROL. 61:239–246 (1987).
4. Bucher, D. J., Kharitonenkov, I. G., Zakomirdin, J. A., Grigoriev, V. B., Klimenko, S. M. and Davis, J. F., *Incorporation of influenza virus M-protein into liposomes,* J. VIROL. 36:586–590 (1980).
5. Wakefield, L. and Brownlee, G. G., *RNA-binding properties of influenza A virus matrix protein* M1, NUCLEIC ACIDS RES. 17:8569–8580 (1989).
6. Winter, G. and Fields, S., *The structure of the gene enclosing the nucleoprotein of human influenza virus A/PR/8/34,* VIROLOGY 114:423–428 (1981).
7. Zhirnov., O. P., *Solubilization of matrixprotein M1/M from virions occurs at different pH for Orthomyxo- and Paramyxoviruses,* VIROLOGY 176:274–279 (1990).
8. Zhirnov., O. P., *Isolation of matrix protein M1 from influenza virus by acid-dependent extraction with nonionic detergent,* VIROLOGY 186:324–330 (1992).
9. Martin, K. and Helenius, A., *Transport of incoming influenza virus nucleocapsids into the nucleus,* J. VIROLOGY 65:232–244 (1991).
10. Martin, K. and Helenius, A., *Nuclear transport of influenza virus ribonucleoproteins: the viral matrix protein* (ml) *promotes export and inhibits import,* CELL 67:117–130 (1991).
11. Winter, G. and Fields, S., *Cloning of influenza cDNA into M*13: *the sequence of the RNA segment encoding the A/PR/8/34 matrix protein,* NUCLEIC ACIDS RES. 8:1965–1974 (1980).
12. Otwinowsli, Z. and Minor, W., *An oscillation data processing suite for macromolecular crystallography,* (1995).

13. Matthews, B. W., *Solvent content of protein crystals,* J. MOL. Bio. 33:491–497 (1968).
14. Ye, Z., Baylor, N. W. and Wagner, R. R., *Transcription-inhibition and RNA-binding domains of influenza A virus matrix protein mapped with anti-idiotypic antibodies and synthetic peptides,* J. VIROL. 63:3586–3594 (1989).
15. Hankins, R. W., Nagata, K., Bucher, D. J., Popples, S. and Ishihama, A., *Monoclonal antibody analysis of influenza virus matrix protein epitopes involved in transcription inhibition,* VIRUS GENES. 3(2):111–126, (1989).

Sequence Listing

SEQ. ID. NO. 1 represents amino acids 2–164 of the N-terminal domain of influenza virus matrix protein M1:

SEQ. ID. NO.1: SLLTEVETYVLSIIPS- GPLKAE-IAQRLED VFAGKNTDLEVLMEWLKTR- PILSPLT-KGILGFVFTLTVPSERGLQRRRFVQNAL-NGNGDPNNMDKAVKLYRKLKREITIF HGAKEISLSYSAGALASCMGLIYNRM-GAVTTEVAFGLVCATCEQIADSQHRSHRQ

It will be apparent to those skilled in the art that various modifications and variations can be made in the present invention without departing from the scope or spirit of the invention. Other embodiments of the invention will be apparent to those skilled in the art from consideration of the specification and practice of the invention disclosed herein. It is intended that the specification and examples be considered as exemplary only, with the true scope and spirit of the invention being indicated by the following claims.

What is claimed is:

1. A crystallized N-terminal domain of the M1 protein of influenza virus comprising the amino acid sequence set forth in the Sequence Listing as SEQ ID NO:1, wherein the N-terminal domain of M1 is crystallized to obtain crystals of space group $P3_221$ or $P3_221$ with approximate a=68.0 Å and approximate c=136.57 Å such that the three dimensional structure of the crystallized N-terminal domain of M1 can be determined to a resolution of about 2.1 Å or better.

2. A method of extracting and purifying the M1 protein of influenza virus comprising:
   a) stripping the membrane proteins from influenza virus;
   b) removing the stripped membrane proteins, thereby leaving the M1-RNP complex;
   c) releasing M1 from the M1-RNP complex by suspending the complex in a solution comprising $NaH_2PO_4$, Benzamidine, and $NaN_3$; and
   d) purifying the released M1 by FPLC chromatography.

3. A method of extracting the N-terminal domain of the M1 protein of influenza virus comprising the amino acid sequence set forth in the Sequence Listing as SEQ ID NO:1 comprising:

a) stripping the membrane proteins from influenza virus;

b) removing the stripped membrane proteins, thereby leaving the M1-RNP complex;

c) releasing M1 from the M1-RNP complex by suspending the complex in a solution comprising $NaH_2PO_4$, Benzamidine, and $NaN_3$;

d) purifying the released M1;

e) concentrating the purified M1 to a concentration of from 3 mg/ml to 20 mg/ml; and f) after a period of time sufficient for the formation of an 18 kd protein fragment corresponding to the N-terminal domain of M1, collecting the 18 kd polypeptide corresponding to the N-terminal domain of M1.

4. The method of claim 3, wherein the time period is from 7 to 21 days.

5. The method of claim 3, further comprising crystallizing the 18 kd polypeptide corresponding to the N-terminal domain of M1 to a resolution of less than about 2.1 Å, wherein the N-terminal domain of M1 is present at a concentration of from 3 to 20 mg/ml and the crystallization takes place at from 4 to 32° C. to thereby obtain crystals of space group $P3_121$ or $P3_221$.

6. The method of claim 3, wherein the pH of the solution of step c) is from 3.0 to 5.0.

7. The method of claim 5, wherein the crystallization occurs in hanging drops using the vapor diffusion method.

8. A method for determining the three dimensional structure of the crystallized N-terminal domain of the M1 protein of influenza virus comprising the amino acid sequence set forth in the Sequence Listing as SEQ ID NO:1 to a resolution of about 2.1 Å or better comprising the steps of crystallizing the N-terminal domain of M1 to a resolution of about 2.1 Å, wherein the N-terminal domain of M1 is present at a concentration of from 3 to 20 mg/ml and the crystallization takes place at from 4 to 32° C., to thereby obtain crystals of space group $P3_121$ or $P3_221$, and then analyzing the N-terminal domain of M1 to determine the three-dimensional structure of the crystallized N-terminal domain of M1.

9. The method of claim 8, wherein the analyzing is by x-ray diffraction.

10. The method of claim 8, wherein the crystallization occurs in hanging drops using the vapor diffusion method.

11. The crystallized N-terminal domain of M1 produced by the process of claim 5.

12. A method for designing a potential antiviral compound for the prevention or treatment of influenza virus infection, comprising:

a. obtaining crystals of the N-terminal domain of M1, wherein the crystals have the space group $P3_121$ or $P3_221$ with approximate a=68.0 Å and approximate c=136.57 Å such that the three dimensional structure of the crystallized N-terminal domain of M1 can be determined to a resolution of about 2.1 Å or better, b. evaluating the three dimensional structure of the crystallized N-terminal domain of M1;

c) synthesizing the potential antiviral compound based on the three-dimensional crystal structure of the crystallized N-terminal domain of M1;

d) contacting an influenza virus or an influenza viral protein with the potential antiviral compound; and e) assaying the influenza virus for infectivity or monitoring the influenza viral protein for activity, or both, whereby a decrease in the infectivity of the influenza virus or a change in the activity of the influenza virus protein indicates the compound may be used for the prevention or treatment of influenza virus infection.

13. The method of claim 12, wherein the antiviral compound is a peptide or polypeptide.

14. The method of claim 12, wherein the crystallization occurs in hanging drops using the vapor diffusion method.

15. The method of claim 12, wherein the crystal has the three dimensional crystal structure of influenza virus protein M1 as set forth in FIG. 3.

16. The method of claim 12, wherein the influenza viral protein comprises M1.

17. A method for designing a candidate compound for screening for binding to or inhibition of influenza virus M1, comprising:

a) utilizing the three dimensional structure of a crystallized N-terminal domain of M1 which is defined by the atomic coordinates in FIG. 3; and b) designing a candidate binding compound based on the three-dimensional crystal structure of the crystallized N-terminal domain of M1 for binding to M1.

18. The method of claim 17, wherein the candidate compound is a peptide or polypeptide.

* * * * *

SEQUENCE LISTING

<160> NUMBER OF SEQ ID NOS: 1

<210> SEQ ID NO 1
<211> LENGTH: 163
<212> TYPE: PRT
<213> ORGANISM: Influenza Virus

<400> SEQUENCE: 1

```
Ser Leu Leu Thr Glu Val Glu Thr Tyr Val Leu Ser Ile Ile Pro Ser
 1               5                  10                  15

Gly Pro Leu Lys Ala Glu Ile Ala Gln Arg Leu Glu Asp Val Phe Ala
            20                  25                  30

Gly Lys Asn Thr Asp Leu Glu Val Leu Met Glu Trp Leu Lys Thr Arg
        35                  40                  45

Pro Ile Leu Ser Pro Leu Thr Lys Gly Ile Leu Gly Phe Val Phe Thr
    50                  55                  60

Leu Thr Val Pro Ser Glu Arg Gly Leu Gln Arg Arg Arg Phe Val Gln
65                  70                  75                  80

Asn Ala Leu Asn Gly Asn Gly Asp Pro Asn Asn Met Asp Lys Ala Val
                85                  90                  95

Lys Leu Tyr Arg Lys Leu Lys Arg Glu Ile Thr Phe His Gly Ala Lys
            100                 105                 110

Glu Ile Ser Leu Ser Tyr Ser Ala Gly Ala Leu Ala Ser Cys Met Gly
        115                 120                 125

Leu Ile Tyr Asn Arg Met Gly Ala Val Thr Thr Glu Val Ala Phe Gly
    130                 135                 140

Leu Val Cys Ala Thr Cys Glu Gln Ile Ala Asp Ser Gln His Arg Ser
145                 150                 155                 160

His Arg Gln
```